United States Patent
Berkman et al.

(10) Patent No.: US 11,225,496 B2
(45) Date of Patent: Jan. 18, 2022

(54) CHELATED PSMA INHIBITORS

(71) Applicant: Cancer Targeted Technology LLC, Woodinville, WA (US)

(72) Inventors: Clifford Berkman, Pullman, WA (US); Cindy Choy, Pullman, WA (US)

(73) Assignee: Cancer Targeted Technology LLC, Woodinville, WA (US)

( * ) Notice: Subject to any disclaimer, the term of this patent is extended or adjusted under 35 U.S.C. 154(b) by 271 days.

(21) Appl. No.: 16/316,567

(22) PCT Filed: Aug. 10, 2017

(86) PCT No.: PCT/US2017/046352
§ 371 (c)(1),
(2) Date: Jan. 9, 2019

(87) PCT Pub. No.: WO2018/031809
PCT Pub. Date: Feb. 15, 2018

(65) Prior Publication Data
US 2019/0309000 A1  Oct. 10, 2019

Related U.S. Application Data

(60) Provisional application No. 62/432,124, filed on Dec. 9, 2016, provisional application No. 62/372,871, filed on Aug. 10, 2016.

(51) Int. Cl.
| | |
|---|---|
| *A61K 51/00* | (2006.01) |
| *A61M 36/14* | (2006.01) |
| *C07F 9/6561* | (2006.01) |
| *A61K 51/04* | (2006.01) |
| *C07F 9/24* | (2006.01) |
| *C07F 9/553* | (2006.01) |
| *C07F 9/6524* | (2006.01) |

(52) U.S. Cl.
CPC ........ *C07F 9/6561* (2013.01); *A61K 51/0406* (2013.01); *A61K 51/048* (2013.01); *A61K 51/0478* (2013.01); *A61K 51/0485* (2013.01); *A61K 51/0489* (2013.01); *C07F 9/24* (2013.01); *C07F 9/5532* (2013.01); *C07F 9/6524* (2013.01)

(58) Field of Classification Search
None
See application file for complete search history.

(56) References Cited

U.S. PATENT DOCUMENTS

| | | |
|---|---|---|
| 2010/0172844 A1 | 7/2010 | Neri |
| 2013/0024494 A1 | 2/2013 | Babich et al. |
| 2017/0267717 A1 | 9/2017 | Neumaier |
| 2017/0368005 A1 | 12/2017 | Babich |
| 2018/0194729 A1 | 7/2018 | Cardinale |
| 2020/0155713 A1 | 5/2020 | Ray |

FOREIGN PATENT DOCUMENTS

| | | |
|---|---|---|
| CN | 103930432 A | 7/2014 |
| CN | 105308056 | 2/2016 |
| JP | 2014-531407 | 11/2014 |
| WO | 2012064914 | 5/2012 |
| WO | 2012/174136 | 12/2012 |
| WO | WO2012174136 | 12/2012 |
| WO | 2013/024035 | 2/2013 |

(Continued)

OTHER PUBLICATIONS

Tiancheng et al., "Spacer length effects on in vitro imaging and surface accessibility of fluorescent inhibitors of prostate specific membrane antigen," Bioorganic & Medicinal Chemistry Letters, Pergamon, Amsterdam, NL, vol. 21, No. 23, Sep. 27, 2011, pp. 7013-7016.

Fasano et al., "The extraordinary ligand binding properties of human serum albumin," IUBMB, Taylor and Francis, London, GB, vol. 57, No. 12, Dec. 1, 2005, pp. 787-796.

Elsadek et al., "Impact of albumin on drug delivery—New applications on the horizon," Journal of Controlled Release, vol. 57, No. 1, Jan. 1, 2012, pp. 4-28.

(Continued)

*Primary Examiner* — Michael G. Hartley
*Assistant Examiner* — Melissa J Perreira
(74) *Attorney, Agent, or Firm* — McDonnell Boehnen Hulbert & Berghoff LLP

(57) ABSTRACT

Provided herein are compounds of Formula (I) or a pharmaceutically acceptable salt thereof. Also provided are compositions including a compound of Formula (I) together with a pharmaceutically acceptable carrier, and methods for imaging prostate cancer cells.

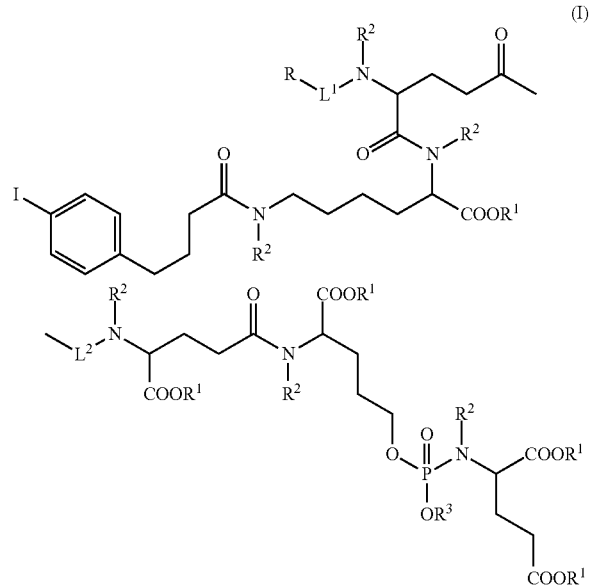

14 Claims, 6 Drawing Sheets

(56) References Cited

FOREIGN PATENT DOCUMENTS

| | | |
|---|---|---|
| WO | 2013/028664 | 2/2013 |
| WO | 2013173583 | 11/2013 |
| WO | 2015069932 | 5/2014 |
| WO | 2014/143736 | 9/2014 |
| WO | 2014143736 | 9/2014 |
| WO | 2015/073678 | 5/2015 |

OTHER PUBLICATIONS

International Search Report and Written Opinion dated Oct. 24, 2017 of PCT/US2017/046352 filed Aug. 10, 2017, 15 pages.
English translation of Chinese Office Action dated Apr. 28, 2021 for Chinese Application No. 201780049247.4, 9 pages.
English translation of Japanese Office Action dated Jul. 1, 2021 for Japanese Application No. 2019-507095, 5 pages.
Haller et al., "Folate receptor-targeted radionuclide therapy: preclinical investigation of anti-tumor effects and potential radionephropathy", Nuclear Medicine and Biology, 2015, 42(10), pp. 770-779.
English translation of Mexican Office Action dated Jan. 10, 2021 for Mexican Application No. MX/a/2019/001053, 6 pages.
Cann, Biophysical Journal, 1961, 1, p. 711-21 (Year: 1961).
Shallal et al., "Heterobivalent Agents Targeting PSMA no Integrin-[alpha] v &bgr; 3", Bioconjugate Chemistry; vol. 25, No. 2, Feb. 19, 2014, pp. 393-405.
International Search Report dated Feb. 5, 2018 for International Application No. PCT/US2017/063182 filed Nov. 24, 2017, 4 pages.

CHELATED PSMA INHIBITORS

This application is a U.S. national phase application under 35 USC 371 of International Patent Application no. PCT/US2017/046352, filed Aug. 10, 2017, which claims the benefit of priority of U.S. Provisional Patent Application No. 62/432,124, filed Dec. 9, 2016, and U.S. Provisional Patent Application No. 62/372,871, filed Aug. 10, 2016.

STATEMENT OF GOVERNMENT INTEREST

This application was supported by Contract No. HHSN261201500074C awarded by National Institutes of Health. The U.S. government has certain rights in the invention.

BACKGROUND OF THE INVENTION

Field of the Invention

The present invention relates to small molecules having high affinity and specificity to prostrate-specific membrane antigen (PSMA) and methods of using them for diagnostic and therapeutic purposes.

Summary of the Related Art

Prostate-specific membrane antigen (PSMA) is uniquely overexpressed on the surface of prostate cancer cells as well as in the neovasculature of a variety of solid tumors. As a result, PSMA has attracted attention as a clinical biomarker for detection and management of prostate cancer. Generally, these approaches utilize an antibody specifically targeted at PSMA to direct imaging or therapeutic agents. For example, ProstaScint (Cytogen, Philadelphia, Pa.), which has been approved by the FDA for the detection and imaging of prostate cancer, utilizes an antibody to deliver a chelated radioisotope (Indium-111). However, it is now recognized that the ProstaScint technology is limited to the detection of dead cells and therefore its clinical relevance is questionable.

The success of cancer diagnosis and therapy using antibodies is limited by challenges such as immunogenicity and poor vascular permeability. In addition, large antibodies bound to cell-surface targets present a barrier for subsequent binding of additional antibodies at neighboring cell-surface sites resulting in a decreased cell-surface labeling.

In addition to serving as a cell-surface target for antibodies delivering diagnostic or therapeutic agents, a largely overlooked and unique property of PSMA is its enzymatic activity. That is, PSMA is capable of recognizing and processing molecules as small as dipeptides. Despite the existence of this property, it has been largely unexplored in terms of the development of novel diagnostic and therapeutic strategies. There are a few recent examples in the literature that have described results in detecting prostate cancer cells using labeled small-molecule inhibitors of PSMA.

Certain phosphoramidate and phosphate PSMA inhibitors have been described in U.S. Pat. Nos. 7,696,185, 8,293,725, RE42,275, and in U.S. Patent Application Publication Nos. US-2014-0241985-A1 and US-2016-0030605-A1.

SUMMARY OF THE INVENTION

Provided herein are imaging diagnostics and therapeutics for prostate cancer that capitalize on the potency and specific affinity of small-molecule inhibitors to PSMA. The diagnostic agents can be used to monitor and stratify patients for treatment with appropriate therapeutic agents.

Accordingly, in one aspect the present disclosure provides compounds of Formula (I*)

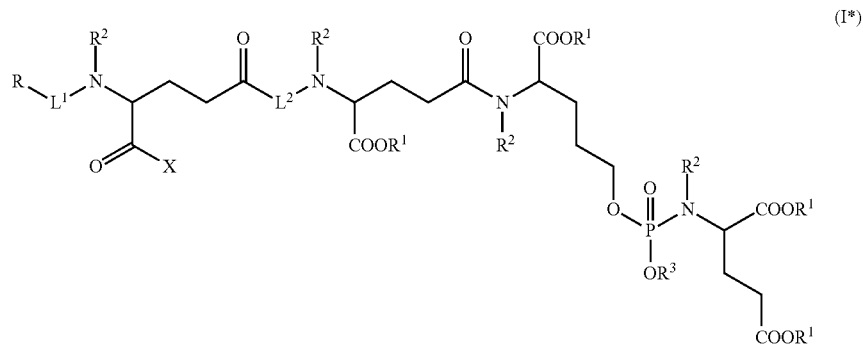

or a pharmaceutically acceptable salt thereof, wherein $L^1$ and $L^2$ are independently a divalent linking group;

R is a chelating agent optionally chelating a therapeutic radioisotope or a PET-active, SPECT-active, or MRI-active radioisotope;

each $R^1$ and $R^2$ are independently hydrogen, $C_1$-$C_6$ alkyl or a protecting group; and X is an albumin bind moiety.

In another aspect, the present disclosure provides compounds of Formula (I)

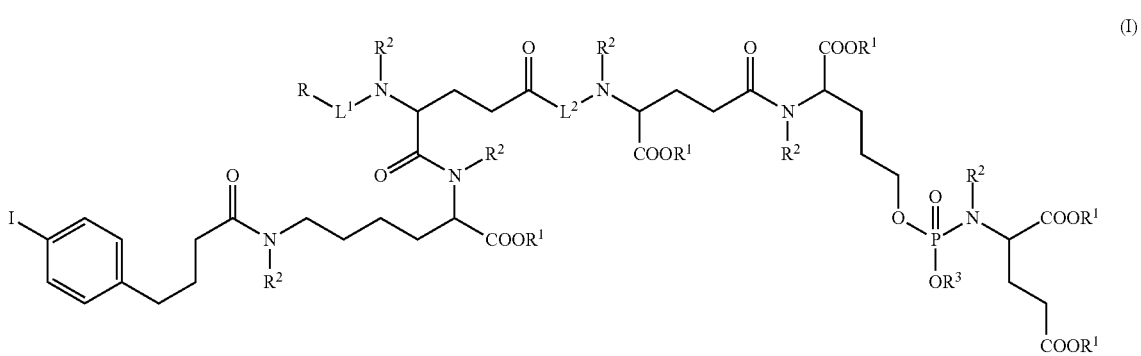

(I)

or a pharmaceutically acceptable salt thereof, wherein $L^1$ and $L^2$ are independently a divalent linking group;

R is a chelating agent optionally chelating a therapeutic radioisotope or a PET-active, SPECT-active, or MRI-active radioisotope; and each $R^1$ and $R^2$ are independently hydrogen, $C_1$-$C_6$ alkyl or a protecting group.

In another aspect the present disclosure provides pharmaceutical compositions comprising a compound of the preceding aspect and a pharmaceutically acceptable carrier.

In another aspect the present disclosure provides methods for imaging one or more prostate cancer cells or tumor-associated vasculature in a patient comprising administering to the patient a compound or a pharmaceutical composition of either of the preceding aspects.

All publicly available documents recited in this application are hereby incorporated by reference in their entirety to the extent their teachings are not inconsistent with the present disclosure.

DETAILED DESCRIPTION OF THE INVENTION

Figure 1:
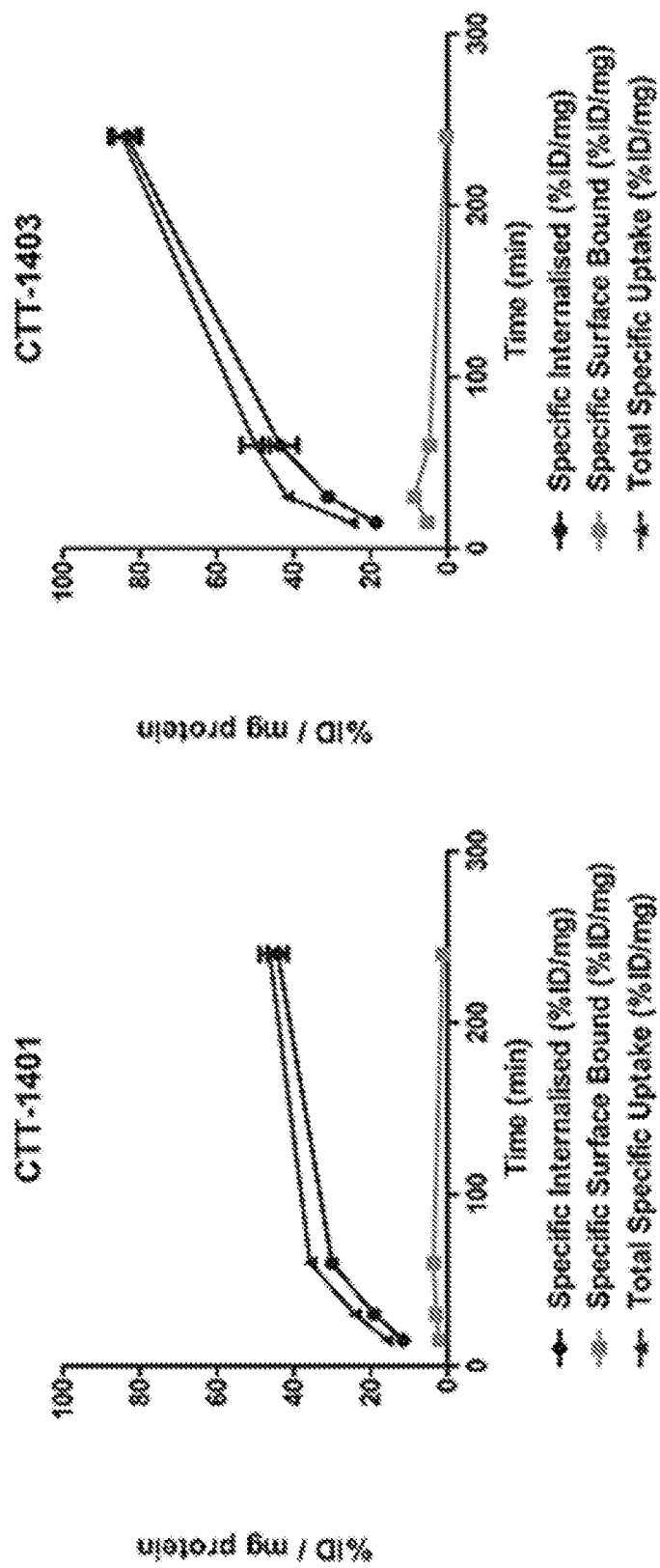
FIG. 1 is shows uptake of CTT1403 in PC3-PSMA-positive cells. Specific uptake was determined by subtracting uptake in PC3-PSMA-positive cells pre-incubated with 2-PMPA as a blocking agent from uptake in unblocked cells.

In one aspect, the present disclosure provides compounds useful as PET imaging diagnostics and radiotherapeutic agents for prostate cancer that capitalize on the potency and specific affinity of small-molecule inhibitors to PSMA.

In embodiment 1* of the first aspect, the compounds have structural Formula (I*)

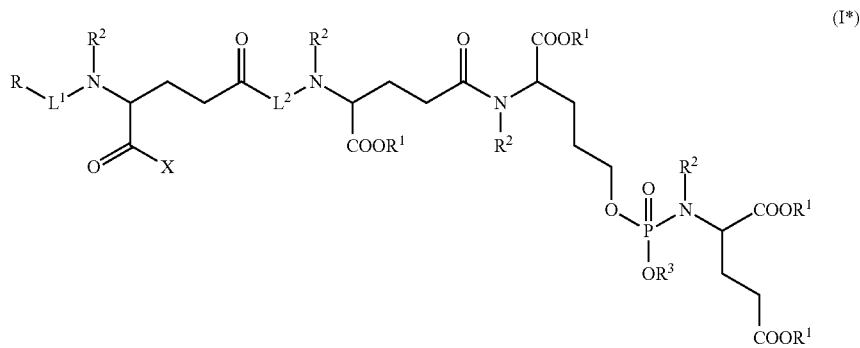

or a pharmaceutically acceptable salt thereof, wherein
$L^1$ and $L^2$ are independently a divalent linking group;
R is a chelating agent optionally chelating a therapeutic radioisotope or a PET-active, SPECT-active, or MRI-active radioisotope;
each $R^1$ and $R^2$ are independently hydrogen, $C_1$-$C_6$ alkyl or a protecting group; and
X is an albumin bind moiety.

Numerous albumin binding moieties useful in the compounds and methods of the invention are known in the art and include, for example, moieties disclosed and referred to in the following (each of which are incorporated herein by reference): Ghuman et al., "Structural Basis of the Drug-binding Specificity of Human Serum Albumin," *Journal of Molecular Biology*, 353(1), 14 Oct. 2005, 38-52; Carter, D. C. and Ho, J. X. (1994) "Structure of serum albumin," *Adv. Protein Chem.*, 45, 153-203; Curry, S. (2009) "Lessons from the crystallographic analysis of small molecule binding to human serum albumin," *Drug Metab. Pharmacokinet.*, 24, 342-357; Kratochwil, N. A. et al. (2002) "Predicting plasma protein binding of drugs: a new approach," *Biochem. Pharmacol.*, 64, 1355-1374; Zsila et al. (2011) "Evaluation of drug-human serum albumin binding interactions with support vector machine aided online automated docking," *Bioimformatics* 27(13), 1806-1813; Elsadek et al., *J Control Release.*, "Impact of albumin on drug delivery—new applications on the horizon," 2012 Jan. 10; 157(1):4-28; Nemati et al., "Assessment of Binding Affinity between Drugs and Human Serum Albumin Using Nanoporous Anodic Alumina Photonic Crystals," *Anal Chem.* 2016 Jun. 7; 88(11):5971-80; Larsen, M. T. et al., "Albumin-based drug delivery: harnessing nature to cure disease," *Mol Cell. Ther.*, 2016, Feb. 27; 4:3; Howard, K. A., "Albumin: the next-generation delivery technology," *Ther. Deliv.*, 2015, March; 6(3):265-8; Sleep D. et al., "Albumin as a versatile platform for drug half-life extension," *Biochim. Biophys. Acta.*, 2013, December; 1830(12):5526-34; Sleep, D., "Albumin and its application in drug delivery," *Expert Opin. Drug Deliv.*, 2015, May; 12(5):793-812; Qi, J et al., "Multidrug Delivery Systems Based on Human Serum Albumin for Combination Therapy with Three Anticancer Agents," *Mol. Pharm.*, 2016, Aug. 8., Article ASAP Epub ahead of print; Karimi M. et at, "Albumin nanostructures as advanced drug delivery systems," *Expert Opin. Drug Deliv.*, 2016, Jun. 3:1-15, Article ASAP Epub ahead of print; Gou, Y. et at, "Developing Anticancer Copper(II) Pro-drugs Based on the Nature of Cancer Cells and the Human Serum Albumin Carrier IIA Subdomain," *Mol. Pharm.*, 2015, Oct. 5; 12(10):3597-609; Yang, F. et al., "Interactive associations of drug-drug and drug-drug-drug with IIA subdomain of human serum albumin," *Mol. Pharm.*, 2012, Nov. 5; 9(11):3259-65; Agudelo, D. et al., "An overview on the delivery of antitumor drug doxorubicin by carrier proteins," *Int. J. Biol. Macromol.*, 2016, July; 88:354-60; Durandin, N. A. et al., "Quantitative parameters of complexes of tris(1-alkylindol-3-yl)methylium salts with serum albumin: Relevance for the design of drug candidates," *J. Photochem. Photobiol. B.*, 2016, Jul. 18; 162:570-576; Khodaei, A. et al., "Interactions Between Sirolimus and Anti-Inflammatory Drugs: Competitive Binding for Human Serum Albumin," *Adv. Pharm. Bull.*, 2016, June; 6(2):227-33; Gokara, M. et al, "Unravelling the Binding Mechanism and Protein Stability of Human Serum Albumin while Interacting with Nefopam Analogues: A Biophysical and Insilco approach," *J. Biomol. Struct. Dyn.*, 2016, July 25:1-44; Zhang, H. et al., "Affinity of miriplatin to human serum albumin and its effect on protein structure and stability," *Int. J. Biol. Macromol.*, 2016, Jul. 22; 92:593-599; Bijelic, A. et al., "X-ray Structure Analysis of Indazolium trans-[Tetrachlorobis(1H-indazole)ruthenate(III)] (KP1019) Bound to Human Serum Albumin Reveals Two Ruthenium Binding Sites and Provides Insights into the Drug Binding Mechanism," *J. Med. Chem.*, 2016, Jun. 23; 59(12):5894-903; Fasano, M. et al., "The Extraordinary Ligand Binding Properties of Human Serum Albumin," *Life*, 57(12): 787-796. Albumin binding is also utilized in many known drugs, such as warfarin, lorazepam, and ibuprofen. In some embodiments according to the invention, X is

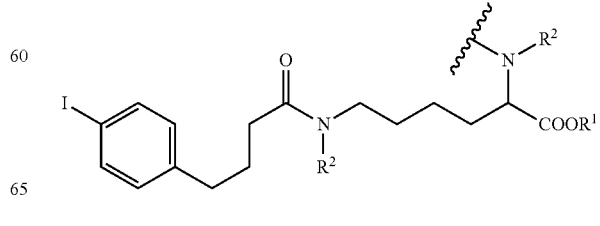

In embodiment I₁ of this first aspect, the compounds have structural formula (I):

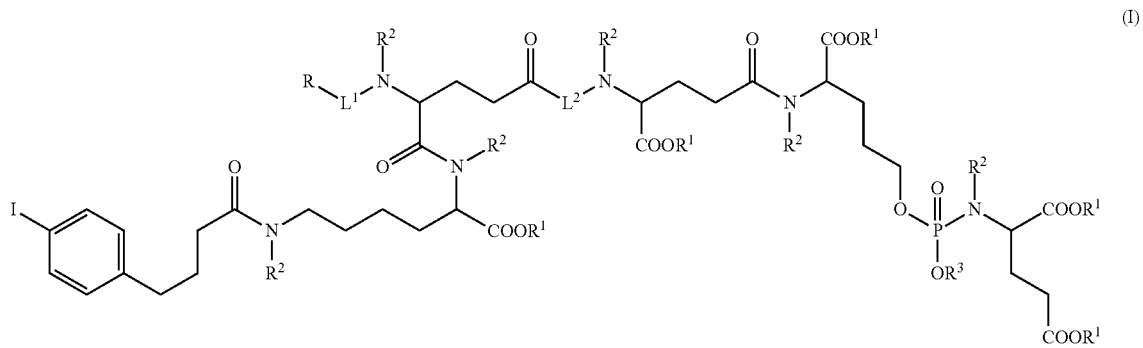

or a pharmaceutically acceptable salt thereof,
wherein
$L^1$ and $L^2$ are independently a divalent linking group;
R is a chelating agent optionally chelating a therapeutic radioisotope or a PET-active, SPECT-active, or MRI-active radioisotope; and
each $R^1$ and $R^2$ are independently hydrogen, $C_1$-$C_6$ alkyl or a protecting group.

Divalent linking groups include groups of the formula, —($C_0$-$C_{10}$ alkyl-Q)$_{0-1}$-$C_0$-$C_{10}$ alkyl-, wherein Q is a bond, aryl (e.g., phenyl), heteroaryl, $C_3$-$C_8$ cycloalkyl, or heterocyclyl; and no more than one methylene in each alkyl group is optionally and independently replaced by —O—, —S—, —N($R^{oo}$)—, —C(H)=C(H)—, —C(O)—, —S(O)—, —S(O)$_2$—, —P(O)(OR$^{oo}$)—, —OP(O)(OR$^{oo}$)—, —P(O)(OR$^{oo}$)O—, —N(R$^{oo}$)P(O)(OR$^{oo}$)—, —P(O)(OR$^{oo}$)N(R$^{oo}$)—, —OP(O)(OR$^{oo}$)O—, —OP(O)(OR$^{oo}$)N(R$^{oo}$)—, —N(R$^{oo}$)P(O)(OR$^{oo}$)O—, —N(R$^{oo}$)P(O)(OR$^{oo}$)N(R$^{oo}$)—, —C(O)O—, —C(O)N(R$^{oo}$)—, —OC(O)—, —N(R$^{oo}$)C(O)—, —S(O)O—, —OS(O)—, —S(O)N(R$^{oo}$)—, —N(R$^{oo}$)S(O)—, —S(O)$_2$O—, —OS(O)$_2$—, —S(O)$_2$N(R$^{oo}$)—, —N(R$^{oo}$)S(O)$_2$—, —OC(O)O—, —OC(O)N(R$^{oo}$)—, —N(R$^{oo}$)C(O)O—, —N(R$^{oo}$)C(O)N(R$^{oo}$)—, —OS(O)O—, —OS(O)N(R$^{oo}$)—, —N(R$^{oo}$)S(O)O—, —N(R$^{oo}$)S(O)N(R$^{oo}$)—, —OS(O)$_2$O—, —OS(O)$_2$N(R$^{oo}$)—, —N(R$^{oo}$)S(O)$_2$O—, or —N(R$^{oo}$)S(O)$_2$N(R$^{oo}$)—, wherein each $R^{oo}$ is independently hydrogen or $C_1$-$C_6$ alkyl.

In other embodiments, divalent linking groups is selected from one of the following groups of the formula, wherein in each instance, the *-end is attached to the chelating agent:
(a) *—(OCH$_2$CH$_2$)$_n$—, wherein n is 1-20 (e.g., 4-12, or 4, or 8, or 12);
(b) —(C(O)—(CH$_2$)$_{0-1}$—CH(R$^1$)N(R$^2$))$_m$—*, wherein m is 1-8;
each $R^1$ is independently the side chain of a natural or unnatural amino acid (e.g., each $R^1$ is independently hydrogen, $C_1$-$C_6$alkyl, aryl, heteroaryl, aryl$C_1$-$C_6$alkyl, or heteroaryl$C_1$-$C_6$alkyl, wherein the alkyl, arylalkyl, and heteroarylalkyl groups are optionally substituted with 1, 2, 3, 4, or 5 $R^{11}$ groups, wherein each $R^{11}$ is independently halo, cyano, —OR$^{12}$, —SR$^{12}$, —N(R$^{12}$)$_2$, —C(O)OR$^{12}$, —C(O)N(R$^{12}$)$^2$, —N(R$^{12}$)C(=NR$^{12}$)N(R$^{12}$)$_2$, or $C_1$-$C_6$alkyl, wherein each $R^{12}$ is independently hydrogen or $C_1$-$C_6$alkyl);
each $R^2$ is independently hydrogen or taken together with $R^1$ within the same residue to form a heterocyclyl (e.g., having 5-members);

(c) —(C(O)(CH$_2$)$_p$—(C(O))$_{0-1}$—NH)—*, wherein p is 1-30 (e.g., p is 1-7) (e.g., 6-aminohexanoic acid, —C(O)(CH$_2$)$_5$ NH—*);

(d) —(C(O)—(CH$_2$)$_r$-phenyl-(G)$_{0-1}$-(CH$_2$)$_q$—(C(O))$_{0-1}$—NH)—*, wherein G is —O— or —N(H)—, -r and q are each independently 0-30 (e.g., 0-20; or 0-10, or 0-6, or 1-6) (e.g., —(C(O)-phenyl-N(H)(CH$_2$)$_q$—(C(O))$_{0-1}$—NH)—*, wherein q is 1-6;

or —(C(O)—(CH$_2$)$_r$-phenyl-(CH$_2$)$_q$—NH)—*, wherein r and q are each independently 0-6;

or the two substituents on the phenyl are para to one another, such as in 4-aminomethylbenzoic acid,

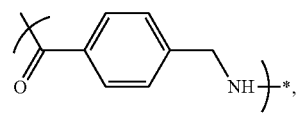

where r is 0, and q is 1; or as in 4-aminoethylbenzoic acid,

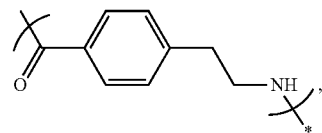

where r is 0 and q is 2); or
(e)

(e)

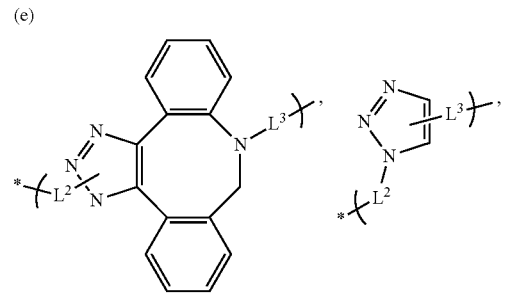

or 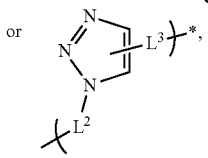

wherein
L² is —(CH₂)$_t$N(H)—*, wherein t is 1 to 30; and
L³ is #—(CH₂)$_u$—C(O)—, #—(CH₂)$_u$—Z—Y—C(O)—, #—C(O)—(CH₂)$_u$—C(O)— or #—C(O)—(CH₂)$_u$—Z—Y—C(O)—, wherein
the # end of L³ is attached to the dibenzocyclooctyne or triazolyl group above;
u is 1 to 30;
Y is —(CH₂)$_u$— or **—CH₂CH₂—(OCH₂CH₂)$_n$—, wherein
u is 1 to 30;
n is 1-20 (e.g., 4-12, or 4, or 8, or 12); and
the **-end is attached to Z; and
Z is —C(O)O—, —C(O)N(R⁰⁰)—, —OC(O)—, —N(R⁰⁰)C(O)—, —S(O)₂N(R⁰⁰)—, —N(R⁰⁰)S(O)₂—, —OC(O)O—, —OC(O)N(R⁰⁰)—, —N(R⁰⁰)C(O)O—, or —N(R⁰⁰)C(O)N(R⁰⁰)—, wherein each R⁰⁰ is independently hydrogen or C₁-C₆ alkyl;

(f) 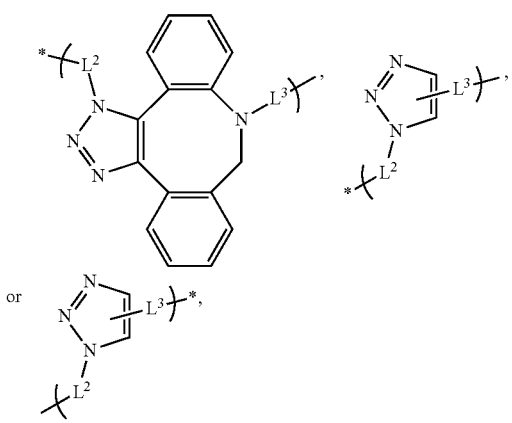

wherein
L² is —(CH₂)$_t$N(H)—*, wherein t is 1 to 30; and
L³ is #—(CH₂)$_u$—C(O)—, #—(CH₂)$_u$—Z—Y—C(O)—, #—C(O)—(CH₂)$_u$—C(O)— or #—C(O)—(CH₂)$_u$—Z—Y—C(O)—, wherein
the # end of L³ is attached to the dibenzocyclooctyne or triazolyl group above;
u is 1 to 30;
Y is —(CH₂)$_u$— or **—CH₂CH₂—(OCH₂CH₂)$_n$—, wherein
u is 1 to 30;
n is 1-20 (e.g., 4-12, or 4, or 8, or 12); and
the **-end is attached to Z; and
Z is —C(O)O—, —C(O)N(R⁰⁰)—, —OC(O)—, —N(R⁰⁰)C(O)—, —S(O)₂N(R⁰⁰)—, —N(R⁰⁰)S(O)₂—, —OC(O)O—, —OC(O)N(R⁰⁰)—, —N(R⁰⁰)C(O)O—, or —N(R⁰⁰)C(O)N(R⁰⁰)—, wherein each R⁰⁰ is independently hydrogen or C₁-C₆ alkyl;

(g) 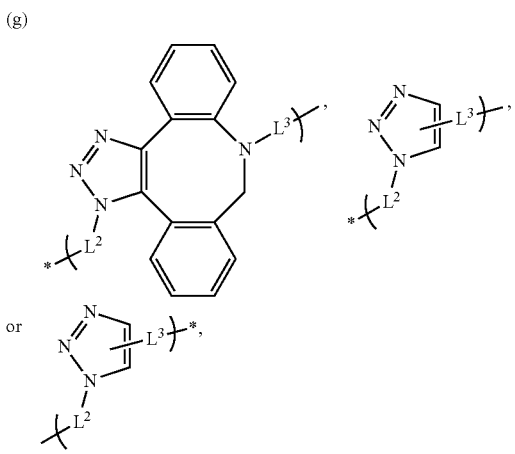

wherein
L² is —(CH₂)$_t$N(H)—*, wherein t is 1 to 30; and
L³ is #—(CH₂)$_u$—C(O)—, #—(CH₂)$_u$—Z—Y—C(O)—, #—C(O)—(CH₂)$_u$—C(O)— or #—C(O)—(CH₂)$_u$—Z—Y—C(O)—, wherein
the # end of L³ is attached to the dibenzocyclooctyne or triazolyl group above;
u is 1 to 30;
Y is —(CH₂)$_u$— or **—CH₂CH₂—(OCH₂CH₂)$_n$—, wherein
u is 1 to 30;
n is 1-20 (e.g., 4-12, or 4, or 8, or 12); and
the **-end is attached to Z; and
Z is —C(O)O—, —C(O)N(R⁰⁰)—, —OC(O)—, —N(R⁰⁰)C(O)—, —S(O)₂N(R⁰⁰)—, —N(R⁰⁰)S(O)₂—, —OC(O)O—, —OC(O)N(R⁰⁰)—, —N(R⁰⁰)C(O)O—, or —N(R⁰⁰)C(O)N(R⁰⁰)—, wherein each R⁰⁰ is independently hydrogen or C₁-C₆ alkyl;

(h) 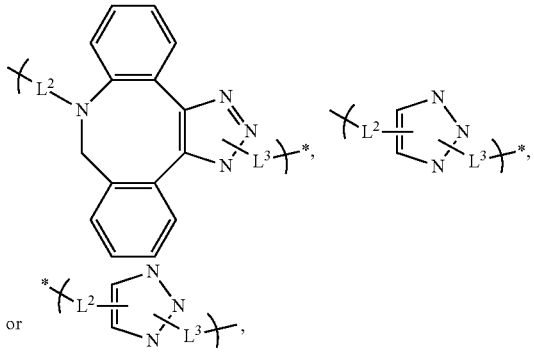

wherein
L² is —(CH₂)$_t$N(H)—*, wherein t is 1 to 30; and
L³ is #—(CH₂)$_u$—C(O)—, #—(CH₂)$_u$—Z—Y—C(O)—, #—C(O)—(CH₂)$_u$—C(O)— or #—C(O)—(CH₂)$_u$—Z—Y—C(O)—, wherein
the # end of L³ is attached to the dibenzocyclooctyne or triazolyl group above;
u is 1 to 30;
Y is —(CH₂)$_u$— or **—CH₂CH₂—(OCH₂CH₂)$_n$—, wherein
u is 1 to 30;

n is 1-20 (e.g., 4-12, or 4, or 8, or 12); and the **-end is attached to Z; and

Z is —C(O)O—, —C(O)N($R^{00}$)—, —OC(O)—, —N($R^{00}$)C(O)—, —S(O)$_2$N($R^{00}$)—, —N($R^{00}$)S(O)$_2$—, —OC(O)O—, —OC(O)N($R^{00}$)—, —N($R^{00}$)C(O)O—, or —N($R^{00}$)C(O)N($R^{00}$)—, wherein each $R^{00}$ is independently hydrogen or $C_1$-$C_6$ alkyl;

(i)

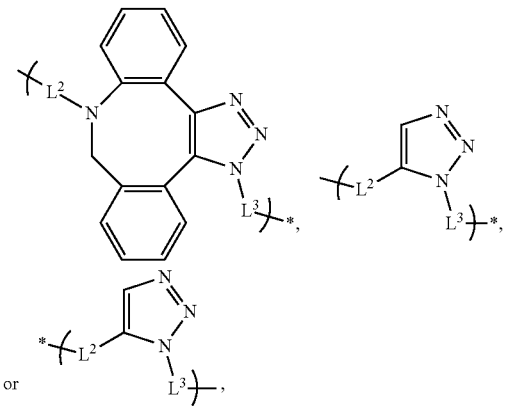

wherein $L^2$ is —(CH$_2$)$_t$N(H)—*, wherein t is 1 to 30; and $L^3$ is #—(CH$_2$)$_u$—C(O)—, #—(CH$_2$)$_u$—Z—Y—C(O)—, #—C(O)—(CH$_2$)$_u$—C(O)— or #—C(O)—(CH$_2$)$_u$—Z—Y—C(O)—, wherein the # end of $L^3$ is attached to the dibenzocyclooctyne or triazolyl group above, u is 1 to 30;

Y is —(CH$_2$)$_u$— or **—CH$_2$CH$_2$—(OCH$_2$CH$_2$)$_u$—, wherein u is 1 to 30;

n is 1-20 (e.g., 4-12, or 4, or 8, or 12); and the **-end is attached to Z; and

Z is —C(O)O—, —C(O)N($R^{00}$)—, —OC(O)—, —N($R^{00}$)C(O)—, —S(O)$_2$N($R^{00}$)—, —N($R^{00}$)S(O)$_2$—, —OC(O)O—, —OC(O)N($R^{00}$)—, —N($R^{00}$)C(O)O—, or —N($R^{00}$)C(O)N($R^{00}$)—, wherein each $R^{00}$ is independently hydrogen or $C_1$-$C_6$ alkyl;

(j)

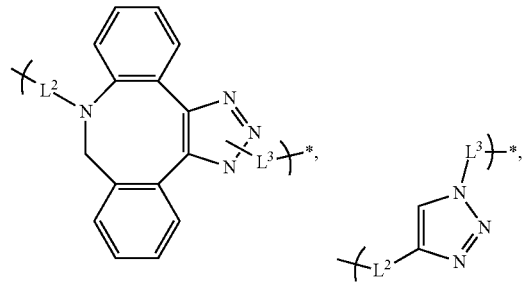

or 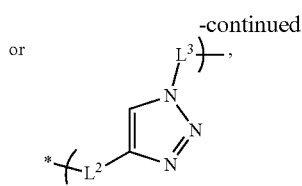, wherein $L^2$ is —(CH$_2$)$_t$N(H)—*, wherein t is 1 to 30; and $L^3$ is #—(CH$_2$)$_u$—C(O)—, #—(CH$_2$)$_u$—Z—Y—C(O)—, #—C(O)—(CH$_2$)$_u$—C(O)— or #—C(O)—(CH$_2$)$_u$—Z—Y—C(O)—, wherein the # end of $L^3$ is attached to the dibenzocyclooctyne or triazolyl group above;

u is 1 to 30;

Y is —(CH$_2$)$_u$— or **—CH$_2$CH$_2$—(OCH$_2$CH$_2$)$_u$—, wherein u is 1 to 30;

n is 1-20 (e.g., 4-12, or 4, or 8, or 12); and the **-end is attached to Z; and

Z is —C(O)O—, —C(O)N($R^{00}$)—, —OC(O)—, —N($R^{00}$)C(O)—, —S(O)$_2$N($R^{00}$)—, —N($R^{00}$)S(O)$_2$—, —OC(O)O—, —OC(O)N($R^{00}$)—, —N($R^{00}$)C(O)O—, or —N($R^{00}$)C(O)N($R^{00}$)—, wherein each $R^{00}$ is independently hydrogen or $C_1$-$C_6$ alkyl;

and (k) combinations of the preceding, wherein in each instance, the *-end is attached to the chelating agent, such as:

(i) —(CH$_2$CH$_2$O)$_n$—(C(O)(CH$_2$)$_p$—(C(O))$_{0-1}$—NH)—*, where n and p are as defined above (e.g., n is 4 and p is 6);

(ii) —(CH$_2$CH$_2$O)$_n$—(C(O)—(CH$_2$)$_{0-1}$—CH($R^1$)N($R^2$))$_m$—*, where $R^1$, $R^2$, n and m are as defined above (e.g., n is 4 and m is 2);

(iii) —(CH$_2$CH$_2$O)$_n$—(C(O)—(CH$_2$)$_r$-phenyl-(G)$_{0-1}$-(CH$_2$)$_q$—(C(O))$_{0-1}$—NH)—*, where G, n, q, and r are as defined above (e.g., n is 4, q is 1, and r is 0);

(iv) —(C(O)—(CH$_2$)$_{0-1}$—CH($R^1$)N($R^2$))$_m$—(C(O)(CH$_2$)$_p$—(C(O))$_{0-1}$—NH)—*, where $R^1$, $R^2$, m and p are as defined above (e.g., m is 2 and p is 6);

(v) —(C(O)—(CH$_2$)$_{0-1}$—CH($R^1$)N($R^2$))$_m$—(C(O)—(CH$_2$)$_r$-phenyl-(G)$_{0-1}$-(CH$_2$)$_q$—(C(O))$_{0-1}$—NH)—*, where G, $R^1$, $R^2$, m, q, and r are as defined above (e.g., m is 2, q is 1, and r is 0; or m is 2, q is 2, and r is 0);

(vi) —(C(O)(CH$_2$)$_p$—(C(O))$_{0-1}$—NH)—(C(O)—(CH$_2$)$_r$-phenyl-(G)$_{0-1}$-(CH$_2$)$_q$—(C(O))$_{0-1}$—NH)—*, where G, p, q, and r are as defined above (e.g., p is 6, q is 1, and r is 0; p is 6, q is 2, and r is 0; p is 5, q is 1, and r is 0; or p is 5, q is 2, and r is 0);

(vii) —(C(O)(CH$_2$)$_p$—(C(O))$_{0-1}$—NH)—(C(O)—(CH$_2$)$_{0-1}$—CH($R^1$)N($R^2$))$_m$—*, where $R^1$, $R^2$, m and p are as defined above (e.g., m is 2 and p is 6);

(viii) —(C(O)—(CH$_2$)$_r$-phenyl-(G)$_{0-1}$-(CH$_2$)$_q$—(C(O))$_{0-1}$—NH)—(C(O)—(CH$_2$)$_{0-1}$—CH($R^1$)N($R^2$))$_m$—*, where G, $R^1$, $R^2$, m, q, and r are as defined above (e.g., m is 2, q is 1, and r is 0; or m is 2, q is 2, and r is 0);

(ix) —(C(O)—(CH$_2$)$_r$-phenyl-(G)$_{0-1}$-(CH$_2$)$_q$—(C(O))$_{0-1}$—NH)—(C(O)(CH$_2$)$_p$—(C(O))$_{0-1}$—NH)—*, where G, p, q, and r are as defined above (e.g., p is 6, q is 1, and r is 0; p is 6, q is 2, and r is 0; p is 5, q is 1, and r is 0; or p is 5, q is 2, and r is 0);

(x) —(C(O)(CH$_2$)$_p$—(C(O))$_{0-1}$—NH)—(CH$_2$CH$_2$O)$_n$—*, where n and p are as defined above (e.g., n is 4 and p is 6);

(xi) —(C(O)—(CH$_2$)$_{0-1}$—CH(R$^1$)N(R$^2$))$_m$—(CH$_2$CH$_2$O)$_n$—*, where R$^1$, R$^2$, n and m are as defined above (e.g., n is 4 and m is 2); and (xii) —(C(O)—(CH$_2$)$_r$-phenyl-(G)$_{0-1}$-(CH$_2$)$_q$—(C(O))$_{0-1}$—NH)—(CH$_2$CH$_2$O)$_n$—*, where G, n, q, and r are as defined above (e.g., n is 4, q is 1, and r is 0; n is 4, q is 2, and r is 0);

(xiii) —(C(O)(CH$_2$)$_p$N(H)C(O)(CH$_2$)$_p$NH—)*, where each p is independently as defined above (e.g., each p is 5, —C(O)(CH$_2$)$_5$NH—C(O)(CH$_2$)$_5$NH—*);

(xiv) a covalent bond.

In other embodiments, divalent linking groups is selected from one of the following groups of the formula, wherein in each instance, the *-end is attached to the chelating agent:

(xv) —(C(O)(CH$_2$)$_p$—(C(O))$_{0-1}$—NH)—*, wherein p is 1-7, (e.g., 6-aminohexanoic acid, —C(O)(CH$_2$)$_5$NH—*);

(xvi) —(C(O)—(CH$_2$)$_r$-phenyl-(G)$_{0-1}$-(CH$_2$)$_q$—(C(O))$_{0-1}$—NH)—*, wherein G is —N(H)—, r is 0-6 (e.g., 0-3, or 0-2, or 0, or 1, or 2, or 1-6), q is 1-6 (e.g., 1-3, or 1-2, or 1, or 2) (e.g., the two substituents on the phenyl are para to one another, such as in 4-aminomethylbenzoic acid,

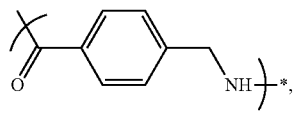

where r is 0 and q is 1; or as in 4-aminoethylbenzoic acid,

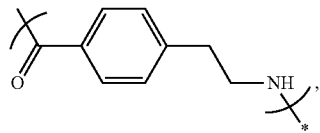

where r is 0 and q is 2); or (xvii) —(C(O)(CH$_2$)$_p$—(C(O))$_{0-1}$—NH)—(C(O)—(CH$_2$)$_r$-phenyl-(G)$_{0-1}$-(CH$_2$)$_q$—(C(O))$_{0-1}$—NH)—*, where G, p, q, and r are as defined above (e.g., p is 6, q is 1, and r is 0; p is 6, q is 2, and r is 0; p is 5, q is 1, and r is 0; or p is 5, q is 2, and r is 0);

(xviii) —(C(O)—(CH$_2$)$_r$-phenyl-(G)$_{0-1}$-(CH$_2$)$_q$—(C(O))$_{0-1}$—NH)—(C(O)(CH$_2$)$_p$—(C(O))$_{0-1}$—NH)—*, where G, p, q, and r are as defined above (e.g., p is 6, q is 1, and r is 0; p is 6, q is 2, and r is 0; p is 5, q is 1, and r is 0; or p is 5, q is 2, and r is 0);

(xix) —(C(O)(CH$_2$)$_p$N(H)C(O)(CH$_2$)$_p$NH—)*, where each p is independently as defined above (e.g., each p is 5, —C(O)(CH$_2$)$_5$NH—C(O)(CH$_2$)$_5$NH—);

(xx) a covalent bond.

In other embodiments, divalent linking groups is selected from one of the following groups of the formula, wherein in each instance, the *-end is attached to the chelating agent:

(xxi) —(C(O)(CH$_2$)$_p$—(C(O))$_{0-1}$—NH)—*, wherein p is 4-6, (e.g., 6-aminohexanoic acid, —C(O)(CH$_2$)$_5$NH—*);

(xxii) —(C(O)—(CH$_2$)$_r$-phenyl-(G)$_{0-1}$-(CH$_2$)$_q$—(C(O))$_{0-1}$—NH)—*, wherein G is —N(H)—, r is 0-6 and q is 1-3 (e.g., the two substituents on the phenyl are para to one another, such as in 4-aminomethylbenzoic acid,

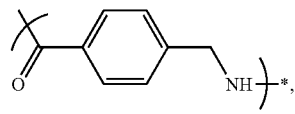

where q is 1; or as in 4-aminoethylbenzoic acid,

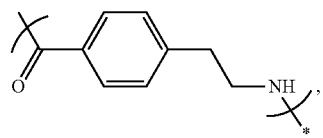

where q is 2); or (xxiii) —(C(O)(CH$_2$)$_p$—(C(O))$_{0-1}$—NH)—(C(O)—(CH$_2$)$_r$-phenyl-(G)$_{0-1}$-(CH$_2$)$_q$—(C(O))$_{0-1}$—NH)—*, where p, q, and r are as defined above (e.g., p is 6, q is 1, and r is 0; p is 6, q is 2, or r is 0; p is 5, q is 1, and r is 0; or p is 5, q is 2, and r is 0);

(xxiv) —(C(O)—(CH$_2$)$_r$-phenyl-(G)$_{0-1}$-(CH$_2$)$_q$—(C(O))$_{0-1}$—NH)—(C(O)(CH$_2$)$_p$—(C(O))$_{0-1}$—NH)—*, where G, p, q, and r are as defined above (e.g., p is 6, q is 1, and r is 0; p is 6, q is 2, and r is 0; p is 5, q is 1, and r is 0; or p is 5, q is 2, and r is 0);

(xxv) —(C(O)(CH$_2$)$_p$N(H)C(O)(CH$_2$)$_p$NH—)*, where each p is independently as defined above (e.g., each p is 5, —C(O)(CH$_2$)$_5$NH—C(O)(CH$_2$)$_5$NH—*);

(xxvi) a covalent bond.

In other embodiments, divalent linking groups is selected from one of the following groups of the formula, wherein in each instance, the *-end is attached to the chelating agent:

(i) —C(O)(CH$_2$)$_5$NH—*;

(ii) 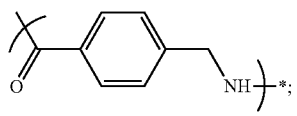

(iii) 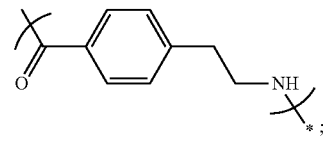

(iv) 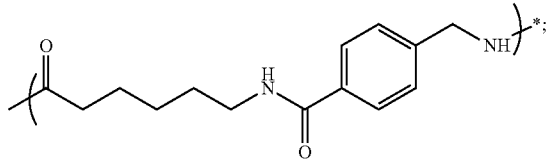

(v) 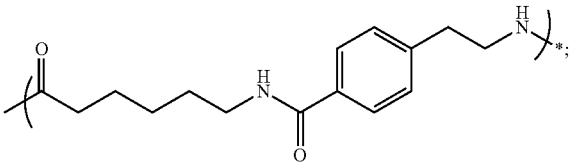

(vi) —C(O)(CH$_2$)$_5$NH—C(O)(CH$_2$)$_5$NH—*;
(vii) C$_1$-C$_6$alkyl;
(viii) C$_1$-C$_6$alkyl-NH—;
(ix) a covalent bond.

In embodiment I$_2$, the compounds are of embodiment I$_1$, wherein
L$^1$ is a moiety of the formula L$^{1A}$-NH—CH$_2$CH$_2$—(OCH$_2$CH$_2$—)$_y$—C(O)—, wherein
y is 1, 2, 3, 4, 5, 6, 7, 8, 9, 10, 11 or 12; and
L$^{1A}$ is a divalent linking group.

In embodiment I$_{2a}$, the compounds are of embodiment I$_2$ wherein y is selected from one of the following groups (1a)-(1x):

| (1a) | 1, 2, 3, 4, 5, 6, 7, 8, 9, 10, 11, or 12. | (1b) | 1, 2, 3, 4, 5, 6, 7, 8, 9 or 10. |
|---|---|---|---|
| (1c) | 1, 2, 3, 4, 5, 6, 7 or 8. | (1d) | 1, 2, 3, 4, 5 or 6. |
| (1e) | 1, 2, 3 or 4. | (1f) | 1 or 2. |
| (1g) | 6, 7, 8, 9, 10, 11 or 12. | (1h) | 6, 7, 8, 9 or 10. |
| (1i) | 3, 4, 5, 6, 7 or 8. | (1j) | 2, 4, 6, 8, 10 or 12. |
| (1k) | 2, 4, 6 or 8. | (1l) | 1, 3, 5, 7, 9 or 11. |
| (1m) | 1. | (1n) | 2. |
| (1o) | 3. | (1p) | 4. |
| (1q) | 5. | (1r) | 6. |
| (1s) | 7. | (1t) | 8. |
| (1u) | 9. | (1v) | 10. |
| (1w) | 11. | (1x) | 12. |

In embodiment I$_3$, the compounds are of embodiment I$_1$ or I$_2$, wherein
L$^2$ is a group of the formula

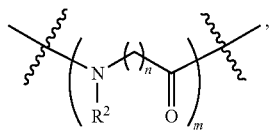

wherein
m is 1, 2, 3, or 4;
each n is independently 1, 2, 3, 4, 5, 6, 7, 8, 9, 10, 11 or 12;
provided that m·(n+2) is greater than or equal to 3 and less than or equal to 21.

In embodiment I$_{3a}$, the compounds are of embodiment I$_3$ wherein m is selected from one of the following groups (2a)-(2o):

| (2a) | 1, 2, 3 or 4. | (2b) | 1, 2 or 3. | (2c) | 1 or 2. | (2d) | 1. | (2e) | 2, 3 or 4. |
|---|---|---|---|---|---|---|---|---|---|
| (2f) | 1 or 3. | (2g) | 2 or 4. | (2h) | 1 or 2. | (2i) | 2 or 3. | (2j) | 3 or 4. |
| (2k) | 1 or 4. | (2l) | 1. | (2m) | 2. | (2n) | 3. | (2o) | 4. |

In embodiment I$_{3b}$, the compounds are of embodiment I$_3$ or I$_{3a}$ wherein each n is independently selected from one of the following groups (3a)-(3x):

| (3a) | 1, 2, 3, 4, 5, 6, 7, 8, 9, 10, 11 or 12. | (3b) | 1, 2, 3, 4, 5, 6, 7, 8, 9 or 10. |
|---|---|---|---|
| (3c) | 1, 2, 3, 4, 5, 6, 7 or 8. | (3d) | 1, 2, 3, 4, 5 or 6. |
| (3e) | 1, 2, 3 or 4. | (3f) | 1 or 2. |
| (3g) | 6, 7, 8, 9, 10, 11 or 12. | (3h) | 6, 7, 8, 9 or 10. |
| (3i) | 3, 4, 5, 6, 7 or 8. | (3j) | 2, 4, 6, 8, 10 or 12. |
| (3k) | 2, 4, 6 or 8. | (3l) | 1, 3, 5, 7, 9 or 11. |
| (3m) | 1. | (3n) | 2. |
| (3o) | 3. | (3p) | 4. |
| (3q) | 5. | (3r) | 6. |
| (3s) | 7. | (3t) | 8. |
| (3u) | 9. | (3v) | 10. |
| (3w) | 11. | (3x) | 12. |

In embodiment I$_4$, the compounds are of any of embodiments I$_1$-I$_3$ wherein the compound has the structure of Formula I*:

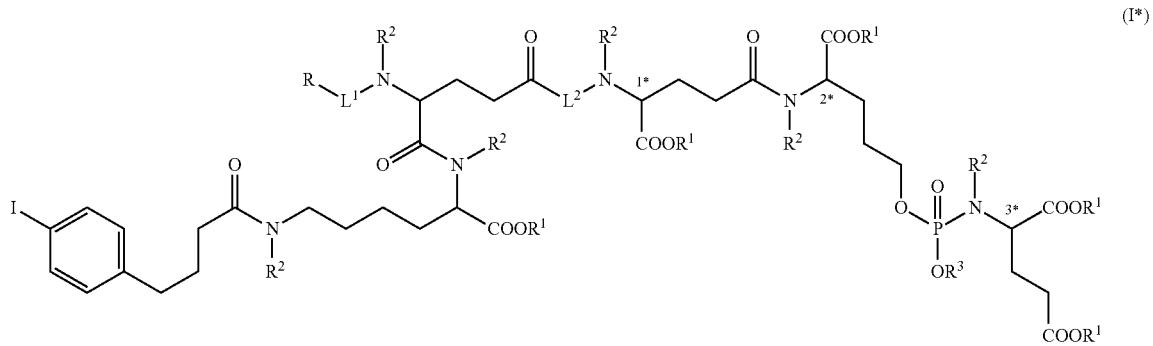

(I*)

or a pharmaceutically acceptable salt thereof, wherein $L^1$, $L^2$, R, $R^1$ and $R^2$ are as described herein.

In Formula (I*), 1*, 2*, and 3* are chiral centers that are independently racemic (rac) or in the S or R stereoconfiguration. Thus, compounds according to this aspect include those with the following combinations of stereoconfigurations, and mixtures thereof:

| 1* | 2* | 3* | 1* | 2* | 3* | 1* | 2* | 3* | 1* | 2* | 3* | 1* | 2* | 3* |
|----|----|----|----|----|----|----|----|----|----|----|----|----|----|----|
| S  | S  | S  | R  | S  | S  | R  | R  | S  | rac| S  | R  | S  | rac| S  |
| S  | S  | R  | S  | R  | R  | R  | R  | R  | rac| R  | S  | S  | rac| R  |
| S  | R  | S  | R  | S  | R  | rac| S  | S  | rac| R  | R  | R  | rac| S  |
| R  | rac| R  | S  | S  | rac| S  | R  | rac| R  | S  | rac| R  | R  | rac|

In embodiment $I_5$, the compounds of embodiment $I_1$ have the structure of Formula (Ia):

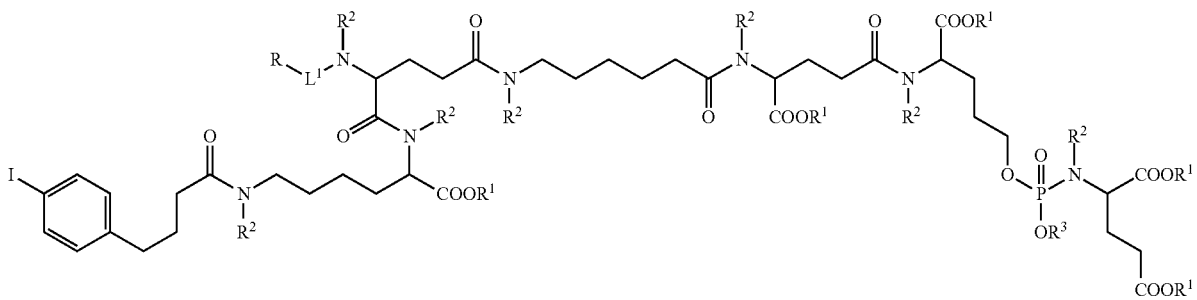

(Ia)

or a pharmaceutically acceptable salt thereof, wherein $L^1$, R, $R^1$ and $R^2$ are as described herein.

In embodiment $I_6$, the compounds of embodiment $I_1$ have the structure of Formula (Ib):

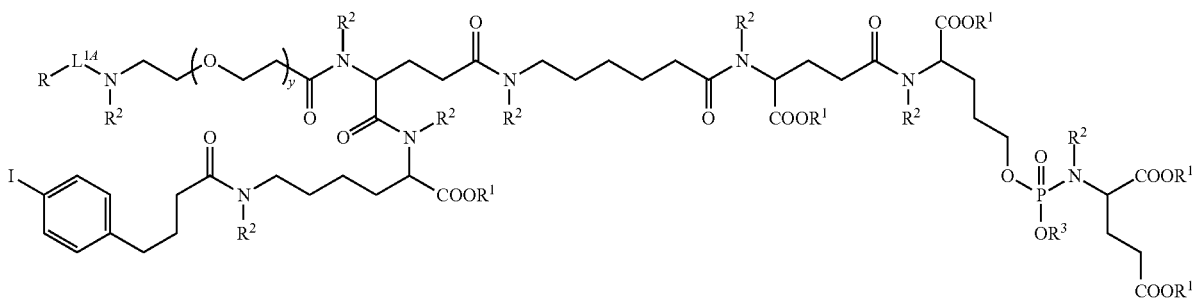

(Ib)

or a pharmaceutically acceptable salt thereof, wherein
y is 2, 3, 4, 5 or 6;
$L^{1A}$ is a divalent linker; and
R, $R^1$ and $R^2$ are as described herein.

In embodiment $I_{6a}$, the compounds are of embodiment $I_1$ having the structure of Formula (Ib), or the compounds are of embodiment $I_2$, wherein $L^{1A}$ is:

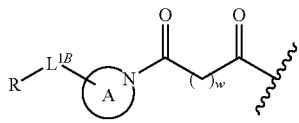

wherein
w is 1, 2, 3, 4, 5 or 6;
ring A is heterocyclic;
and $L^{1B}$ is a divalent linker.

In embodiment $I_{6b}$, the compounds are of embodiment $I_{6a}$ wherein $L^{1B}$ is: $C_1$-$C_6$alkyl-NH—.

In embodiment $I_{6c}$, the compounds are of embodiment $I_1$ having the structure of Formula (Ib), or the compounds are of embodiment $I_2$, wherein $L^{1A}$ is:

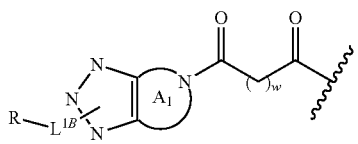

wherein
w is 1, 2, 3, 4, 5 or 6;
ring $A_1$ is heterocyclic; and
$L^{1B}$ is a divalent linker.

In embodiment $I_{6d}$, the compounds are of embodiment $I_{6a}$ wherein $L^{1B}$ is: $C_1$-$C_6$alkyl-NH—.

In embodiment $I_{6e}$, the compounds are of embodiment $I_1$ having the structure of Formula (Ib), or the compounds are of embodiment $I_2$, wherein $L^{1A}$ is:

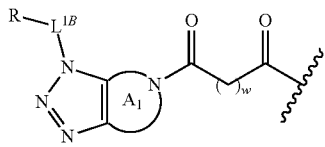

wherein
w is 1, 2, 3, 4, 5 or 6;
ring $A_1$ is heterocyclic; and
$L^{1B}$ is a divalent linker.

In embodiment $I_{6f}$, the compounds are of embodiment $I_{6a}$ wherein $L^{1B}$ is: $C_1$-$C_6$alkyl-NH—.

In embodiment $I_{6g}$, the compounds are of embodiment $I_1$ having the structure of Formula (Ib), or the compounds are of embodiment $I_2$, wherein $L^{1A}$ is:

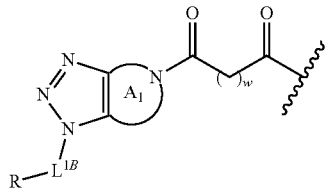

wherein
w is 1, 2, 3, 4, 5 or 6;
ring $A_1$ is heterocyclic; and
$L^{1B}$ is a divalent linker.

In embodiment $I_{6h}$, the compounds are of embodiment $I_{6a}$ wherein $L^{1B}$ is: $C_1$-$C_6$alkyl-NH—.

In embodiment $I_{6i}$, the compounds are of embodiment $I_1$ having the structure of Formula (Ib), or the compounds are of embodiment $I_2$, wherein $L^{1A}$ is:

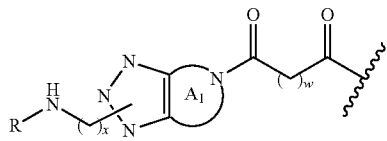

wherein
x is 0, 1, 2, 3, 4, 5 or 6;
w is 1, 2, 3, 4, 5 or 6; and
ring $A_1$ is heterocyclic.

In embodiment $I_{6j}$, the compounds are of embodiment $I_1$ having the structure of Formula (Ib), or the compounds are of embodiment $I_2$, wherein $L^{1A}$ is:

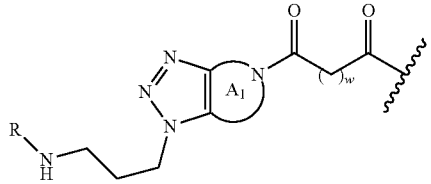

wherein
w is 1, 2, 3, 4, 5 or 6; and
ring $A_1$ is heterocyclic.

In embodiment $I_{6k}$, the compounds are of embodiment $I_1$ having the structure of Formula (Ib), or the compounds are of embodiment $I_2$, wherein $L^{1A}$ is:

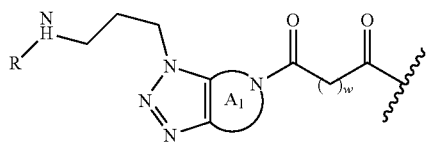

wherein
w is 1, 2, 3, 4, 5 or 6; and
ring $A_1$ is heterocyclic.

In embodiment $I_{6l}$, the compounds are of any of embodiments 16a-16e, wherein w is selected from one of the following groups (4a)-(4p):

| | | | |
|---|---|---|---|
| (4a) | 1, 2, 3, 4, 5 or 6. | (4b) | 1, 2, 3, 4 or 5. |
| (4c) | 1, 2, 3 or 4. | (4d) | 1, 2 or 3. |
| (4e) | 1 or 2. | (4f) | 2, 3, 4, 5 or 6. |
| (4g) | 2, 3, 4 or 5. | (4h) | 2, 3 or 4. |
| (4i) | 2 or 3 | (4j) | 3 or 4. |
| (4k) | 1. | (4l) | 2. |
| (4m) | 3. | (4n) | 4. |
| (4o) | 5. | (4p) | 6. |

In embodiment I$_{6m}$, the compounds are of embodiment I$_1$ having the structure of Formula (Ib), or the compounds are of embodiment I$_2$, wherein L$^{1A}$ is:

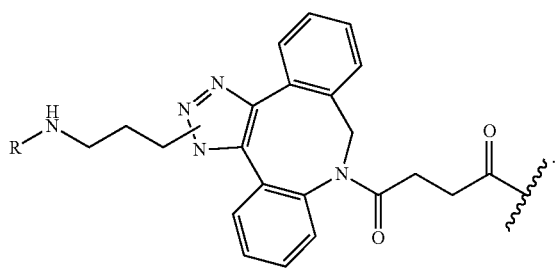

In embodiment I$_{6n}$, the compounds are of embodiment I$_1$ having the structure of Formula (Ib), or the compounds are of embodiment I$_2$, wherein L$^{1A}$ is:

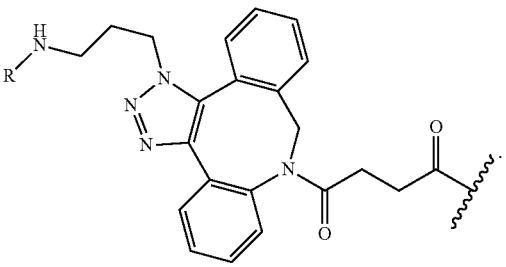

In embodiment I$_{6o}$, the compounds are of embodiment I$_1$ having the structure of Formula (Ib), or the compounds are of embodiment I$_2$, wherein L$^{1A}$ is:

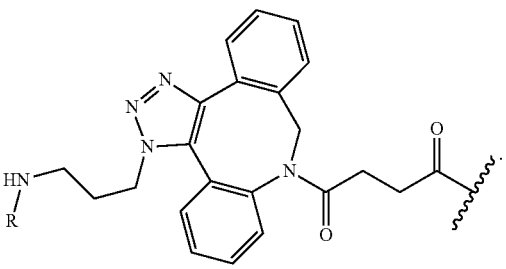

In embodiment I$_7$, the compounds of embodiment I$_1$ have the structure of Formula (Ic):

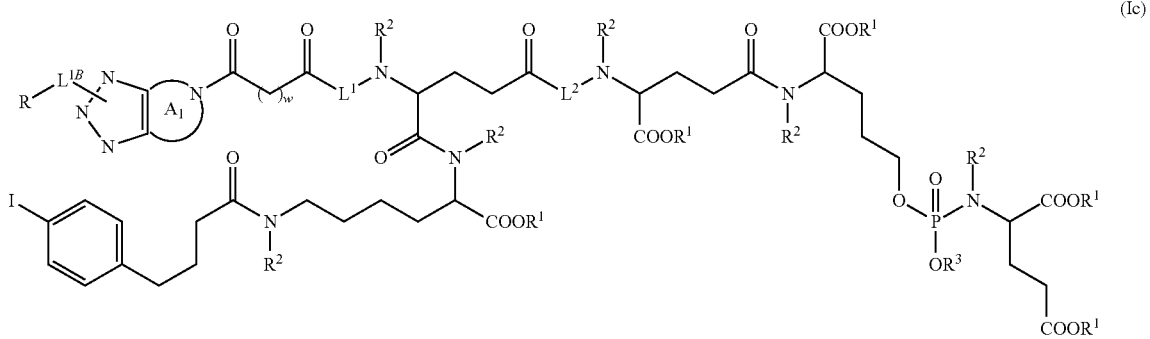

(Ic)

wherein
w is 1, 2, 3, 4, 5 or 6;
ring A$_1$ is heterocyclic; and
L$^{1B}$ is a divalent linker.

In embodiment I$_8$, the compounds of embodiment I$_1$ have the structure of Formula (Ic'):

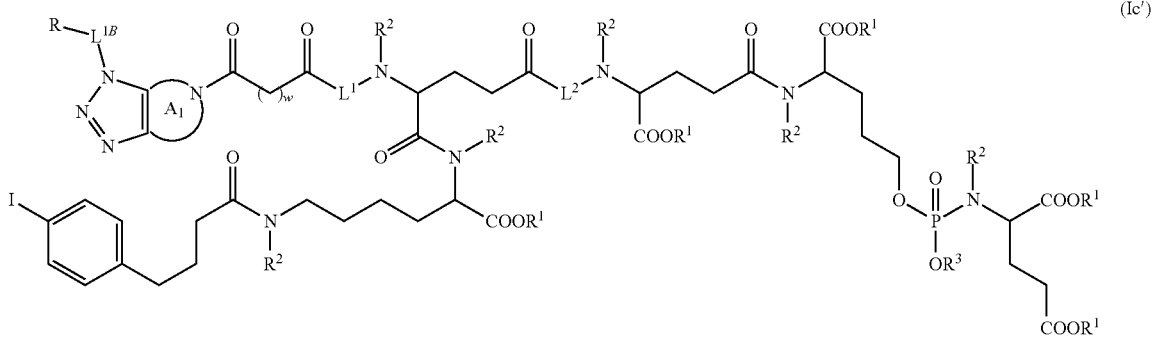

(Ic')

wherein
w is 1, 2, 3, 4, 5 or 6;
ring $A_1$ is heterocyclic; and
$L^{1B}$ is a divalent linker.
In embodiment $I_9$, the compounds of embodiment $I_1$ have the structure of Formula (Ic):
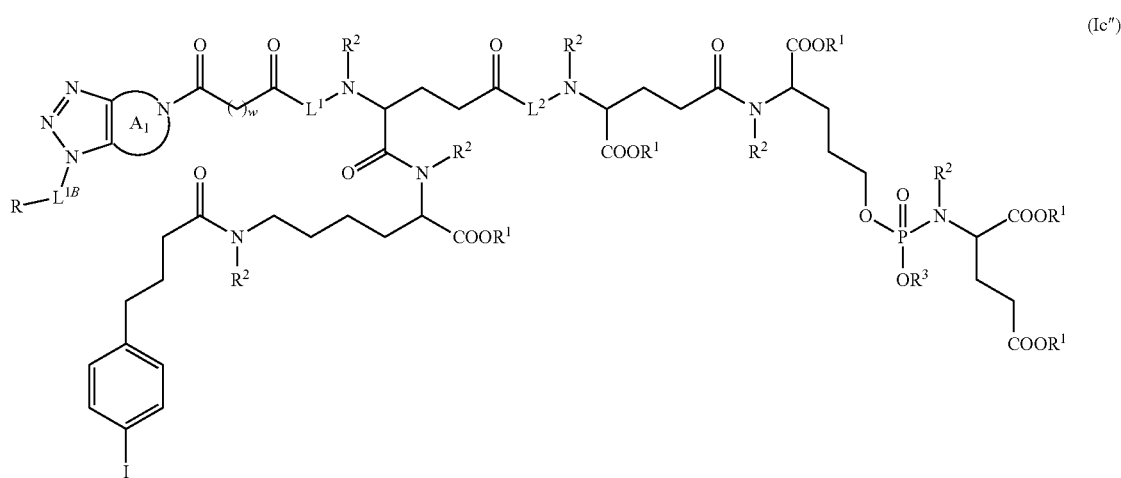
(Ic″)
wherein
w is 1, 2, 3, 4, 5 or 6;
ring $A_1$ is heterocyclic; and
$L^{1B}$ is a divalent linker.
In embodiment $I_{10}$, the compounds of embodiment $I_1$ have the structure of Formula (Id):
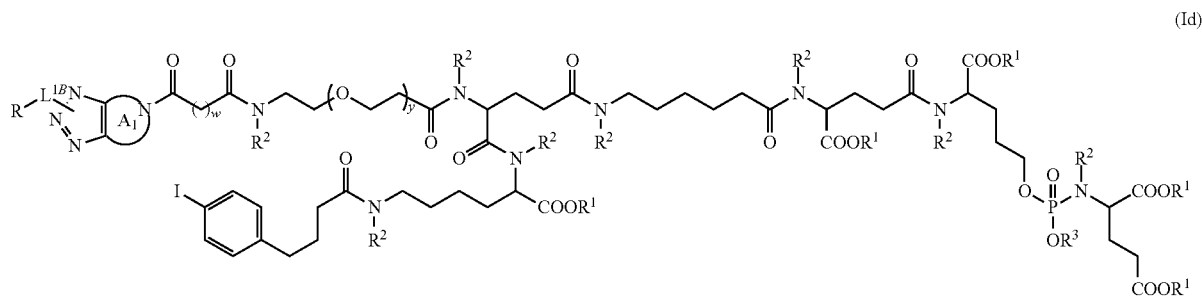
(Id)

wherein
y is 2, 3, 4, 5 or 6;
w is 1, 2, 3, 4, 5 or 6;
ring $A_1$ is heterocyclic; and
$L^{1B}$ is a divalent linker.

In embodiment $I_{11}$, the compounds of embodiment $I_1$ have the structure of Formula (Id'):

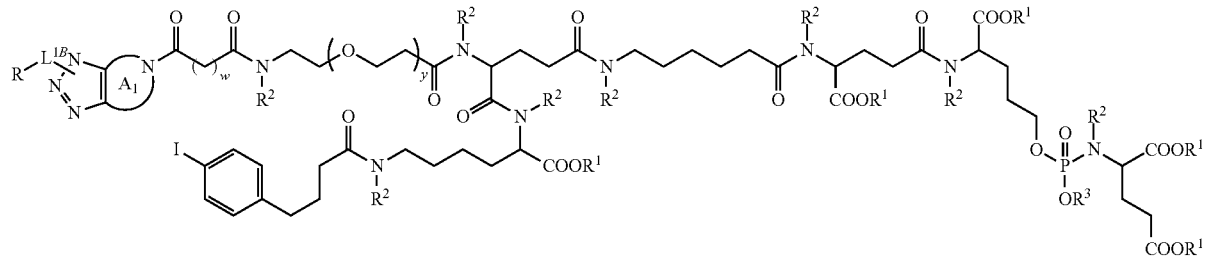

(Id')

wherein
y is 2, 3, 4, 5 or 6;
w is 1, 2, 3, 4, 5 or 6;
ring $A_1$ is heterocyclic; and
$L^{1B}$ is a divalent linker.

In embodiment $I_{12}$, the compounds of embodiment $I_1$ have the structure of Formula (Id"):

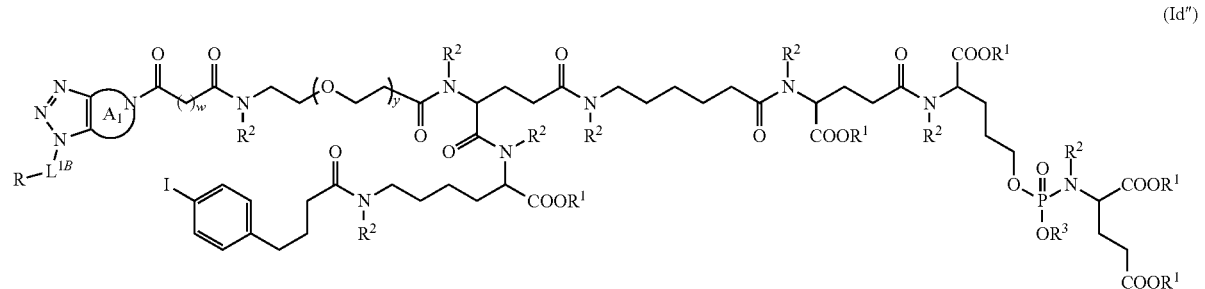

(Id")

wherein
y is 2, 3, 4, 5 or 6;
w is 1, 2, 3, 4, 5 or 6;
ring $A_1$ is heterocyclic; and
$L^{1B}$ is a divalent linker.

In embodiment $I_{13}$, the compounds of embodiment $I_1$ have the structure of Formula (Ie):

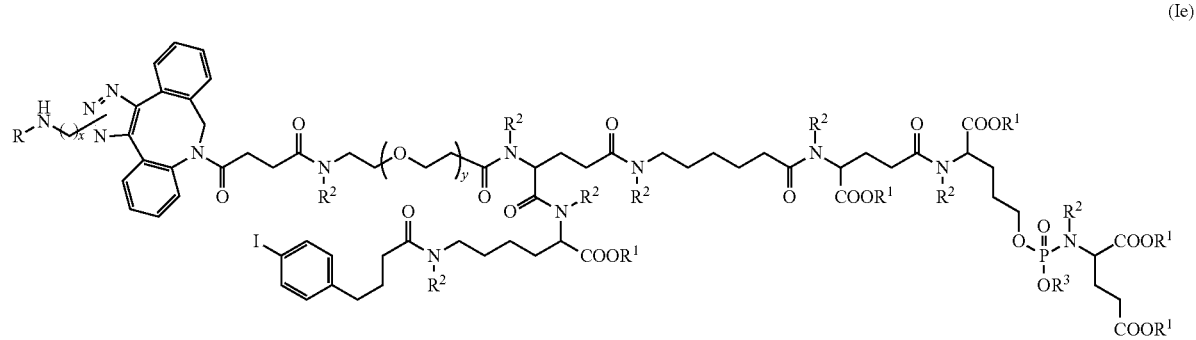

(Ie)

wherein
x is 0, 1, 2, 3, 4, 5 or 6; and
y is 2, 3, 4, 5 or 6.

In embodiment I$_{13'}$, the compounds of embodiment I$_1$ have the structure of Formula (Ie) wherein x is 3.

In embodiment I$_{14}$, the compounds of embodiment I$_1$ have the structure of Formula (If):

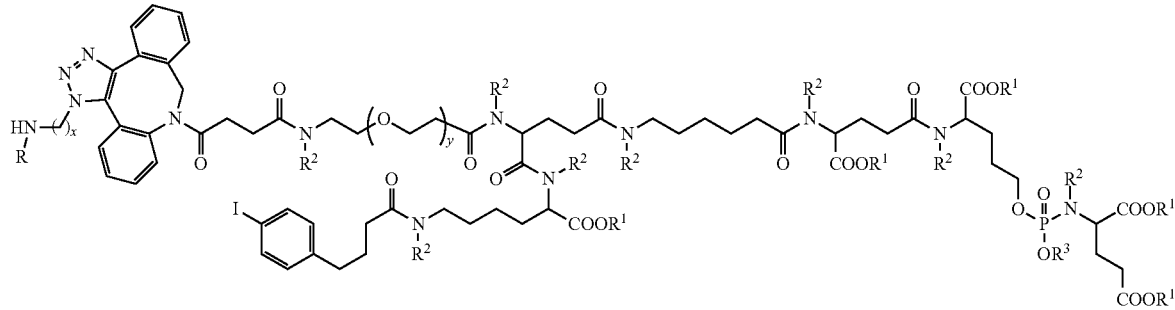

(If)

wherein y is 2, 3, 4, 5 or 6.

In embodiment I$_{14'}$, the compounds of embodiment I$_1$ have the structure of Formula (If) wherein x is 3.

In embodiment I$_{15}$, the compounds of embodiment I$_1$ have the structure of Formula (Ig):

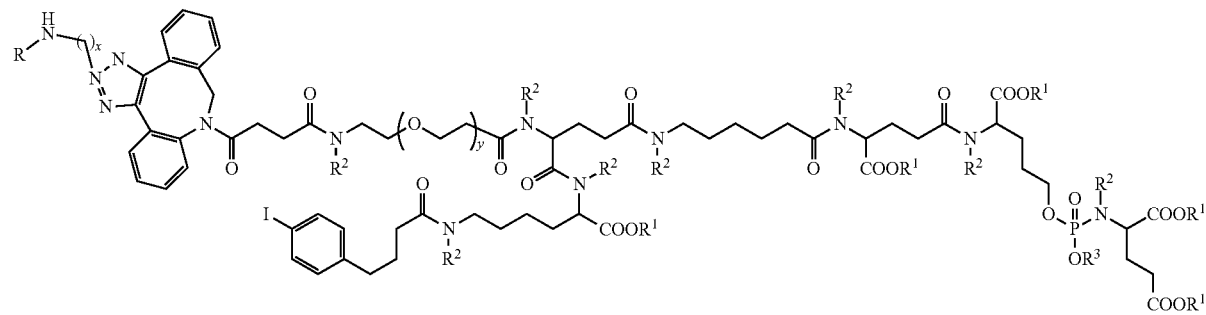

(Ig)

wherein y is 2, 3, 4, 5 or 6.

In embodiment I$_{15'}$, the compounds of embodiment I$_1$ have the structure of Formula (Ig) wherein x is 3.

In embodiment I$_{16}$, the compounds of embodiment I$_1$ have the structure of Formula (Ih):

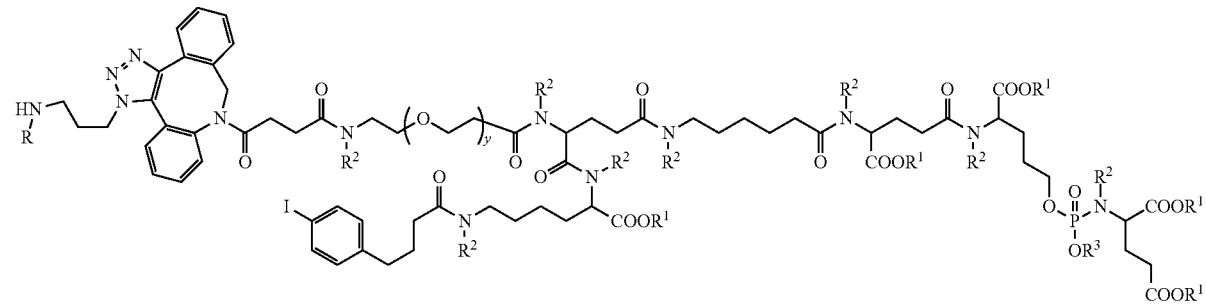

(Ih)

wherein y is 2, 3, 4, 5 or 6.

In embodiment $I_{17}$, the compounds are of any of embodiments 11-19, wherein y is 4.

In embodiment $I_{18}$, the compounds are of any of embodiments $I_1$-$I_{10}$, wherein R is a chelating agent optionally chelating a therapeutic radioisotope or a PET-active, SPECT-active, or MRI-active radioisotope. The chelating agent can comprise any chelator known in the art, see, e.g., Parus et al., "Chemistry and bifunctional chelating agents for binding (177)Lu," *Curr Radiopharm.* 2015; 8(2):86-94; Wängler et al., "Chelating agents and their use in radiopharmaceutical sciences," *Mini Rev Med Chem.* 2011 October; 11(11):968-83; Liu, "Bifunctional Coupling Agents for Radiolabeling of Biomolecules and Target-Specific Delivery of Metallic Radionuclides," *Adv Drug Deliv Rev.* 2008 September; 60(12): 1347-1370. Specific examples include, for example:

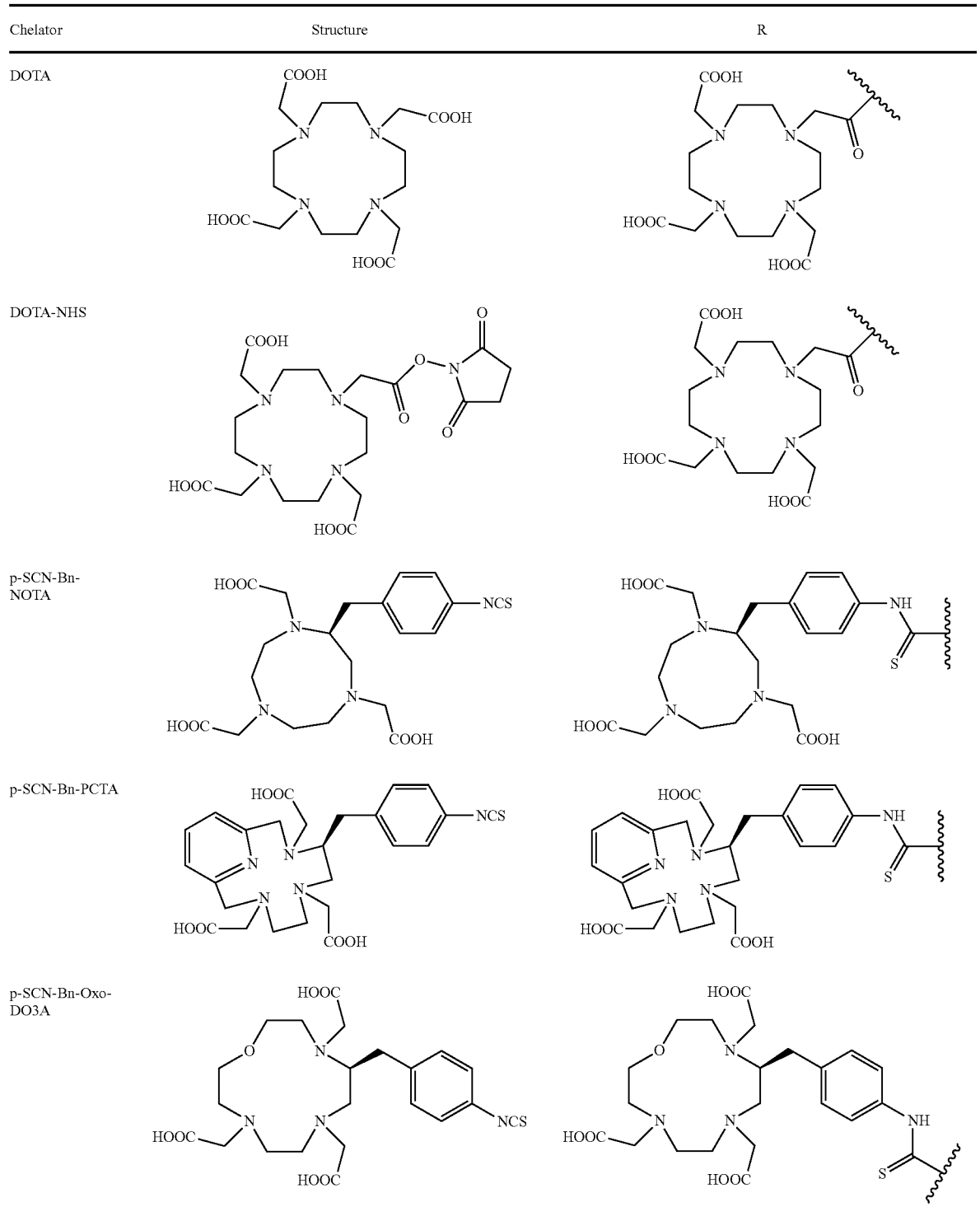

-continued

| Chelator | Structure | R |
|---|---|---|
| desferrioxamine-p-SCN | 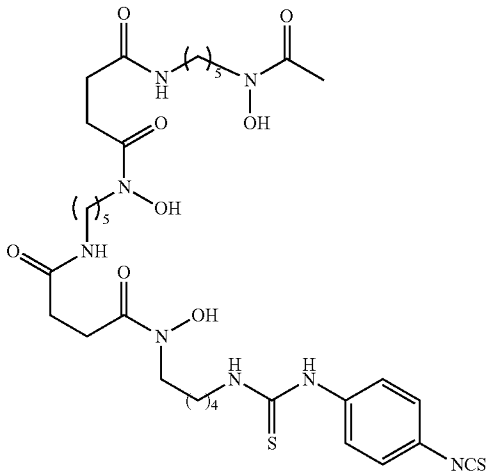 | |
| Diethylene-triamine-pentaacetic acid (DTPA) | 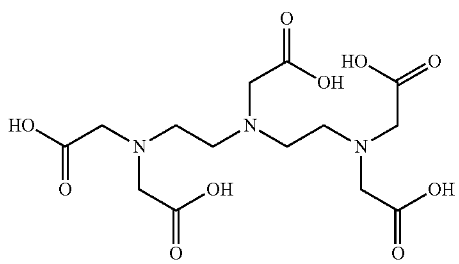 [SMILES: O=C(O)CN(CCN(CC(=O)O)CC(=O)O)CCN(CC(=O)O)CC(=O)O] | |
| 1,4,8,11-tetraazacyclotetra-decane1,4,8,11-tetraacetic acid (TETA) | 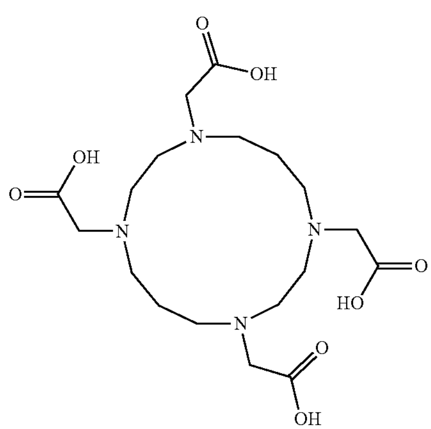 [SMILES: O=C(O)CN1CCCN(CC(=O)O)CCN(CC(=O)O)CCCN(CC(=O)O)CC1] | |
| N,N'-Di(2-hydroxybenzyl)ethylenediamine-N,N'-diacetic acid (HBED) | 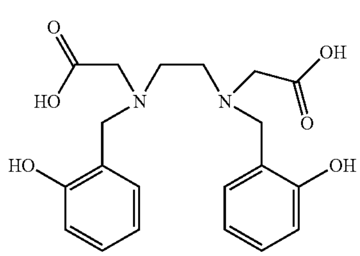 [SMILES: O=C(O)CN(CCN(CC(=O)O)Cc1ccccc1O)Cc1ccccc1O] | |

-continued
| Chelator | Structure | R |
|---|---|---|
| 4-(4,7-bis(2-(tert-butoxy)-2-oxoethyl)-1,4,7-triazacyclononan-1-yl)-5-(tert-butoxy)-5-oxopentanoic acid (NODAG) | 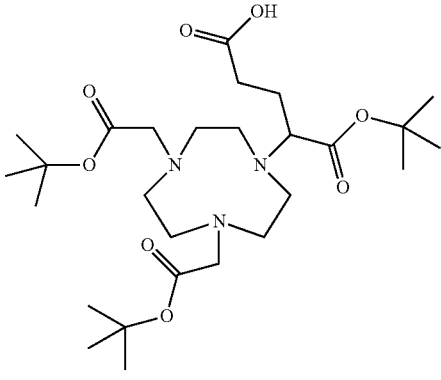 [SMILES: CC(C)(C)OC(=O)CN1CCN(CC(=O)OC(C)(C)C)CCN(C(CCC(=O)O)C(=O)OC(C)(C)C)CC1] | 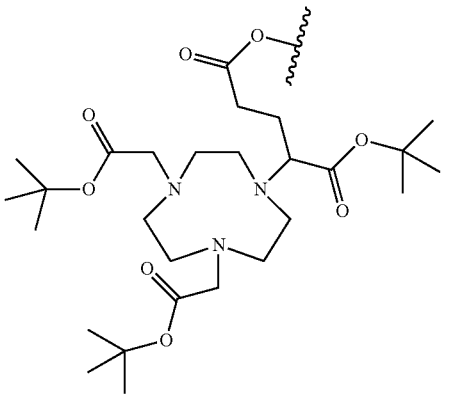 [SMILES: *OC(=O)CCC(C(=O)OC(C)(C)C)N1CCN(CC(=O)OC(C)(C)C)CCN(CC(=O)OC(C)(C)C)CC1] |
| 2,2'-(1,4,8,11-tetraazabicyclo[6.6.2]hexadecane-4,11-diyl)diacetic acid (CB-TE2A) | 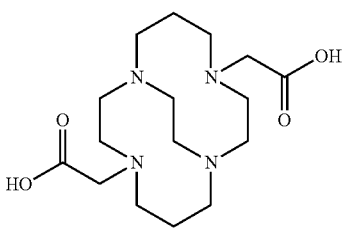 [SMILES: O=C(O)CN1CCCN2CCN(CCCN(CC(=O)O)CC2)CC1] | 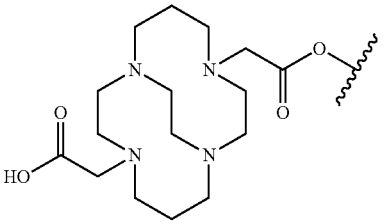 [SMILES: *OC(=O)CN1CCCN2CCN(CCCN(CC(=O)O)CC2)CC1] |
| 6-amino-2-(11-(phosphonomethyl)-1,4,8,11-tetraazabicyclo[6.6.2]hexadecan-4-yl)hexanoic acid (CB-TE1K1P) | 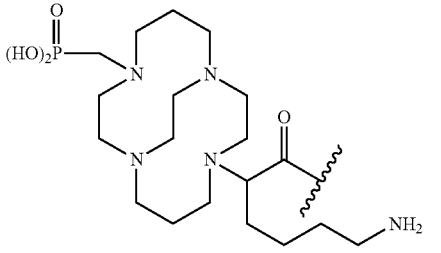 | 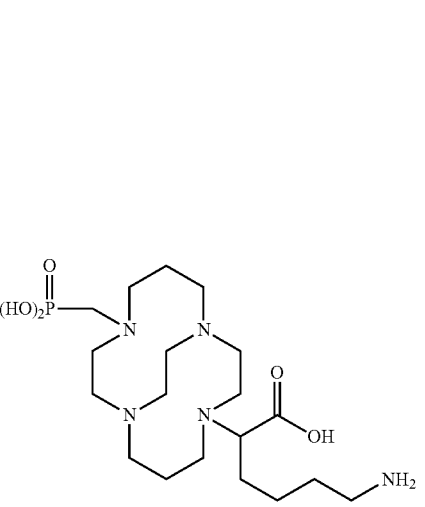 |

For example, in embodiment $I_{18a}$, R can be DOTA, bonded through any of its four carboxylic acid groups:
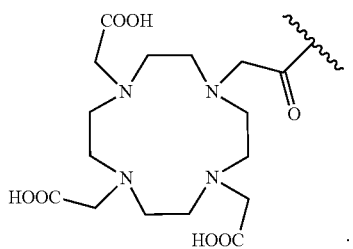
In embodiment $I_{18b}$, R can be
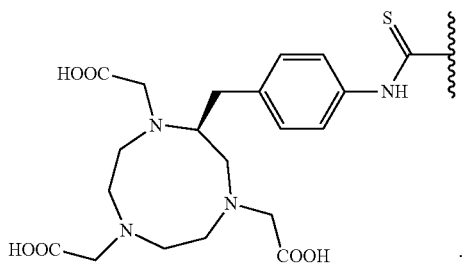 [SMILES: *C(=S)Nc1ccc(C[C@H]2CN(CC(=O)O)CCN(CC(=O)O)CCN2CC(=O)O)cc1]
In embodiment $I_{18c}$, R can be
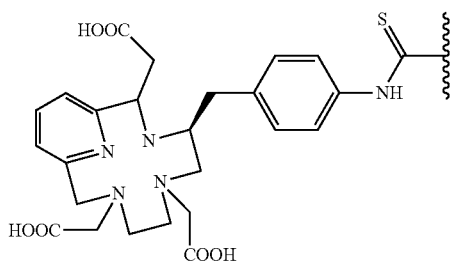 [SMILES: *C(=S)Nc1ccc(C[C@H]2CN(CC(=O)O)CCN(CC(=O)O)Cc3cccc(n3)C(CC(=O)O)N2)cc1]
In embodiment $I_{18d}$, can be
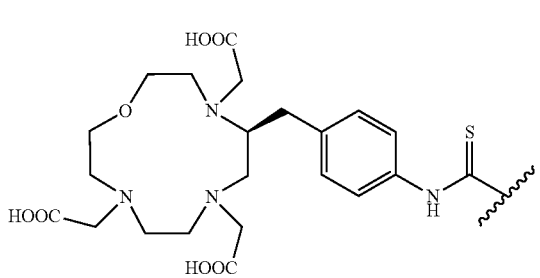 [SMILES: *C(=S)Nc1ccc(C[C@H]2CN(CC(=O)O)CCN(CC(=O)O)CCOCCN2CC(=O)O)cc1]
In embodiment $I_{18e}$, R can be
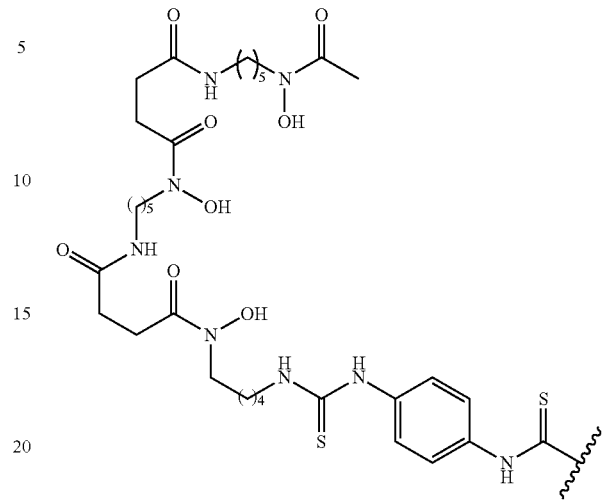
In embodiment $I_{18f}$, R can be
In embodiment $I_{18g}$, R can be
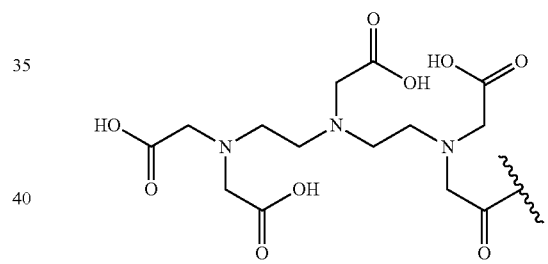
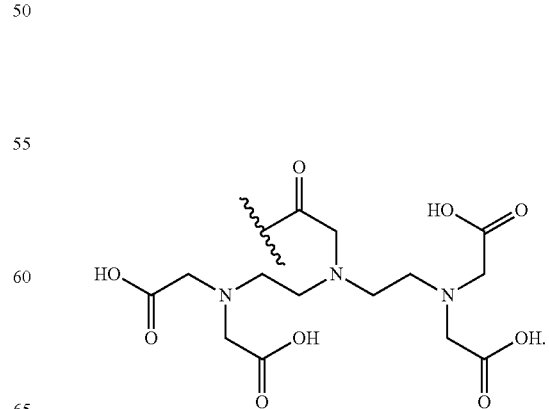

In embodiment I$_{18h}$, R can be

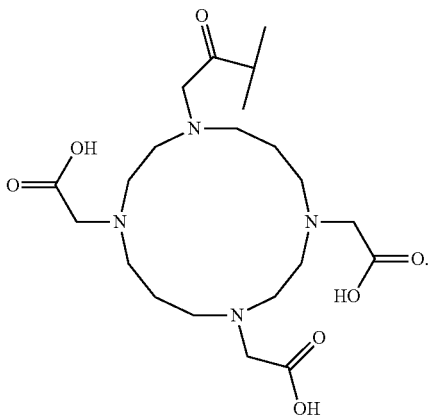 [SMILES: CC(C)C(=O)CN1CCCN(CC(=O)O)CCN(CC(=O)O)CCCN(CC(=O)O)CC1]

In embodiment I$_{18i}$, R can be

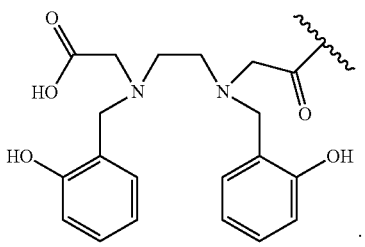 [SMILES: *C(=O)CN(CCN(CC(=O)O)Cc1ccccc1O)Cc1ccccc1O]

In embodiment I$_{18j}$, R can be

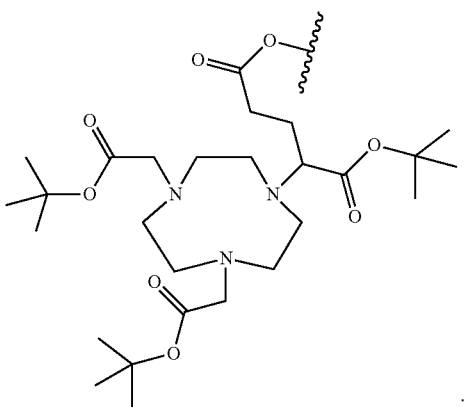 [SMILES: *OC(=O)CCC(C(=O)OC(C)(C)C)N1CCN(CC(=O)OC(C)(C)C)CCN(CC(=O)OC(C)(C)C)CC1]

In embodiment I$_{18k}$, R can be

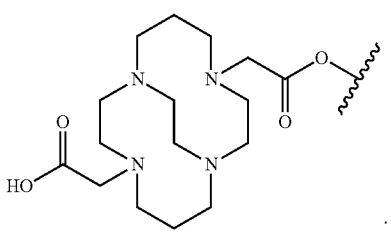

In embodiment I$_{18l}$, R can be

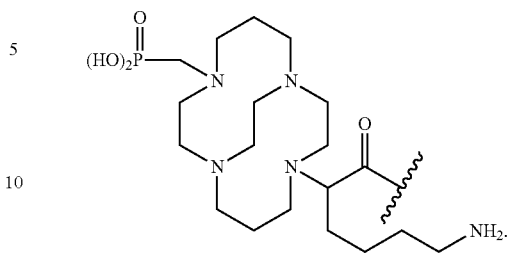

If necessary, additional bifunctional chelators can also be readily prepared using literature procedures.

In embodiment I$_{19}$, each of the preceding compounds may be chelated with a therapeutic radioisotope or a PET-active, SPECT-active, or MM-active radioisotope selected from $^{68}$Ga, $^{64}$Cu, $^{89}$Zr, $^{186/188}$Re, $^{90}$Y, $^{177}$Lu, $^{153}$Sm, $^{213}$Bi, $^{225}$Ac, and $^{223}$Ra.

In embodiment I$_{19a}$, each of the preceding compounds may be chelated with a therapeutic radioisotope or a PET-active, SPECT-active, or MM-active radioisotope that is $^{89}$Zr.

In embodiment I$_{19b}$, each of the preceding compounds may be chelated with a therapeutic radioisotope or a PET-active, SPECT-active, or MM-active radioisotope that is $^{64}$Cu.

In embodiment I$_{19c}$, each of the preceding compounds may be chelated with a therapeutic radioisotope or a PET-active, SPECT-active, or MM-active radioisotope that is with $^{68}$Ga.

In embodiment I$_{19d}$, each of the preceding compounds may be chelated with a therapeutic radioisotope or a PET-active, SPECT-active, or MM-active radioisotope that is $^{186/188}$Re.

In embodiment I$_{19e}$, each of the preceding compounds may be chelated with a therapeutic radioisotope or a PET-active, SPECT-active, or MRI-active radioisotope that is $^{90}$Y.

In embodiment I$_{19f}$, each of the preceding compounds may be chelated with a therapeutic radioisotope or a PET-active, SPECT-active, or MM-active radioisotope that is $^{177}$Lu.

In embodiment I$_{19g}$, each of the preceding compounds may be chelated with a therapeutic radioisotope or a PET-active, SPECT-active, or MM-active radioisotope that is $^{153}$Sm.

In embodiment I$_{19h}$, each of the preceding compounds may be chelated with a therapeutic radioisotope or a PET-active, SPECT-active, or MRI-active radioisotope that is $^{213}$Bi.

In embodiment I$_{19i}$, each of the preceding compounds may be chelated with a therapeutic radioisotope or a PET-active, SPECT-active, or MRI-active radioisotope that is $^{225}$Ac.

In embodiment I$_{19j}$, each of the preceding compounds may be chelated with a therapeutic radioisotope or a PET-active, SPECT-active, or MRI-active radioisotope that is $^{223}$Ra.

In embodiment I$_{20}$, the compounds are of any of embodiments I$_1$-I$_{19}$, wherein R$^1$ and R$^2$ are independently selected from one of groups (5a)-(5o):

(5a) hydrogen, $C_1$-$C_6$ alkyl or a protecting group.
(5b) hydrogen or $C_1$-$C_6$ alkyl.
(5c) $C_1$-$C_6$ alkyl or a protecting group.
(5d) $C_1$-$C_6$ alkyl
(5e) hydrogen or a protecting group.

(5l) hydrogen.
(5g) a protecting group
(5h) Any of groups (5a)-(5d), where $C_1$-$C_6$alkyl is methyl, ethyl, n-propyl, iso-propyl, n-butyl, sec-butyl, tert-butyl, n-pentyl or n-hexyl.
(5i) Any of groups (5a)-(5d), where $C_1$-$C_6$alkyl is methyl, ethyl, n-propyl, iso-propyl, n-butyl, sec-butyl or tert-butyl.
(5j) Any of groups (5a)-(5d), where $C_1$-$C_6$alkyl is methyl, ethyl, n-propyl or tert-butyl.
(5k) Any of groups (5a)-(5d), where $C_1$-$C_6$alkyl is methyl, ethyl or tert-butyl.
(5l) Any of groups (5a)-(5d), where $C_1$-$C_6$alkyl is methyl or ethyl.
(5m) Any of groups (5a)-(5d), where $C_1$-$C_6$alkyl is methyl.
(5n) Any of groups (5a)-(5d), where $C_1$-$C_6$alkyl is ethyl.
(5o) Any of groups (5a)-(5g), where $C_1$-$C_6$alkyl is tert-butyl.

A "protecting group" as used herein include, but are not limited to, optionally substituted benzyl, t-butyl ester, allyl ester, alkyl esters (e.g., methyl, ethyl), fluorenylmethoxycarbonyl groups (Fmoc), and amino, carboxylic acid and phosphorus acid protecting groups described in Greene's Protective Groups in Organic Synthesis, 4th Edition (which is incorporated by reference). In some embodiments, $R^1$ is a carboxylic acid protecting group (e.g., a methyl or t-butyl ester). In some embodiments, $R^2$ is a nitrogen protecting group (e.g., Boc, or benzyl).

Optionally benzyl groups include, but are not limited to, unsubstituted benzyl, triphenylmethyl (trityl), diphenylmethyl, o-nitrobenzyl, 2,4,6-trimethylbenzyl, p-bromobenzyl, p-nitrobenzyl, p-methoxybenzyl (PMB), 2,6-dimethoxybenzyl, 4-(methyl sulfinyl)benzyl, 4-sulfobenzyl, 4-azidomethoxybenzyl, and piperonyl, and benzyl protecting groups for carboxylic and phosphorus acids disclosed in Greene's Protective Groups in Organic Synthesis (the relevant parts of which are incorporated by reference).

In embodiment $I_{21}$, the compound of Formula (I) may be selected from the following:

(apo-CTT1403)

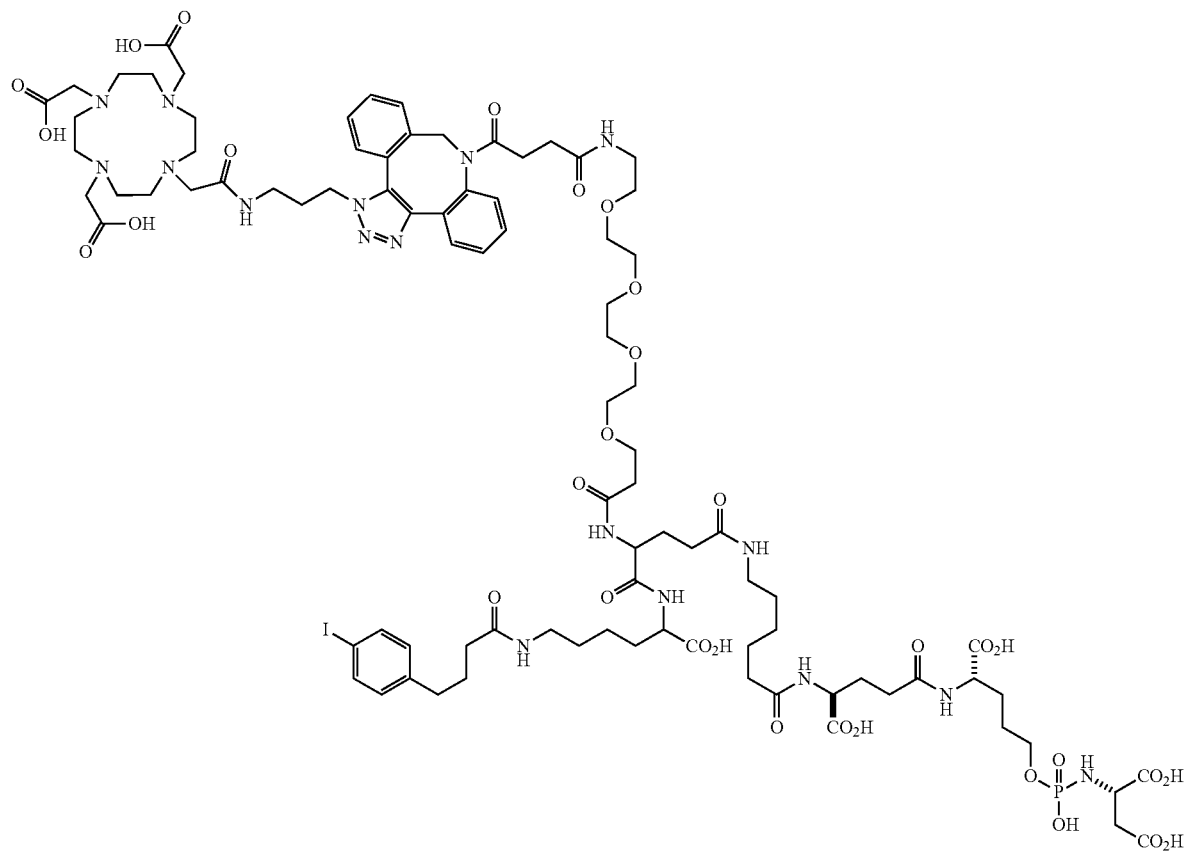

(4S,9S)-1-(((((S)-1,3-dicarboxypropyl)amino)(hydroxy)phosphoryl)oxy)-21-(17,20-dioxo-20-(1-(3-(2-(4,7,10-tris(carboxymethyl)-1,4,7,10-tetraazacyclododecan-1-yl)acetamido)propyl)-1,9-dihydro-8H-dibenzo[b,f][1,2,3]triazolo[4,5-d]azocin-8-yl)-4,7,10,13-tetraoxa-16-azaicosanamido)-33-(4-iodophenyl)-6,11,18,22,30-pentaoxo-5,10,,17,23,29-pentaazatritriacontane-4,9,24-tricarboxylic acid;

-continued
(apo-CTT1403)
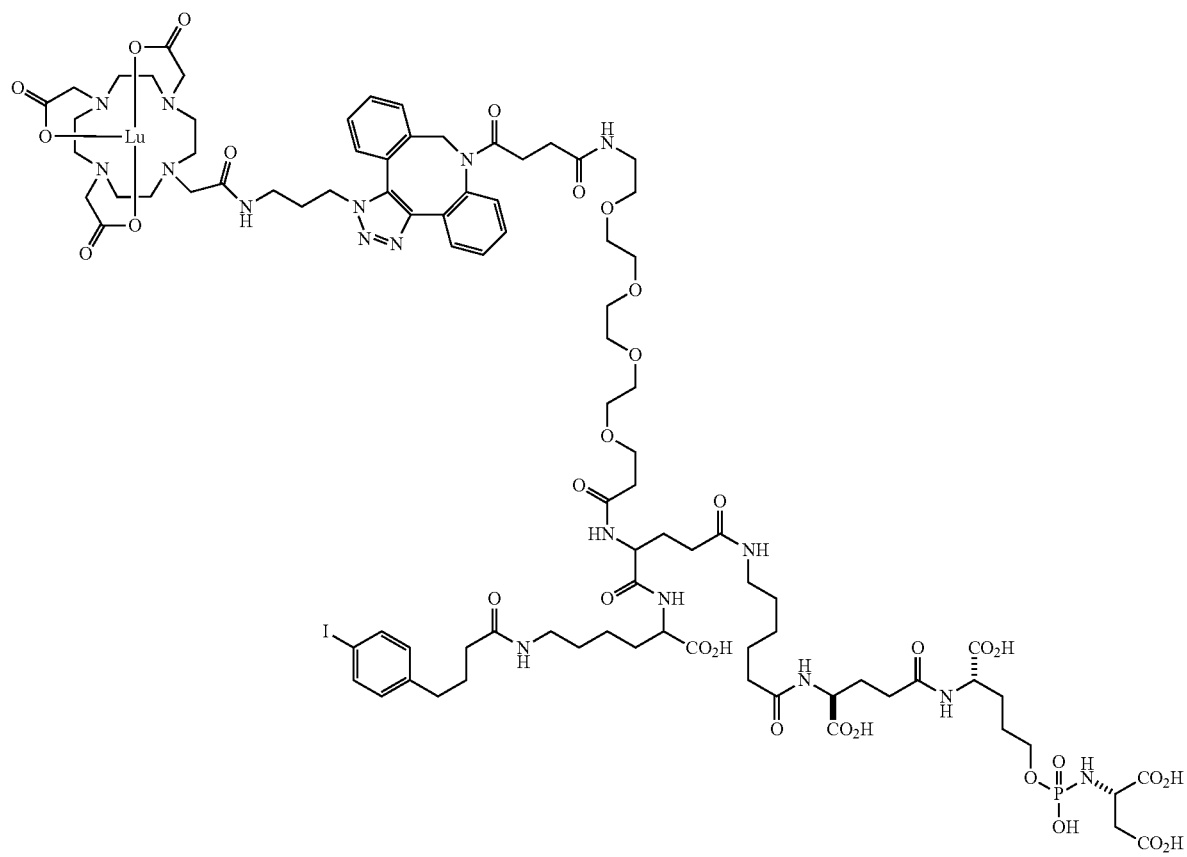
[175Lu] (4S,9S)-1-(((((S)-1,3-dicarboxypropyl)amino)(hydroxy)phosphoryl)oxy)-21-(17,20-dioxo-20-(1-(3-(2-(3,16,19-trioxo-2,17,18-trioxa-5,8,11,14-tetraazatricyclo[9.6.3.2^{5,14}]docosan-8-yl)acetamido)propyl)-1H-dibenzo[b,f][1,2,3]triazolo[4,5-d]azocin-8(9H)-yl)-4,7,10,13-tetraoxa-16-azaicosanamido)-33-(4-iodophenyl)-6,11,18,22,30-pentaoxo-5,10,17,23,29-pentaazatritriacontane-4,9,24-tricarboxylic acid, lutetium salt -continued (CTT1403)

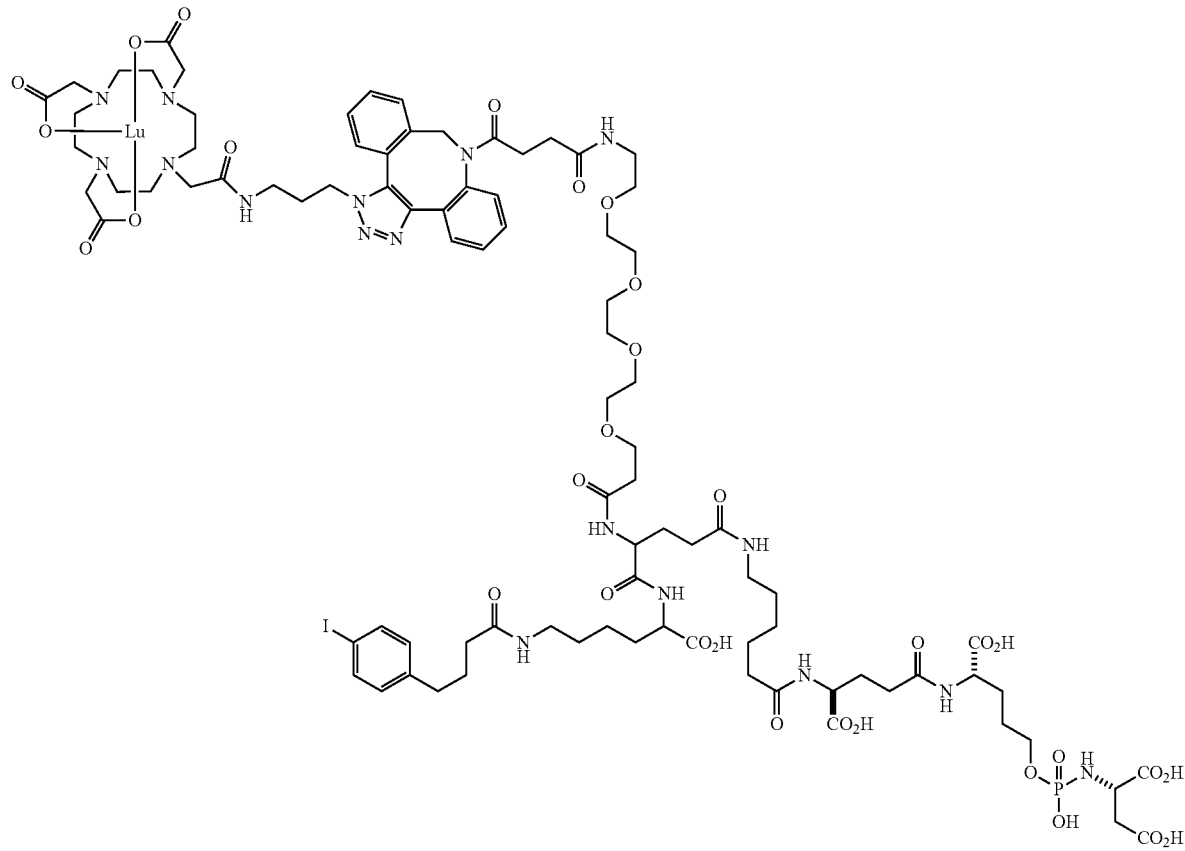

[177Lu] (4S,9S)-1-(((((S)-1,3-dicarboxypropyl)amino)hydroxy)phosphoryl)oxy)-21-(17,20-dioxo-20-(1-(3-(2-(3,16,19-trioxo-2,17,18-trioxa-5,8,11,14-tetraazatricyclo[9.6.3.2$^{5,14}$]docosan-8-yl)acetamido)propyl)-1H-dibenzo[b,f][1,2,3]triazolo[4,5-d]azocin-8(9H)-yl)-4,7,10,13-tetraoxa-16-azaicosanamido)-33-(4-iodophenyl)-6,11,18,22,30-pentaoxo-5,10,17,23,29-pentaazatritriacontane-4,9,24-tricarboxylic acid, lutetium salt or a pharmaceutically acceptable salt thereof.

In embodiment $I_{22}$, the present disclosure provides a pharmaceutical composition comprising a compound of Formula (I) and a pharmaceutically acceptable carrier.

In embodiment $I_{23}$, the present disclosure provides a method for imaging one or more prostate cancer cells in a patient comprising administering to the patient a compound of Formula (I) or a pharmaceutical composition thereof. The method may further include imaging the compound of Formula (I) in vivo. The imaging can be performed with any PET-imaging techniques known in the art.

In embodiment $II_1$ of this aspect, the disclosure provides compounds of formula (II):

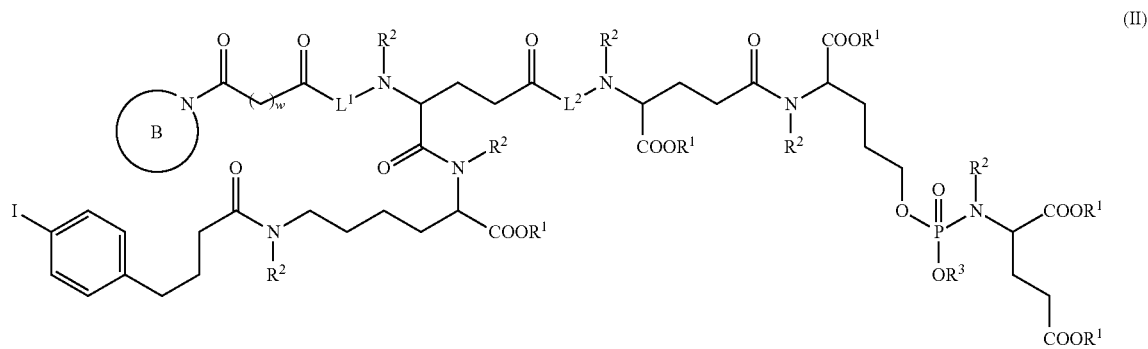

(II)

or a pharmaceutically acceptable salt thereof, wherein
L¹ and L² are independently a divalent linking group;
ring B is heterocyclic; and
each $R^1$ and $R^2$ are independently hydrogen, $C_1$-$C_6$ alkyl or a protecting group.

In embodiment $II_2$, $L^1$, $L^2$, $R^1$ and $R^2$ are as described above.

In embodiment $II_3$, the compounds of embodiment $II_1$ have the structure of formula (IIa):

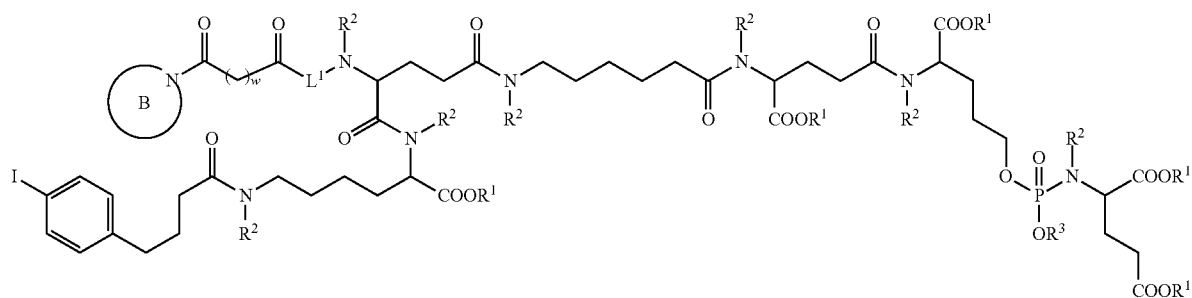

(IIa)

or a pharmaceutically acceptable salt thereof.

In embodiment $II_4$, the compounds of embodiment $II_1$ have the structure of formula (IIb):

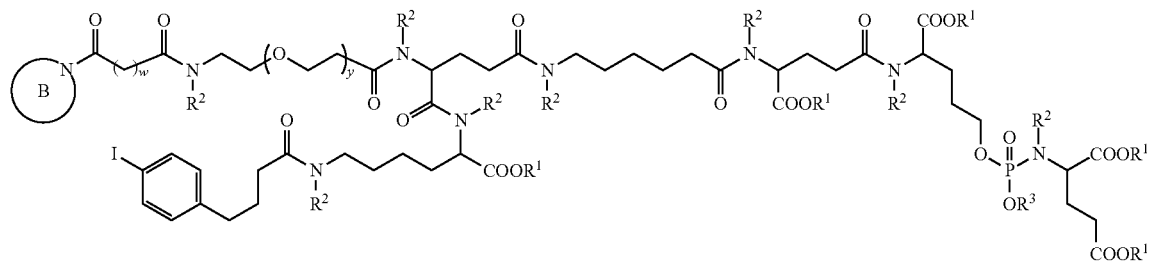

(IIb)

or a pharmaceutically acceptable salt thereof, wherein y is 2, 3, 4, 5 or 6.

In embodiment II$_{4a}$, the compounds are of embodiment II$_4$ wherein ring B is:
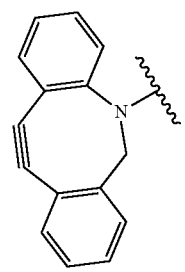 [SMILES: *N1Cc2ccccc2C#Cc2ccccc21]
In embodiment II$_5$, the compounds of embodiment II$_1$ have the structure of formula (IIc):
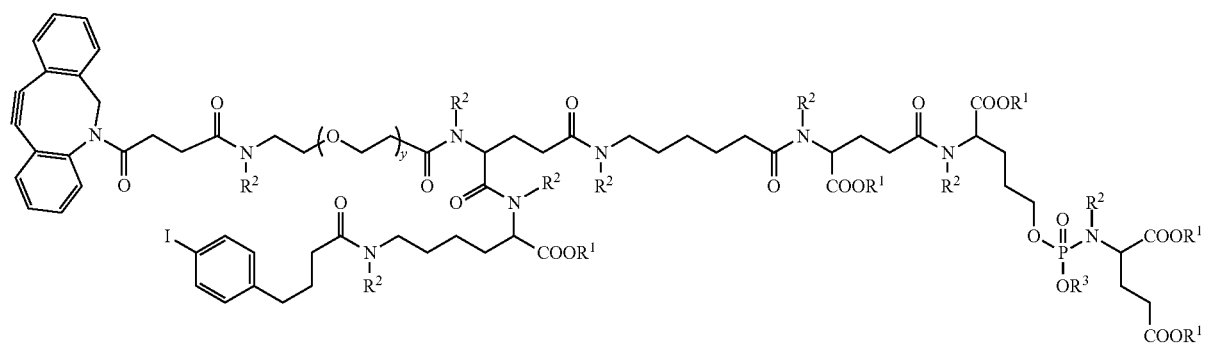
(IIc)
or a pharmaceutically acceptable salt thereof, wherein y is 2, 3, 4, 5 or 6.

In embodiment II₆, the compounds are of any of embodiments wherein y is 4.
In embodiment I₇, the compound of Formula (II) may be
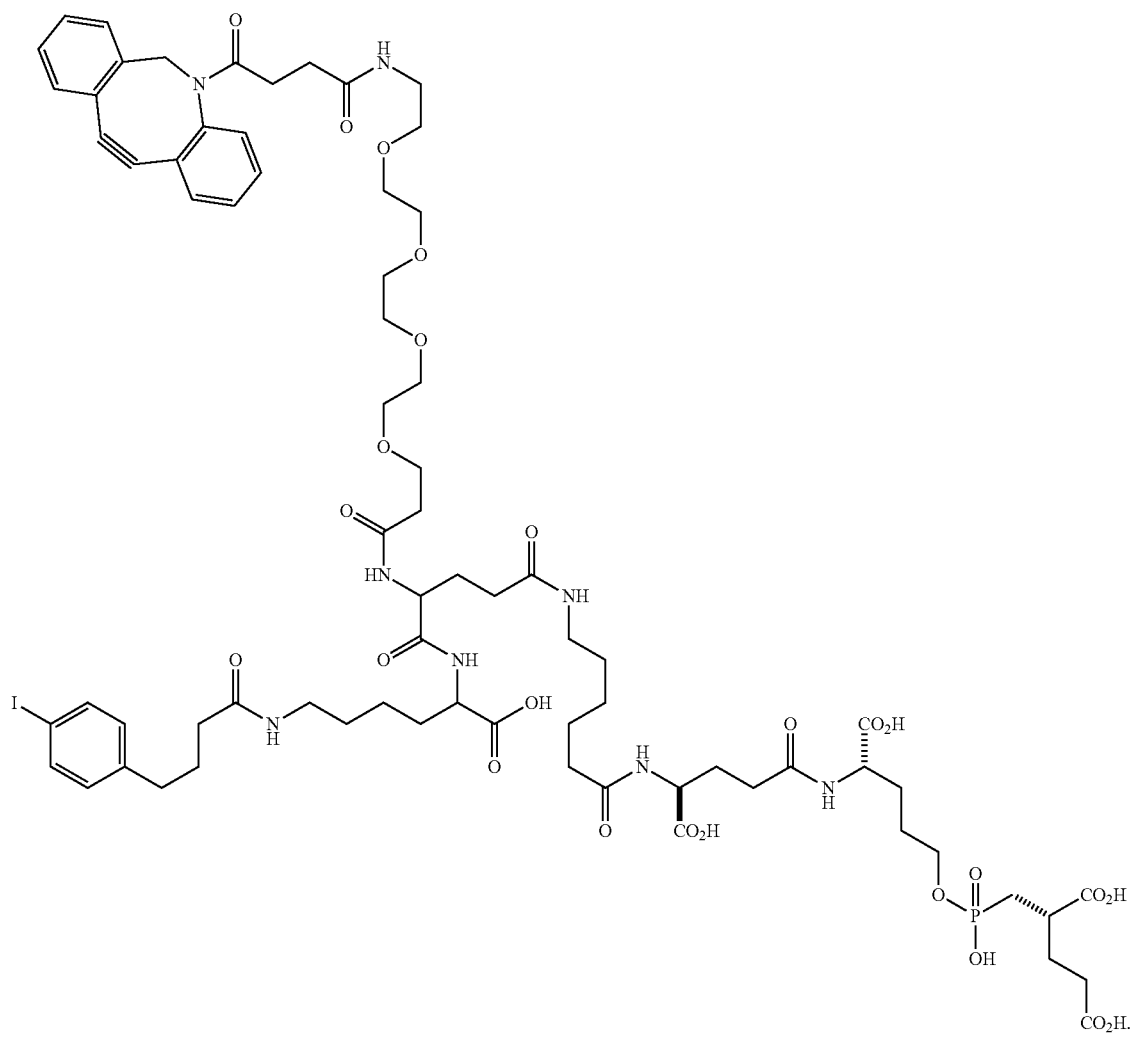
(CTT1402)
(4S,9S,24S)-21-(20-(11,12-didehydrodibenzo[b,f]azocin-5(6H)-yl)-17,20-dioxo-4,7,10,13-tetraoxa-16-azaicosanamido)-1-(((((S)-1,3-dicarboxypropyl)amino)(hydroxy)phosphoryl)oxy)-33-(4-iodophenyl)-6,11,18,22,30-pentaoxo-5,10,17,23,29-pentaazatritriacontane-4,9,24-tricarboxylic acid
or a pharmaceutically acceptable salt thereof.

In embodiment MI of this aspect, the disclosure provides compounds of the structure:
(CTT1400)
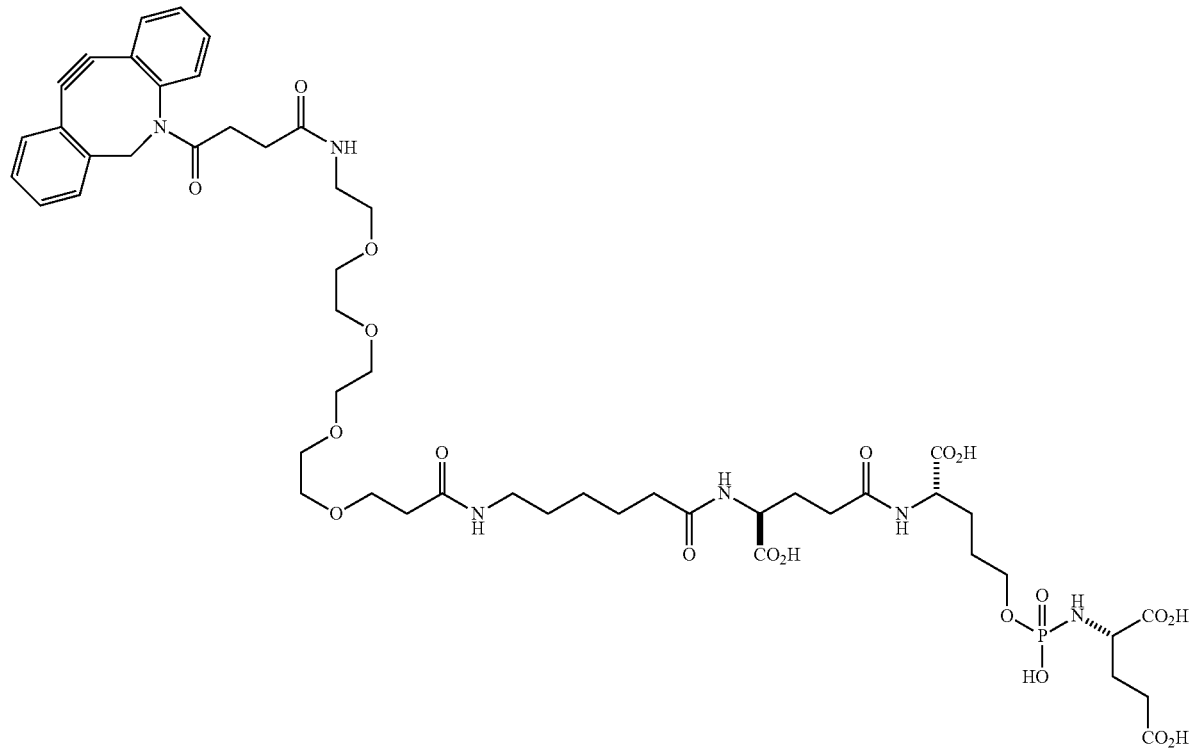
(CTT1401)
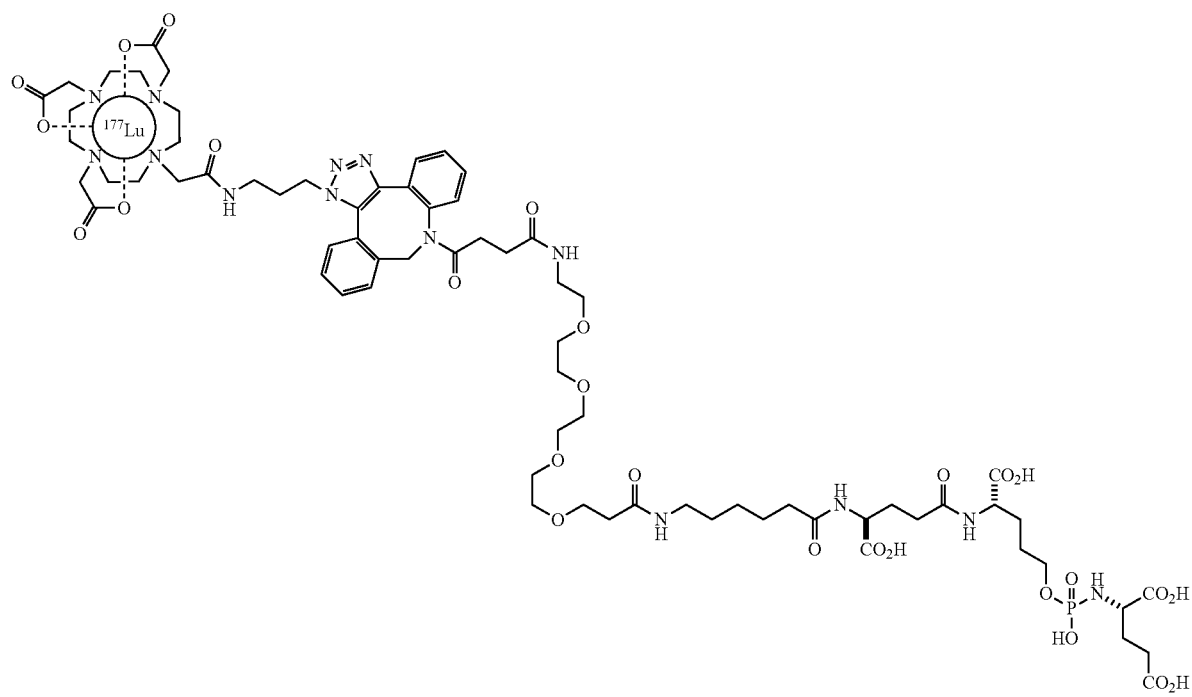
or a pharmaceutically acceptable salt thereof.

In another aspect, the disclosure provides a method for preparing a compound according to Formula (I). Compounds according to the invention can be made using art recognized techniques combined with methods analogous to those disclosed below.

In embodiment $IV_1$ of this aspect, the disclosure provides a method for preparing a compound according to Formula (I*) or Formula (I), the method comprising reacting an azide- or alkyne-containing chelating agent optionally associated with a PET-active or therapeutic radioisotope with a azide- or alkyne-modified PMSA inhibitor of formula (IV)

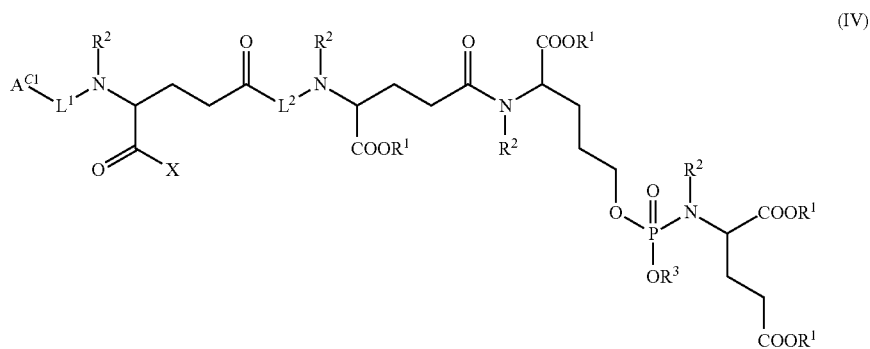

wherein
$L^1$ and $L^2$ are independently a divalent linking group;
$A^{C1}$ comprises an azide or alkyne functional group;
each $R^1$ and $R^2$ are independently hydrogen, $C_1$-$C_6$ alkyl or a protecting group; and
X is an albumin bind moiety,
provided that when $A^{C1}$ comprises an azide functional group it is reacted with an alkyne-containing chelating agent optionally associated with a PET-active or therapeutic radioisotope, and when $A^{C1}$ comprises an alkyne functional group it is reacted with an azide-containing chelating agent optionally associated with a PET-active or therapeutic radioisotope.

In embodiment $IV_2$, the azide- or alkyne-modified PMSA inhibitor of embodiment $IV_1$ has the structure of Formula (IVa):

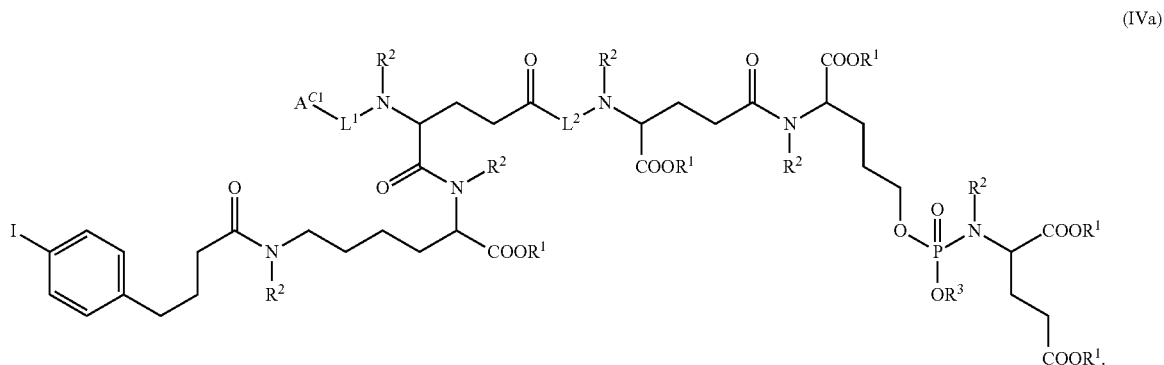

In embodiment IV$_3$, the azide- or alkyne-modified PMSA inhibitor of embodiment IV$_1$ has the structure of Formula (IVb):

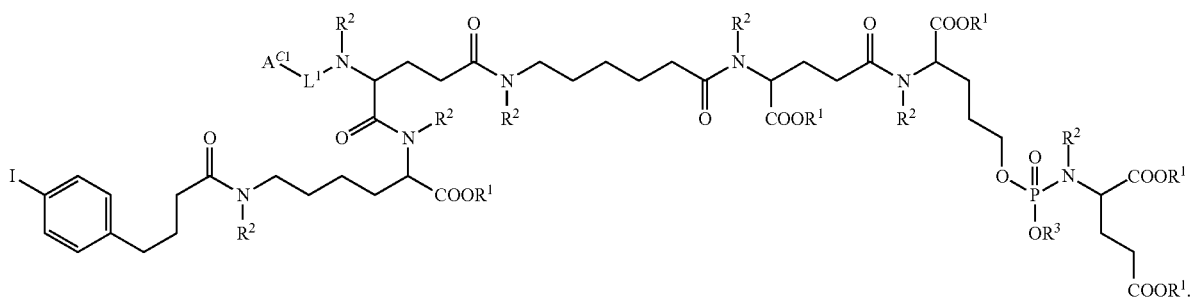

(IVb)

In embodiment IV$_4$, the azide- or alkyne-modified PMSA inhibitor of embodiment IV$_1$ has the structure of Formula (IVc):

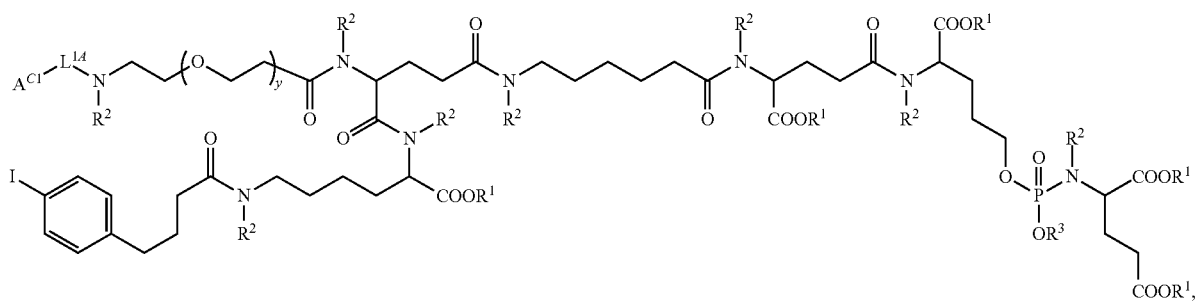

(IVc)

wherein y is 2, 3, 4, 5 or 6.

In embodiment IV$_5$, the alkyne-modified PMSA inhibitor of embodiment IV$_1$ has the structure of Formula (IVd):

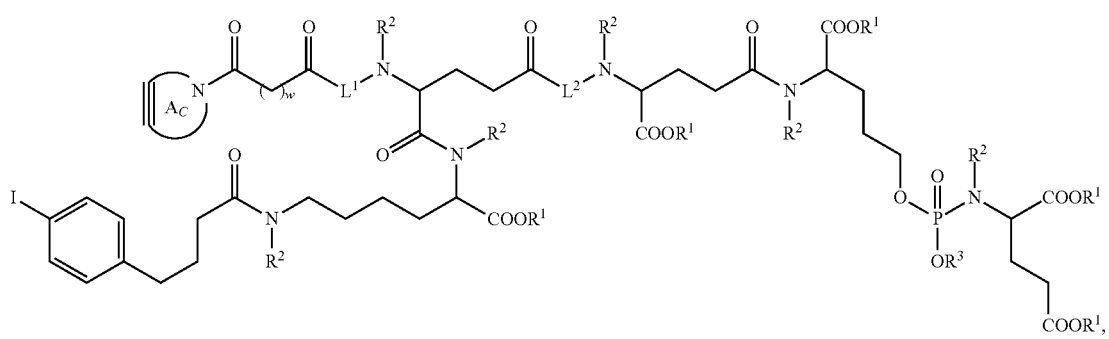

(IVd)

or a pharmaceutically acceptable salt thereof.

wherein ring Ac is heterocyclic and w is as described herein.

In embodiment IV₆, the alkyne-modified PMSA inhibitor of embodiment IV₁ has the structure of Formula (IVe):
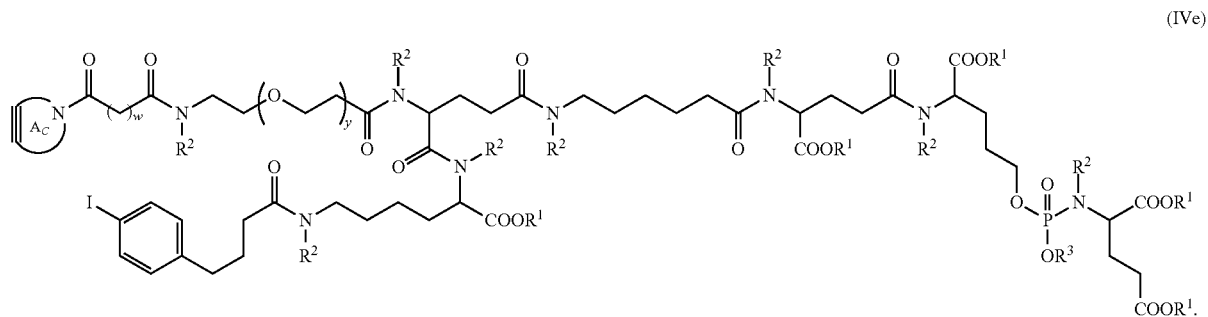
(IVe)
In embodiment IV₇, the alkyne-modified PMSA inhibitor of embodiment IV₁ has the structure of Formula (IVf):
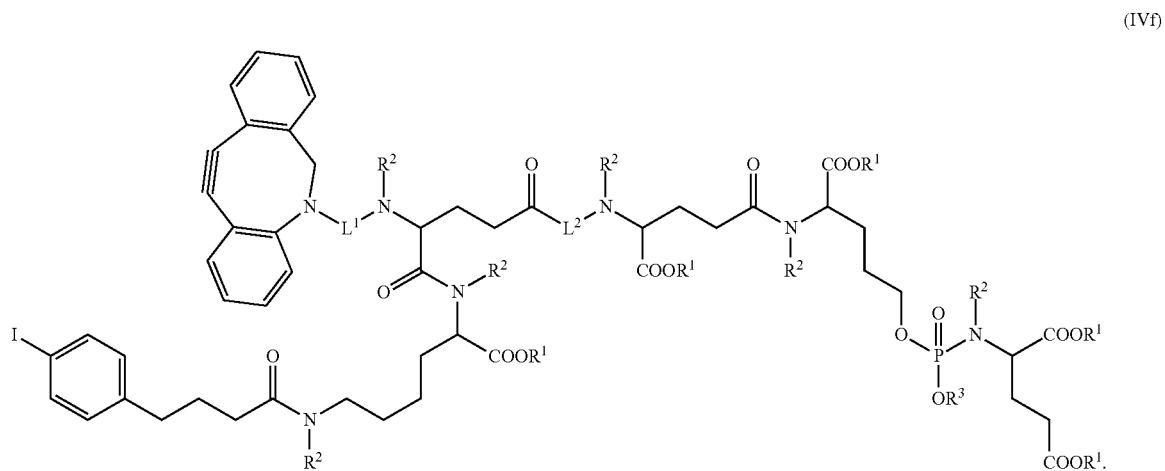
(IVf)
In embodiment IV₈, the alkyne-modified PMSA inhibitor of embodiment IV₁ has the structure of Formula (IVg):
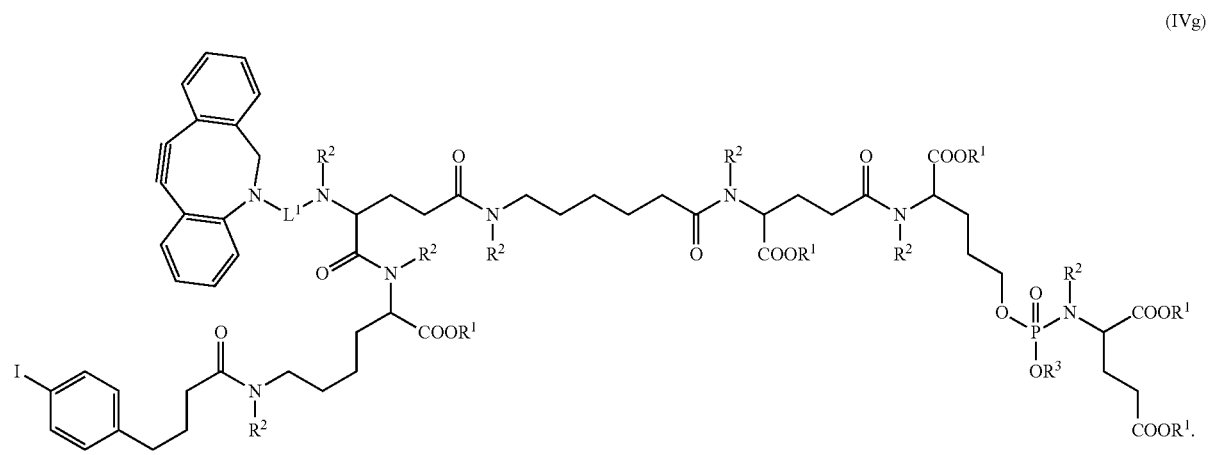
(IVg)

In embodiment IV$_9$, the alkyne-modified PMSA inhibitor of embodiment IV$_1$ has the structure of Formula (IVh):

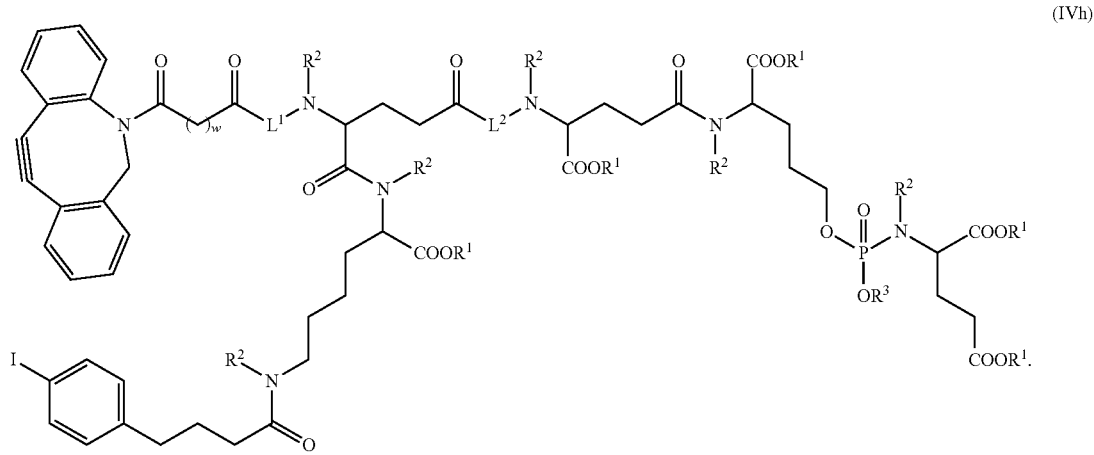

(IVh)

In embodiment IV$_{10}$, the alkyne-modified PMSA inhibitor of embodiment IV$_1$ has the structure of Formula (IVi):

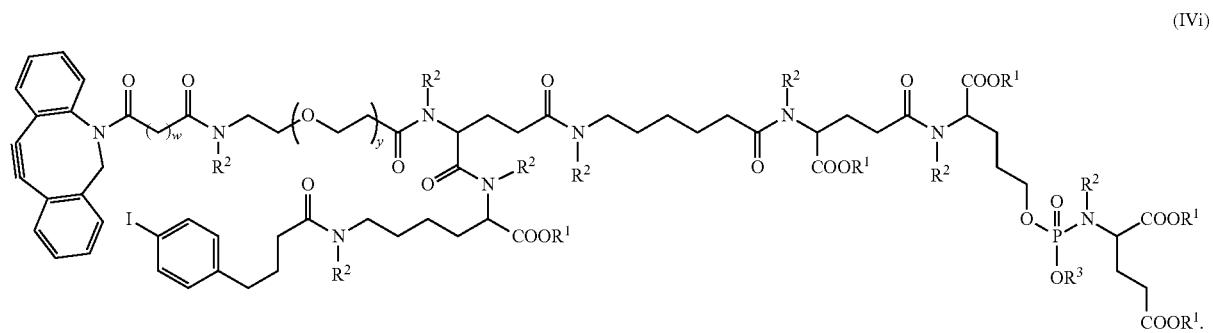

(IVi)

In embodiment IV$_{11}$, the azide- or alkyne-containing chelating agent optionally associated with a PET-active or therapeutic radioisotope of embodiment VI has the structure of Formula (V):

(V)

wherein
- R is a chelating agent optionally associated with a PET-active or therapeutic radioisotope;
- L$^{1B}$ is a divalent linker; and
- A$^{C2}$ is an azide or alkyne.

In embodiment IV$_{12}$, the azide- or alkyne-containing chelating agent optionally associated with a PET-active or therapeutic radioisotope of embodiment IV$_1$ has the structure of Formula (Va):

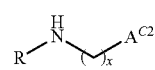

(Va)

wherein x is 0, 1, 2, 3, 4, 5 or 6.

In embodiment IV$_{13}$, the azide- or alkyne-containing chelating agent optionally associated with a PET-active or therapeutic radioisotope of embodiment IV$_1$ has the structure of Formula (V) or Formula (Va), wherein R comprises DOTA, NOTA, PCTA, DO3A, HBED, NODAG, CB-TE2A, CB-TE1K1P or desferrioxamine optionally associated with $^{89}$Zr, $^{64}$Cu, $^{68}$Ga, $^{186/188}$Re, $^{90}$Y, $^{177}$Lu, $^{153}$Sm, $^{213}$Bi, $^{225}$Ac, or $^{223}$Ra.

In embodiment IV$_{14}$, the azide- or alkyne-containing chelating agent optionally associated with a PET-active or therapeutic radioisotope of embodiment IV$_1$ has the structure of Formula (Vb):

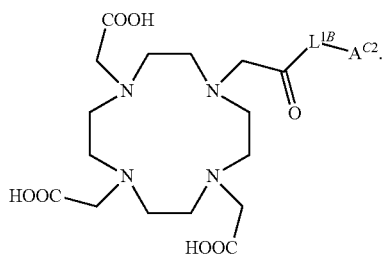
(Vb)

In embodiment IV$_{15}$, the azide- or alkyne-containing chelating agent optionally associated with a PET-active or therapeutic radioisotope of embodiment IV$_1$ has the structure of Formula (Vc):

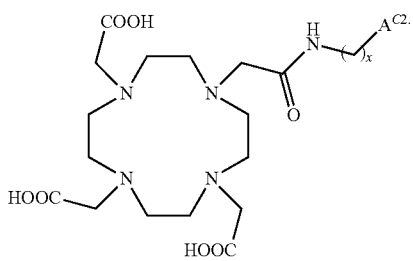
(Vc)

In embodiment IV$_{16}$, the azide-containing chelating agent optionally associated with a PET-active or therapeutic radioisotope of embodiment IV$_1$ has the structure of Formula (Vd):

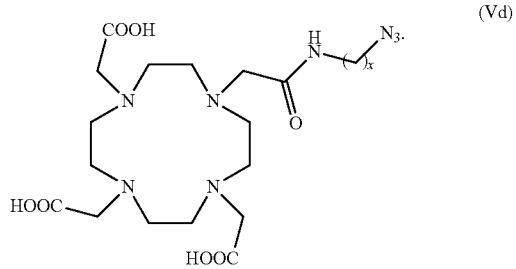
(Vd)

In embodiment IV$_{17}$, the azide-containing chelating agent optionally associated with a PET-active or therapeutic radioisotope of embodiment IV$_1$ is of Formula (IVd):

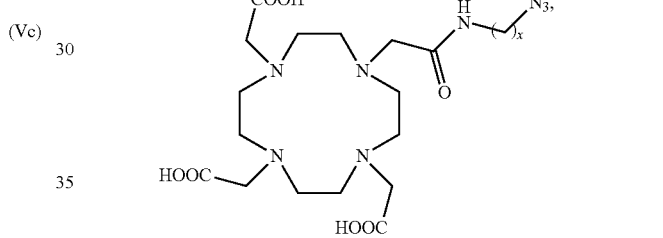
(IVd)

and the alkyne-modified PMSA inhibitor of embodiment IV$_1$ is of Formula (IVi):

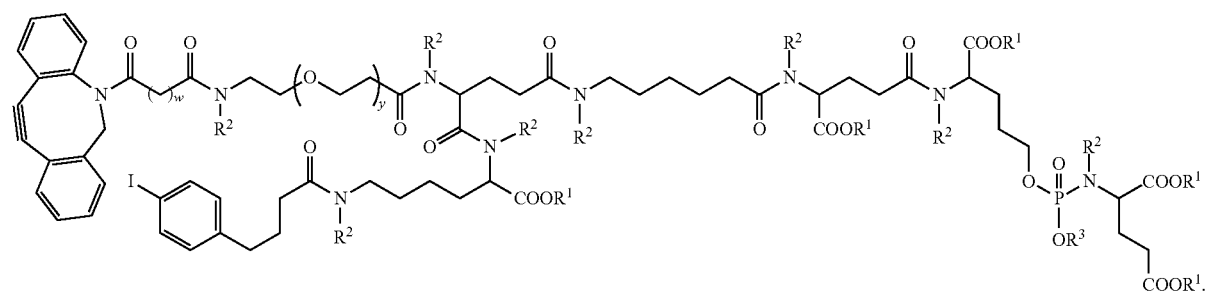
(IVi)

In embodiment IV$_{18}$, the method is of embodiment IV$_{17}$ wherein
x is 3;
y is 4; and
w is 2.
In embodiment IV$_{19}$, the method is of embodiment IV$_1$ wherein the compound of Formula (I) has the structure
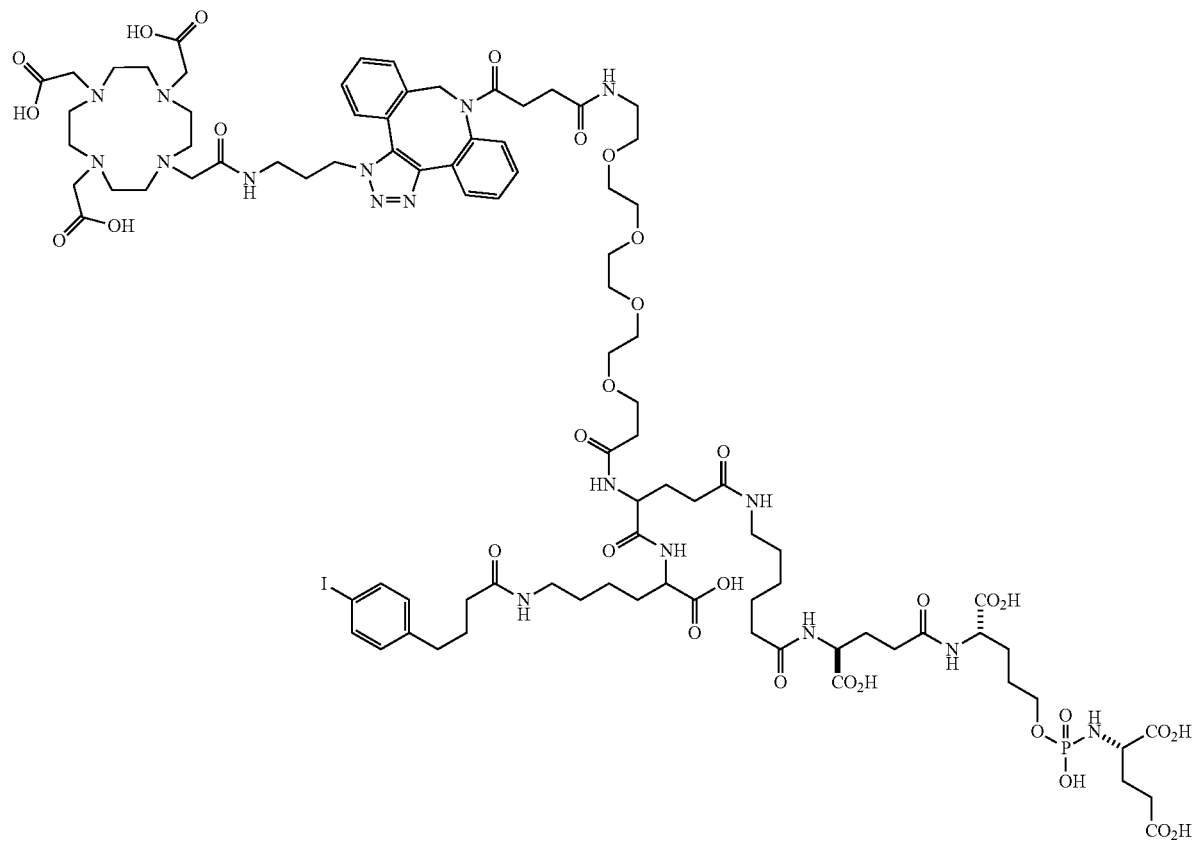

the azide-containing chelating agent associated with a PET-active or therapeutic radioisotope has the structure
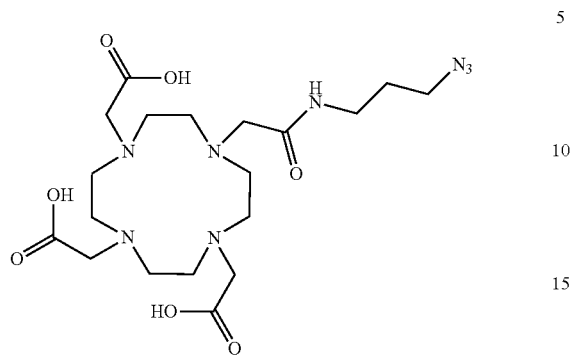
and the alkyne-modified PMSA inhibitor has the structure
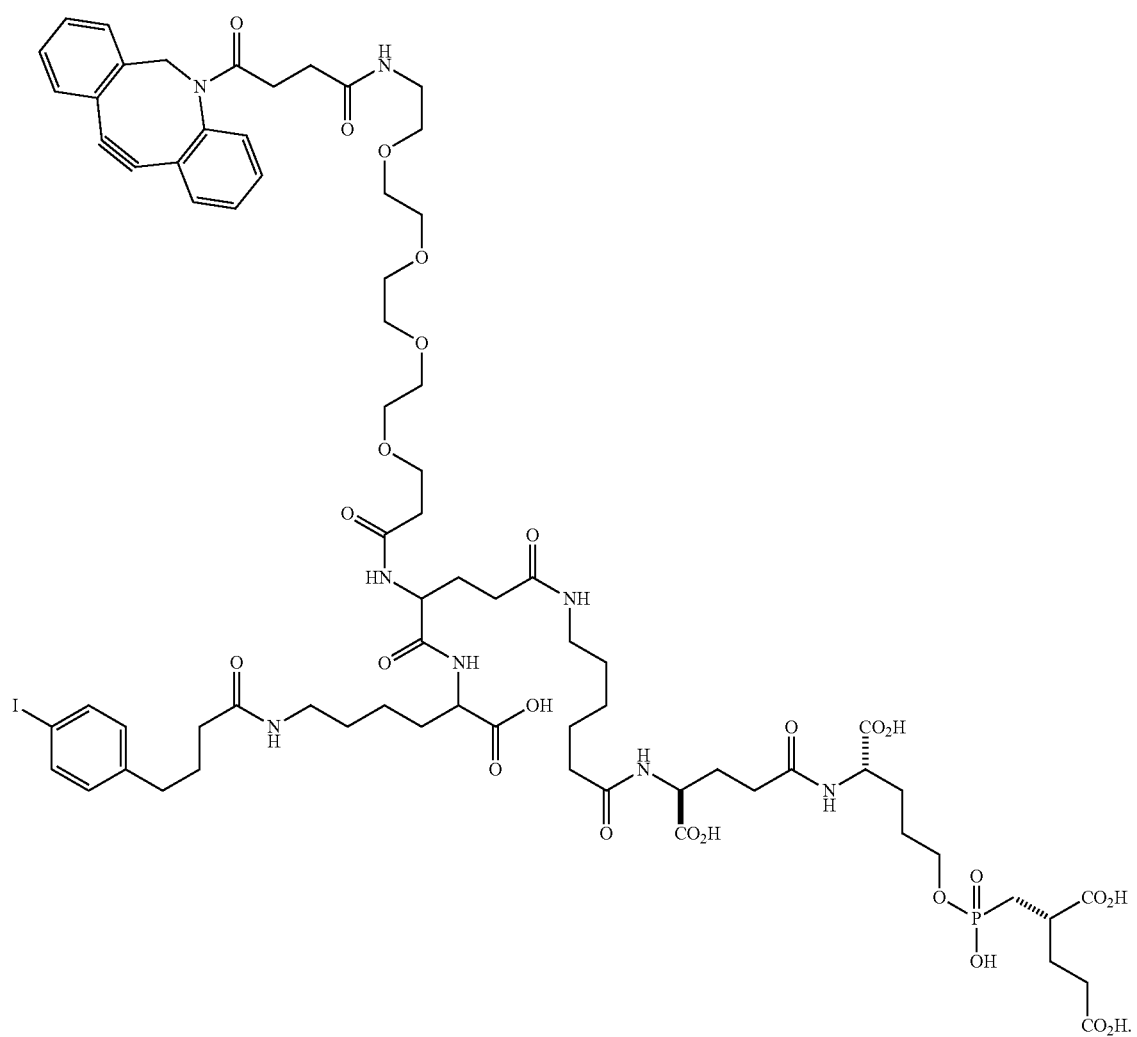

In embodiment IV$_{19}$, the method is of embodiment IV$_1$ wherein the compound of Formula (I) has the structure
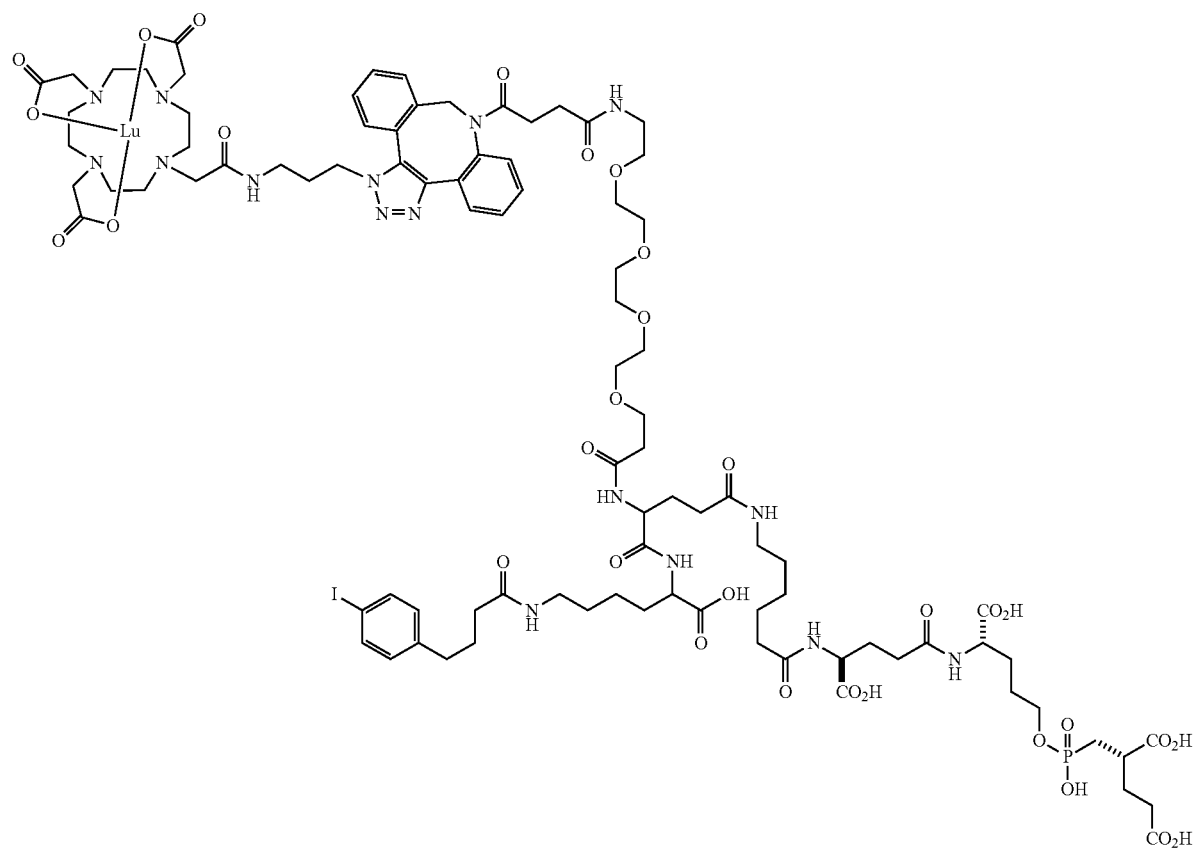

the azide-containing chelating agent associated with a PET-active or therapeutic radioisotope has the structure
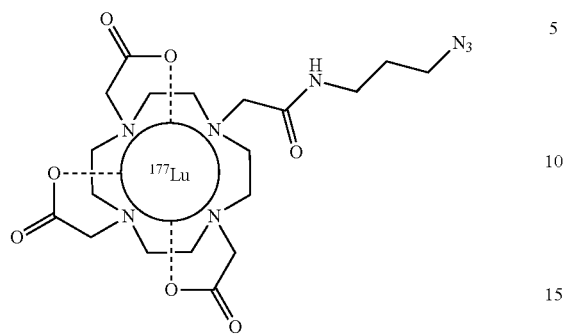
and the alkyne-modified PMSA inhibitor has the structure
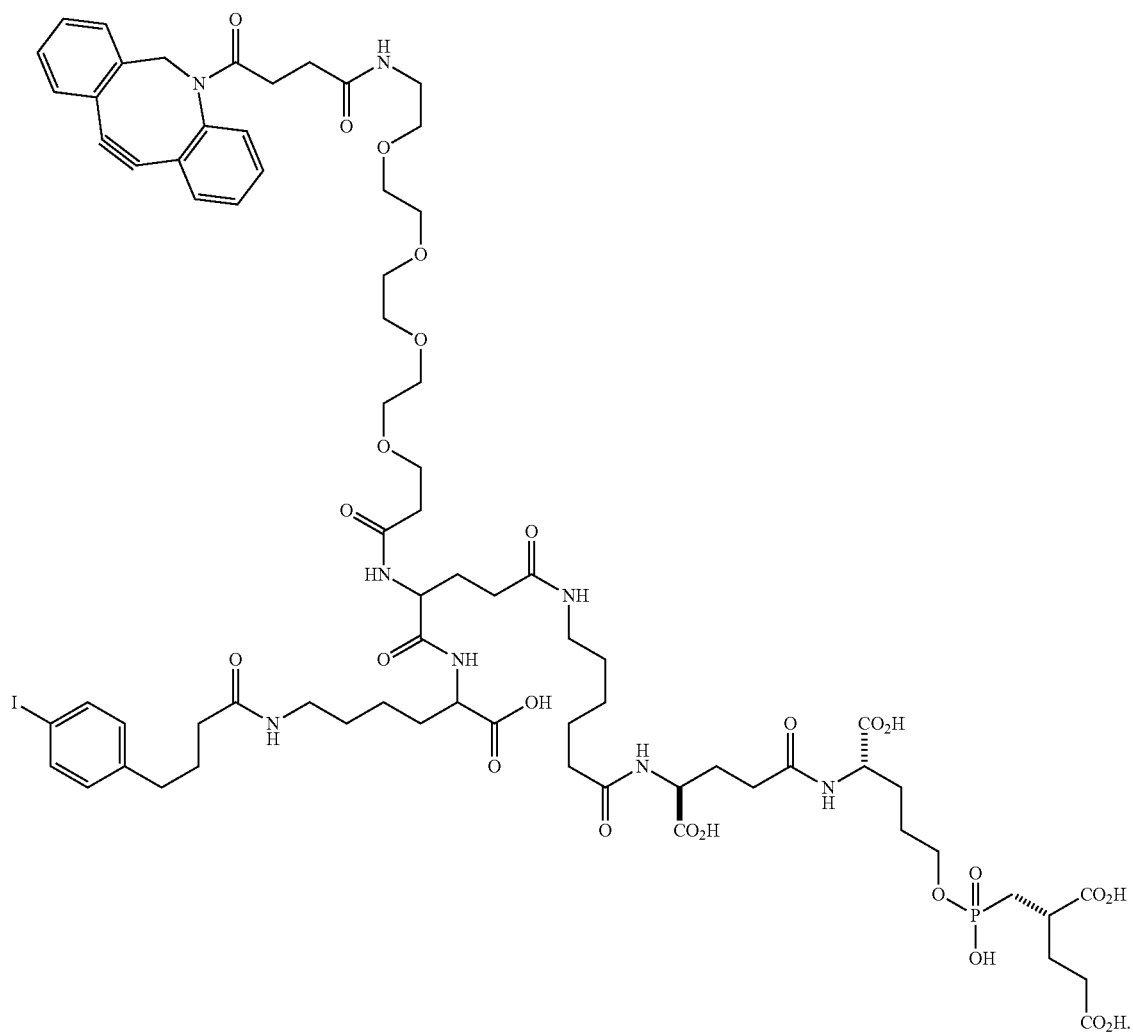

In embodiment $V_1$ of this aspect, the disclosure provides a method for preparing a compound of the structure
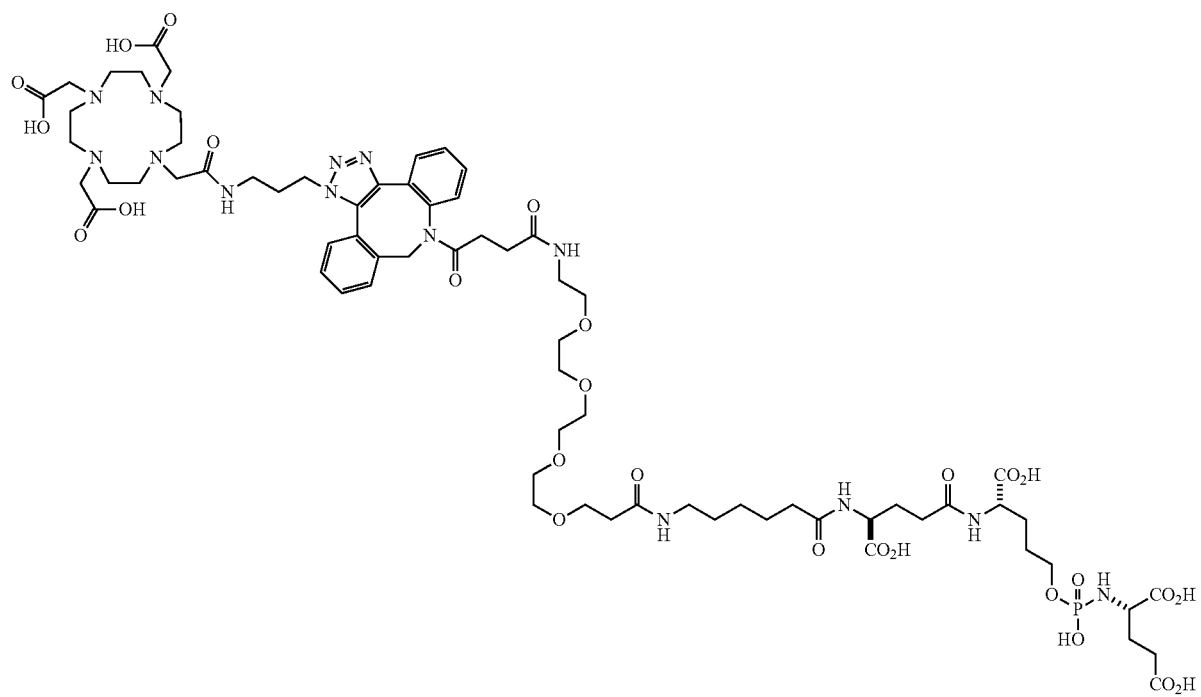

the method comprising reacting an azide-containing chelating agent optionally associated with a PET-active or therapeutic radioisotope of the structure
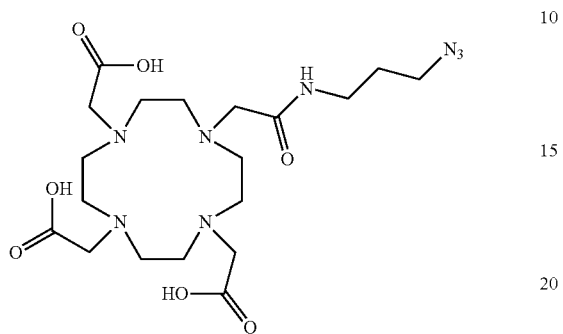
with a alkyne-modified PMSA inhibitor of the structure
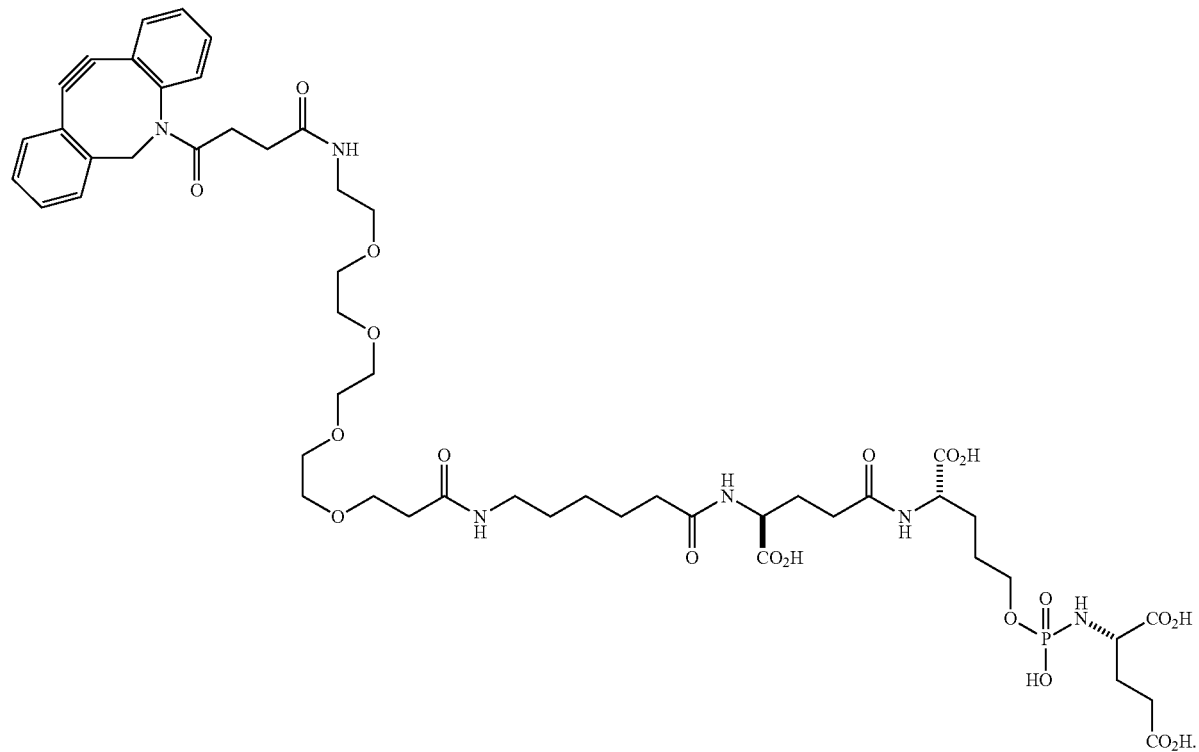

In embodiment $V_2$ of this aspect, the disclosure provides a method for preparing a compound of the structure
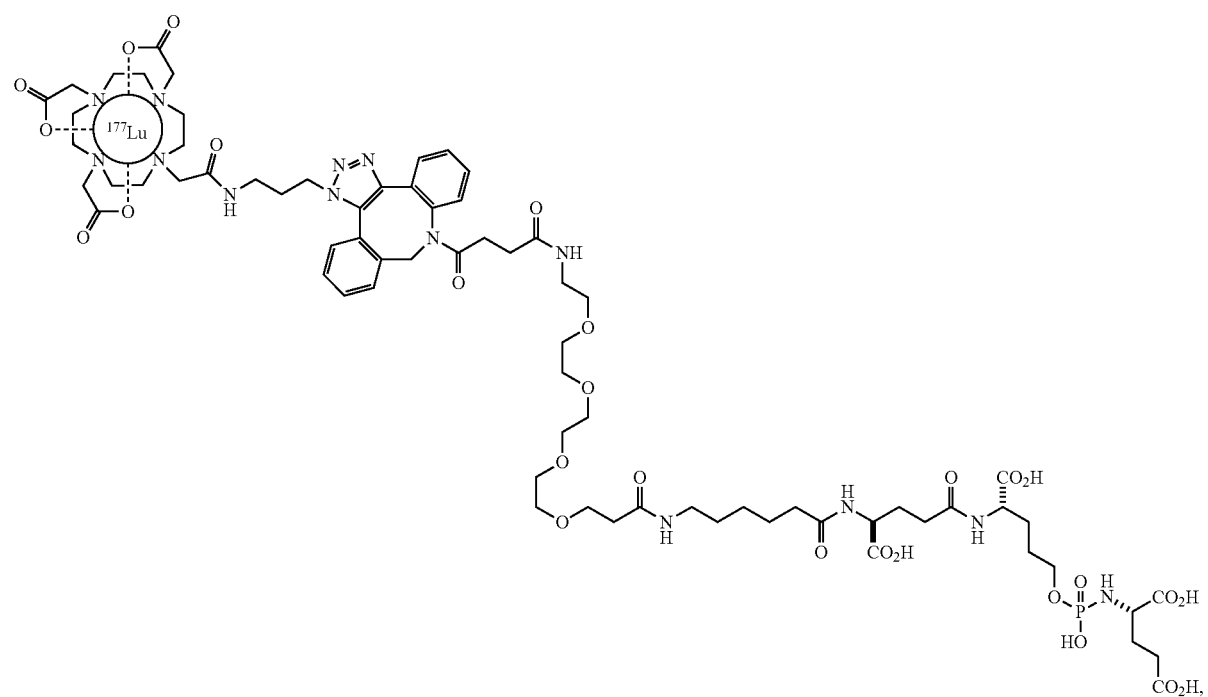

the method comprising reacting an azide-containing chelating agent associated with a PET-active or therapeutic radioisotope of the structure
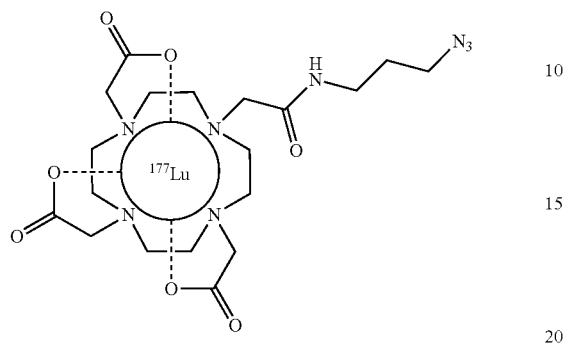
with a alkyne-modified PMSA inhibitor of the structure
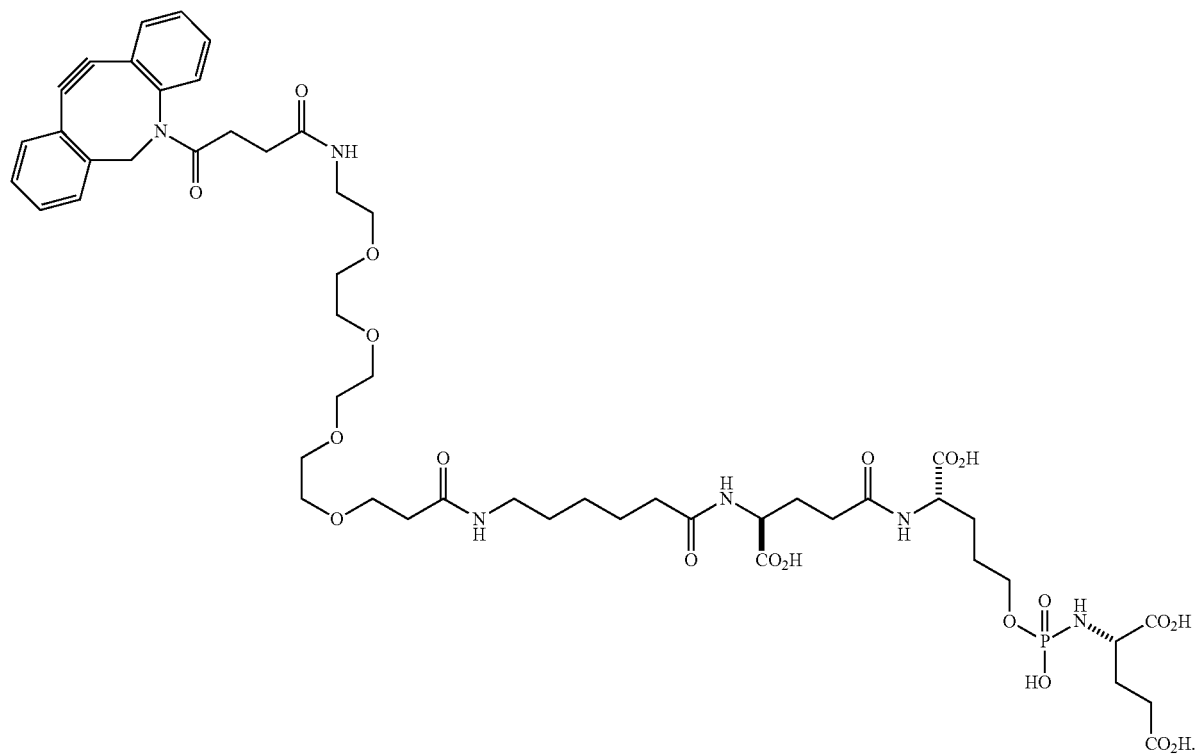
EXAMPLES
Example 1
Preparation of CTT1402
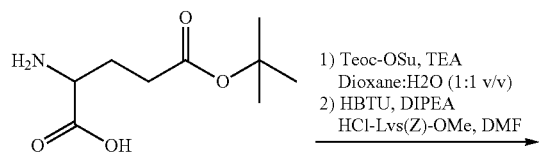
1) Teoc-OSu, TEA
   Dioxane:H2O (1:1 v/v)
2) HBTU, DIPEA
   HCl-Lys(Z)-OMe, DMF -continued
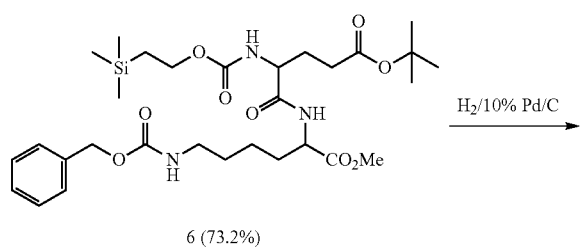
6 (73.2%)
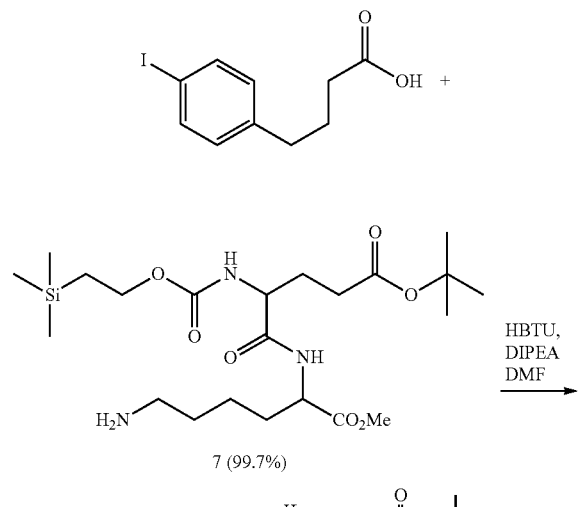
7 (99.7%)
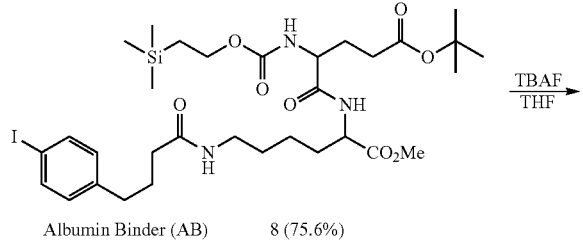
Albumin Binder (AB)    8 (75.6%)
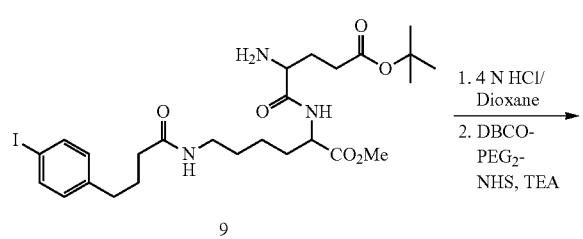
9
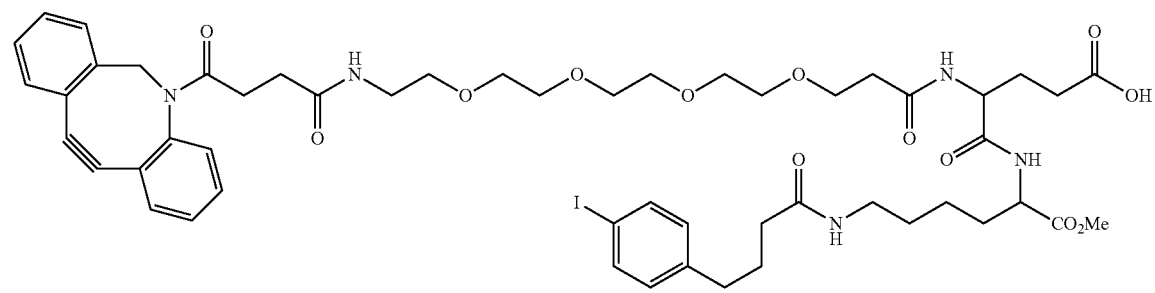
11 (41.5%, over 3 steps)

-continued

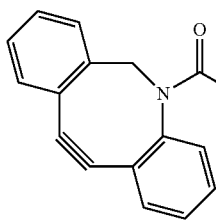
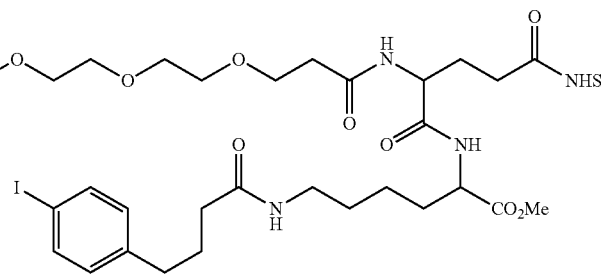

12

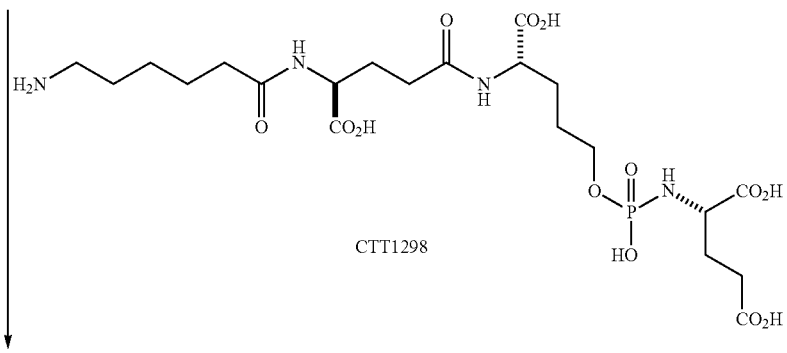

CTT1298

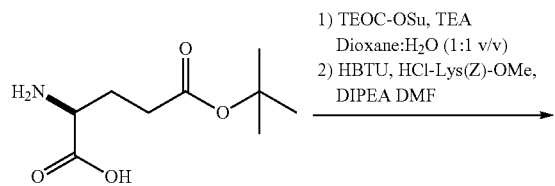

(30.9%, over 2 steps)

Chemical Formula: $C_{73}H_{101}IN_9O_{25}P$
Molecular Weight: 1662.51

CTT-1402-OMe

Methyl ester left on the albumin binder motif

Details of Synthesis:

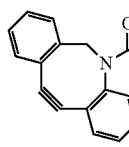

1) TEOC-OSu, TEA
Dioxane:H$_2$O (1:1 v/v)
2) HBTU, HCl-Lys(Z)-OMe, DIPEA DMF

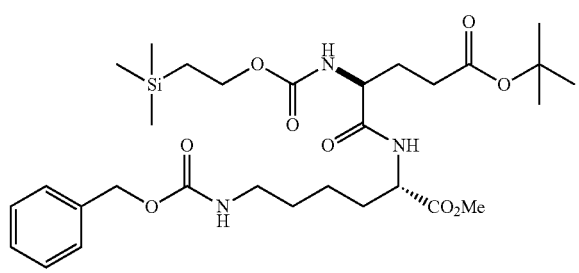

6

Step 1: Synthesis of (8S,11S)-methyl 11-(4-(((benzyloxy)carbonyl)amino)butyl)-8-(3-(tert-butoxy)-3-oxopropyl)-2,2-dimethyl-6,9-dioxo-5-oxa-7,10-diaza-2-siladodecan-12-oate (6)

Step a: To a stirred solution of Glu-(OtBu)-OH (2.089 g, 10.28 mmol) and triethylamine (0.2.15 mL, 15.43 mmol) in 1:1 Dioxane:water (v/v) (31 mL) Teoc-OSu (3.2 g, 12.34 mmol) was added in one portion. The mixture is stirred at room temperature overnight, then diluted with water (15 mL), acidified with 4 N HCl and 1 N HCl, and extracted with ethyl acetate (3×40 mL). The combined organic layers are washed with brine (60 mL), dried with magnesium sulfate, filtered and evaporated to give a crude oil (3.451 g, 96.6% yield) and dried overnight.

Step b: To the resultant crude solution (3.451, 9.929 mmol) in 20 mL of anh. DMF was added HBTU (3.765 g, 9.929 mmol) in one portion and stirred at room temperature for 30 min under inert atmosphere. After 30 min, to the reaction mixture, a solution of HCl-Lys(Z)-OMe (3.941 g, 11.914 mmol) and diisopropylethylamine (4.323 mL, 24.822 mmol) in 30 mL of anh. DMF was added drop-wise and stirred overnight at room temperature under inert atmosphere. Upon overnight stirring, the reaction mixture was taken up in ethyl acetate (100 mL) and the organic layer was washed with 1 N HCl (2×, 75 mL), followed by 10% NaHCO$_{3(aq)}$ (wt/v) (2×, 75 mL), then brine (1×, 75 mL). The organic layer was dried with magnesium sulfate, filtered and evaporated. The desired compound 6 was obtained via silica chromatography (Silicycle 40 g cartridge) with 1:1 EtOAc:Hex (Rf=0.33) as the eluent (4.698 g, 75.9%; 73.2% over 2 steps).

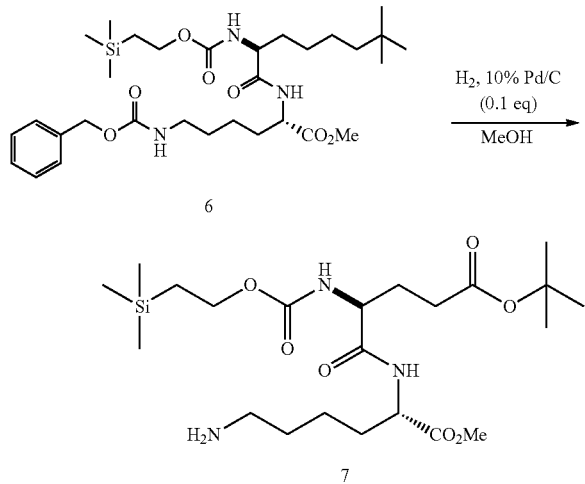

Step 2: Synthesis of (8S,11S)-methyl 11-(4-aminobutyl)-8-(3-(tert-butoxy)-3-oxopropyl)-2,2-dimethyl-6,9-dioxo-5-oxa-7,10-diaza-2-siladodecan-12-oate (7)

10% Pd/C (0.797 g, 0.751 mmol) was added to a stirring solution of 6 (4.690 g, 7.518 mmol) in 70 mL of methanol at room temperature. The resultant solution was subjected to $H_{2(g)}$ atmosphere with a double-layered balloon and stirred overnight. Upon overnight stirring, the reaction was complete and filtered through a celite plug and concentrated down to give 7 in quantitative yield (3.670 g, 99.7%).

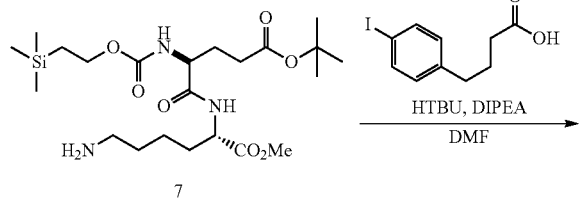

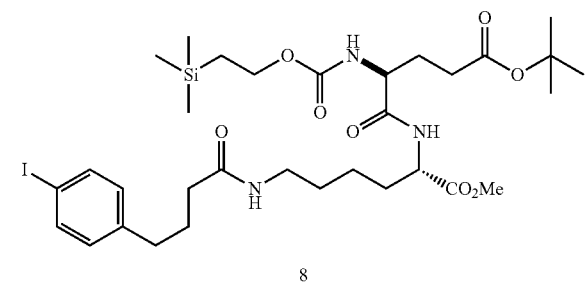

Step 3: Synthesis of (8S,11S)-methyl 8-(3-(tert-butoxy)-3-oxopropyl)-11-(4-(4-(4-iodophenyl)butanamido)butyl)-2,2-dimethyl-6,9-dioxo-5-oxa-7,10-diaza-2-siladodecan-12-oate (8)

To a solution of 4-(4-iodophenyl)butanoic acid (0.547 g, 1.89 mmol) in 7 mL of anh. DMF was added HBTU (0.716 g, 1.89 mmol) in one portion and stirred at room temperature for 30 min under inert atmosphere. After 30 min, to the reaction mixture, a solution of 7 (0.770 g, 1.57 mmol) and N,N-diisopropylethylamine (0.410 mL, 2.35 mmol) in 8 mL of anh. DMF was added drop-wise and stirred overnight at room temperature under inert atmosphere. Upon overnight stirring, the reaction mixture was taken up in ethyl acetate (100 mL) and the organic layer was washed with 1 N HCl (2×, 75 mL), followed by 10% $NaHCO_{3(aq)}$ (wt/v) (2×, 75 mL), then brine (1×, 75 mL). The organic layer was dried with magnesium sulfate, filtered and evaporated. The desired compound 8 was obtained via silica chromatography (Silicycle 40 g cartridge) with 65% EtOAc:Hex as the eluent (TLC developed with 75% EtOAc:Hex, Rf=0.33 with) (0.905 g, 75.6%).

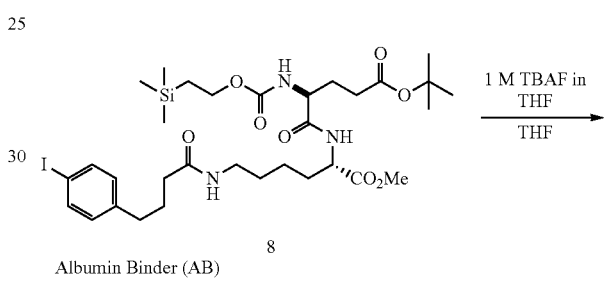

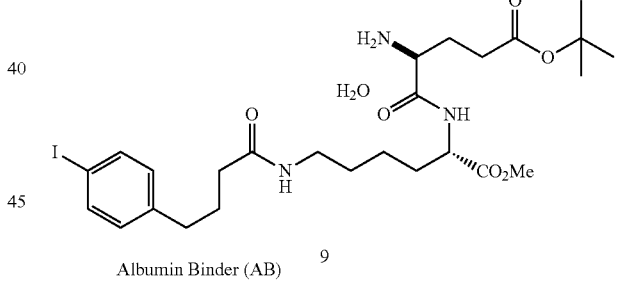

Step 4: Synthesis of (S)-methyl 2-((S)-2-amino-5-(tert-butoxy)-5-oxopentanamido)-6-(4-(4-iodophenyl)butanamido)hexanoate (9)

1 M TBAF in THF (1.864 mL, 1.864 mmol) was added to at stirring solution of 8 (0.710 g, 0.932) in 9 mL of anhydrous THF at room temperature under inert atmosphere. The resultant solution was heated to 44° C. and stirred until completion, approximately 5 hrs. Upon completion, the reaction was cooled to room temperature and quenched with 5% $KHCO_{3(aq)}$ (wt/v) (15 mL) and extracted with ethyl acetate (2×, 50 mL). The combined organic layers were washed with brine (2×, 25 mL), dried with magnesium sulfate, filtered and evaporated and the crude was used in the next step without further purification (TLC developed in 20% MeOH:EtOAc, Rf=0.33) (0.5538 g, 96.1%).

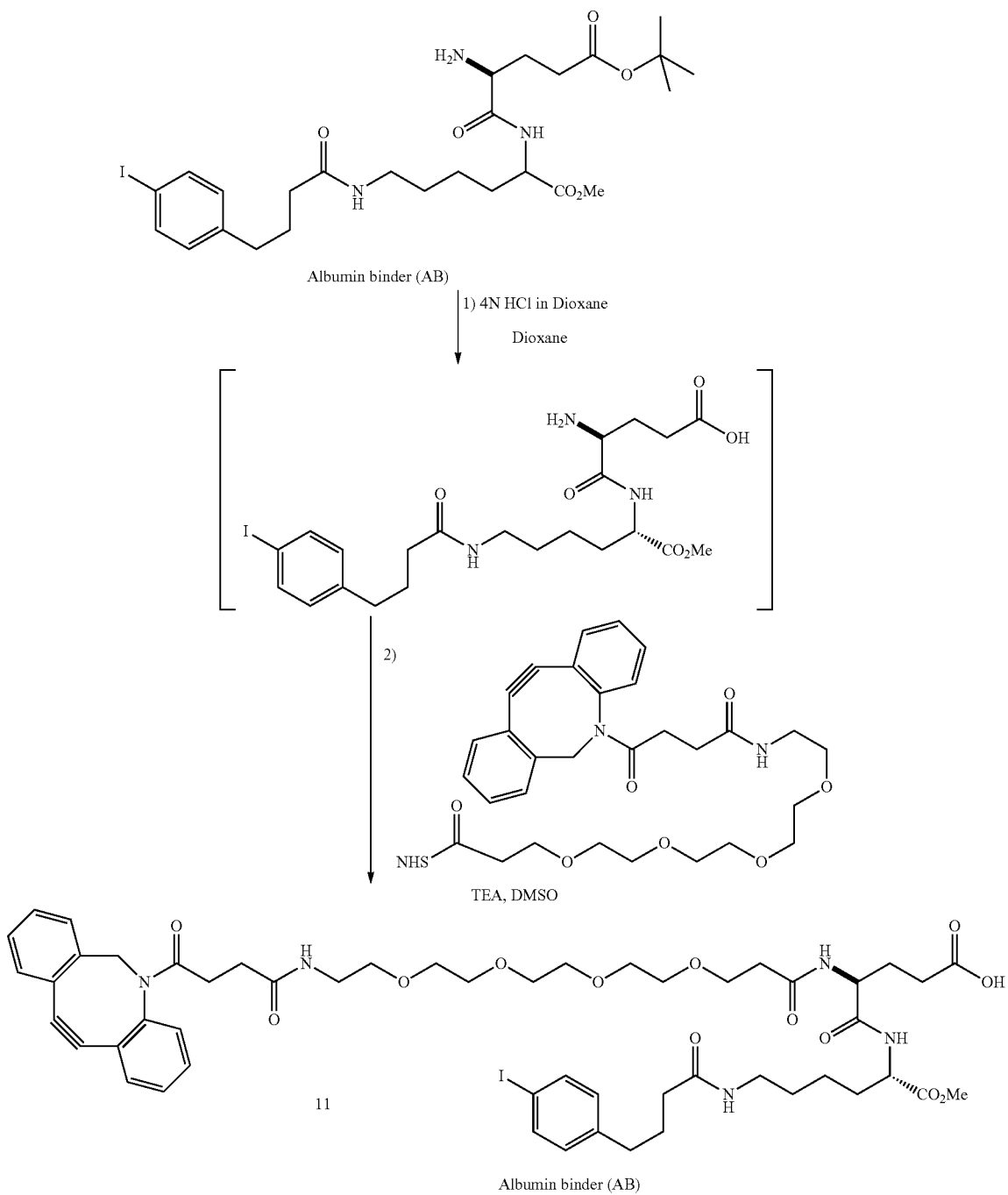

Step 5: Synthesis of DBCO-PEG₄-(S)-4-amino-5-(((S)-6-(4-(4-iodophenyl)butanamido)-1-methoxy-1-oxohexan-2-yl)amino)-5-oxopentanoic Acid (11)

Step a: 4 N HCl in Dioxane (5.0 mL, 20.08 mmol) was added dropwise to a solution of 9 (0.310 g, 0.502 mmol) in 5.0 mL of anhydrous Dioxane at 4° C. for 30 mins then allowed to warm to room temperature. After 3 hrs, another aliquot of 4 N HCl in Dioxane (2.5 mL, 10.04 mmol) was added at room temp. Upon completion (approximately additional 30 min), the reaction was concentrated down and dried overnight under high vacuum and used in the next step without further purification.

Step b: DBCO-PEG₄-NHS (0.300 g, 0.462 mmol) in 2 mL of anhydrous Dioxane was added dropwise to the crude carboxylic acid (0.502 mmol) mixture from step 1 and TEA (0.104, 0.753 mmol) in 1.0 mL of anhydrous DMSO and 4 mL of anhydrous Dioxane under inert atmosphere. The resulting solution was stirred overnight. Upon over night stirring, the reaction was taken up in 100 mL of EtOAc and washed with 1 N HCl (50 mL). The combined organic layer was collected and the aqueous layer was back extracted with EtOAc (100 mL). The combined organic layer was dried with MgSO₄, filtered and evaporated down. Compound 11 was isolated with a 0-4% H₂O in 3:7 ACN:MeOH gradient to yield a foamy pinkish orange solid (0.228 g, 41.5%, over 2 steps). m/Z calculated for $C_{52}H_{66}IN_5NaO_{13}$ [M+Na] 1118.36; found [M+Na] 1118.56 (low-Res MALDI).
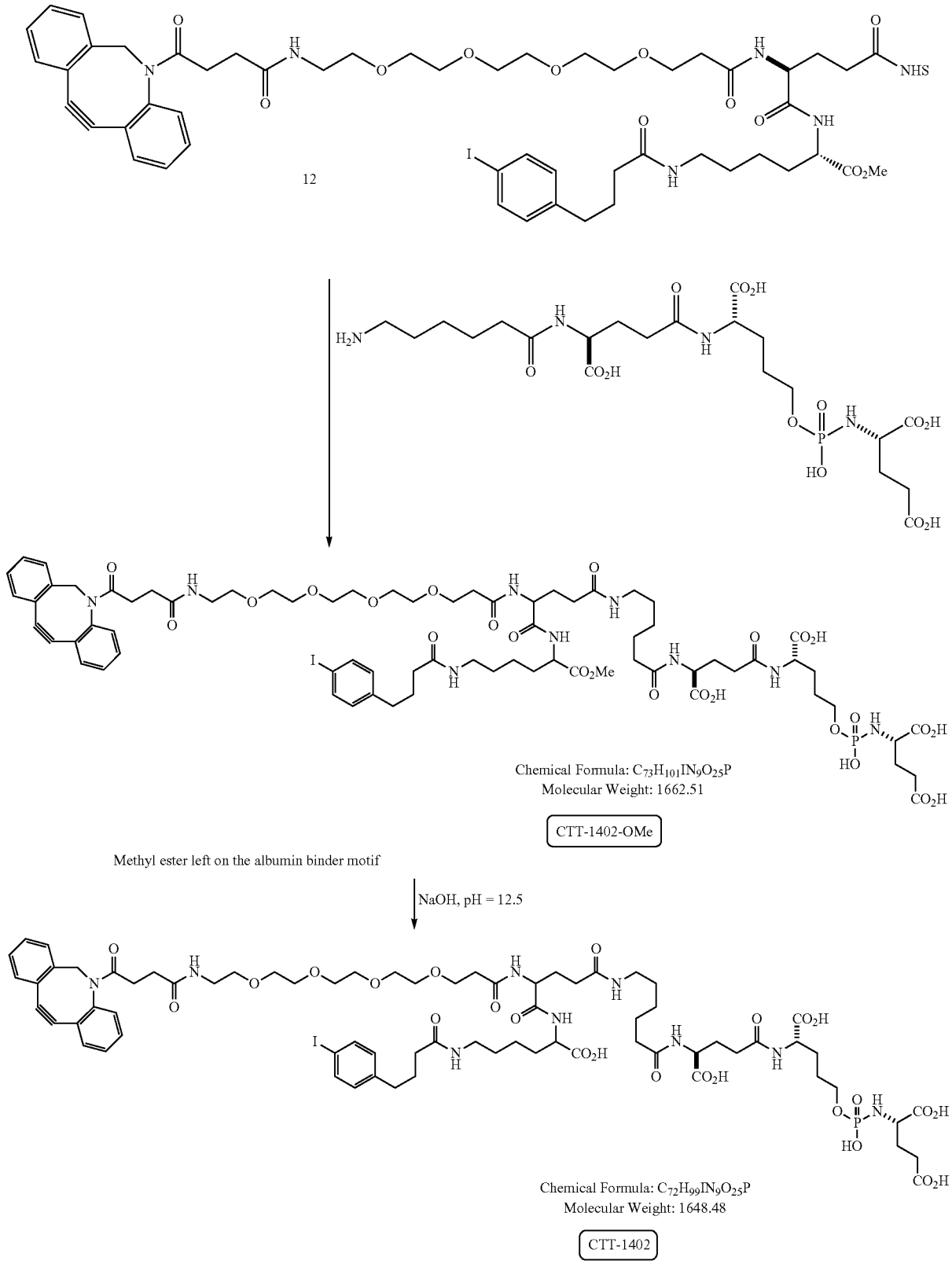

Step 6: Synthesis of CTT-1402-OMe

Step a: EDCI-HCl (0.029 g, 0.153 mmol) followed by N-hydroxysuccinamide (0.014 g, 0.122 mmol) was added to a solution of 11 (0.067 g, 0.061 mmol) in 1.0 mL of anhydrous DMF under inert atmosphere. The reaction was stirred for 1 hr at 50° C. and another aliquot of EDCI-HCl (0.029 g, 0.153 mmol) and N-hydroxysuccinamide (0.014 g, 0.122 mmol) was added and stirred until completion. The crude mixture was diluted with 20 mL of EtOAc and washed with 1 N HCl (aq) to removed unreacted EDCI-HCl. The organic layer was dried through a pad of anhydrous sodium sulfate and concentrated down to yield a glassy pink solid. The solid, 12, was dried under high vacuum for an hr and used in the next step without further purification.

Step b: Compound 12 in 1 mL of anhydrous DMF was added dropwise to a stirring solution of CTT 1298 (0.419 mL, 0.108 mmol) in 0.839 mL of 1 M TEA-Bicarbonate at 4° C. The resulting solution was stirred overnight at 4° C. The desired compound CTT-1402-OMe was obtained via RP-Prep HPLC with a 10-85% ACN (29.6 mg, 30.9%). Sodium bicarbonate (1.2 eq) was added to neutralize the ammonium acetate in the fractions. The ACN was removed by rotary evaporation with minimal heating, and the remaining water was lyophilized. The yield was determined with a spectrophotometer at 310 nm, $\varepsilon_{310}=11{,}000$ $M^{-1}Lcm^{-1}$. The purity for CTT-1402 was determined to be greater than 96% by HPLC for all batches based on percent area. large peaks at 4.8 ppm and 1.8 ppm are HOD and Acetate peaks respectively.

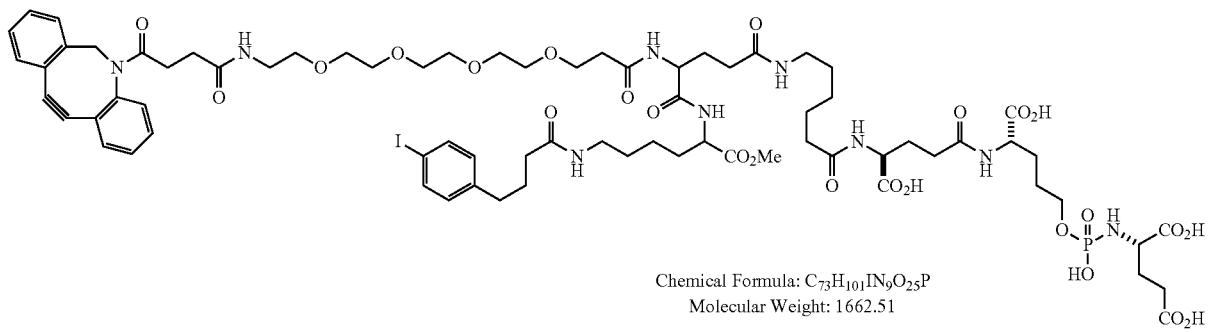

Chemical Formula: $C_{73}H_{101}IN_9O_{25}P$
Molecular Weight: 1662.51

CTT-1402-OMe

Methyl ester left on the albumin binder motif

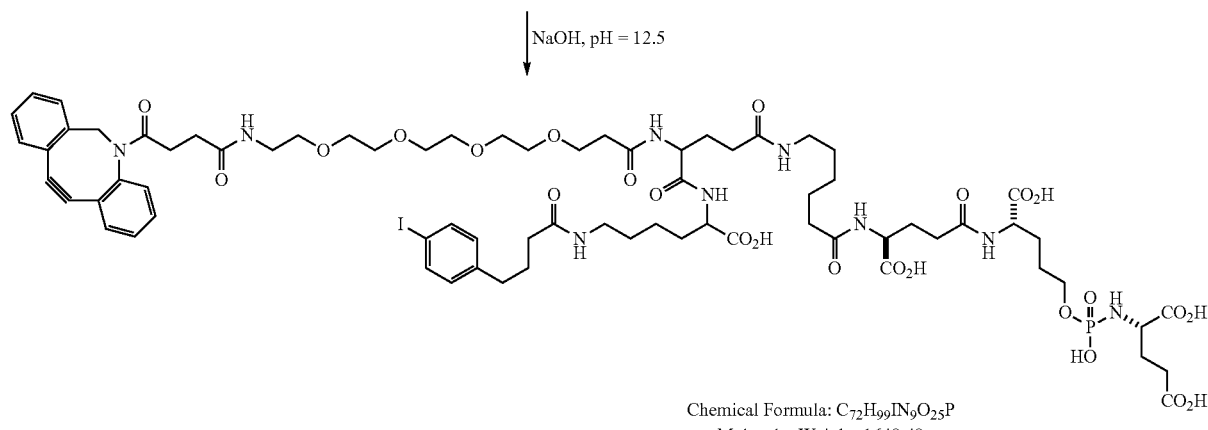

Chemical Formula: $C_{72}H_{99}IN_9O_{25}P$
Molecular Weight: 1648.48

CTT-1402

Step 7: Synthesis of CTT-1402

CTT-1402-OMe was dissolved in 0.9 mL of MQ water. An aqueous solution of sodium hydroxide (1 N) was added until the pH of the solution was 12.5 and stirred overnight at room temperature. The final compound, CTT-1402, was obtained via RP-Prep HPLC with a 10-85% ACN (16.3 mg, 54.7%). Sodium bicarbonate (1.2 eq) was added to neutralize the ammonium acetate in the fractions. The ACN was removed by rotary evaporation with minimal heating, and the remaining water was lyophilized. The yield was determined with a spectrophotometer at 310 nm, $\varepsilon_{310}$=11,000 $M^{-1}Lcm^{-1}$.

Analytical of CTT1402 (Purity and Identity)

At the penultimate step CTT-1402 was analyzed via $^1$H NMR, $^{31}$P NMR, HRMS-MALDI and HPLC.

HPLC Conditions

Analytical HPLC:
 Column: Phenomenex Luna 5 urn C18(2) 100 Å (cat. No. 00F-4252-E0)
 Dimensions: 150×4.6 mm
 Wavelength: 310 nM

| Time | Percent 10 mM NH$_4$OAc | Percent ACN | Flow Rate (mL/min) |
|---|---|---|---|
| 0.0 | 90 | 10 | 1 |
| 5.0 | 90 | 10 | 1 |
| 15.0 | 5 | 95 | 1 |
| 20.0 | 5 | 95 | 1 |
| 22.0 | 90 | 10 | 1 |
| 30.0 | 90 | 10 | 1 |

Prep HPLC:
 Column: Phenomenex Luna 10 um C18(2) 100 Å (cat. No. 00B-4253-P0-AX)
 Dimensions: 50×21.2 mm
 Wavelength: 310 nM

| Time | Percent 10 mM NH$_4$OAc | Percent ACN | Flow Rate (mL/min) |
|---|---|---|---|
| 0.0 | 90 | 10 | 15 |
| 5.0 | 90 | 10 | 15 |
| 20.0 | 15 | 85 | 15 |
| 20.1 | 5 | 95 | 15 |
| 25.0 | 5 | 95 | 15 |
| 25.1 | 90 | 10 | 15 |
| 30.0 | 90 | 10 | 15 |

Analytical HPLC and MS methods were developed to characterize the CTT1402 compound and confirmed the CTT1402 structure and purity as greater than 96%.

Final Structure and Composition of CTT1402

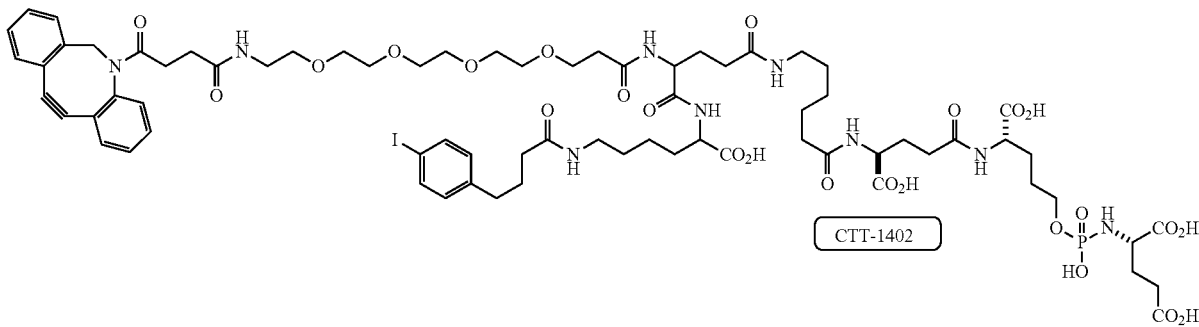

(4S,9S,24S)-21-(20-(11,12-didehydrodibenzo[b,f]azocin-5(6H)-yl)-17,20-dioxo-4,7,10,13-tetraoxa-16-azaicosanamido)-1-(((((S)-1,3-dicarboxypropyl)amino)(hydroxy)phosphoryl)oxy)-33-(4-iodophenyl)-6,11,18,22,30-pentaoxo-5,10,17,23,29-pentaazatritriacontane-4,9,24-tricarboxylic acid Chemical Formula: $C_{72}H_{99}IN_9O_{25}P$
Exact Mass: 1647.55
Molecular Weight: 1648.48
Elemental Analysis: C, 52.46; H, 6.05; I, 7.70; N, 7.65; O, 24.26; P, 1.88

$^1$H NMR (600 MHz, D$_2$O) δ 8.46 (s, 1H), 7.51 (d, J=7.7 Hz, 2H), 7.36-7.12 (m, 8H), 7.05 (d, J=7.4 Hz, 2H), 6.70 (d, J=7.8 Hz, 2H), 4.87 (d, J=14.1 Hz, 1H), 4.35 (t, J=7.2 Hz, 1H), 4.13 (dddd, J=17.6, 13.5, 8.7, 4.9 Hz, 3H), 3.76 (q, J=6.3 Hz, 2H), 3.66 (q, J=5.9 Hz, 2H), 3.54-3.40 (m, 12H), 3.31 (d, J=13.9 Hz, 2H), 3.12 (dt, J=31.2, 7.2 Hz, 5H), 3.03-2.93 (m, 2H), 2.48 (d, J=5.9 Hz, 2H), 2.40-2.17 (m, 12H), 2.15-2.04 (m, 4H), 1.88-1.78 (m, 7H), 1.74-1.56 (m, 8H), 1.54-1.40 (m, 5H), 1.36-1.27 (m, 5H). $^{31}$P NMR (243 MHz, D20) δ 7.47. HRMS (MALDI): m/z calculated for C$_{72}$H$_{98}$IN$_9$O$_{25}$P [M−H] 1646.5456; found 1646.5381

Preparation of Radiolabeled CTT1403

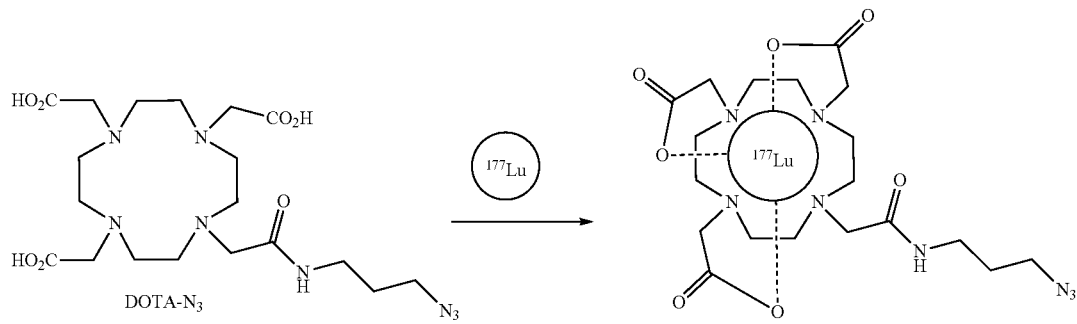

Solution A: 20 mM CTT1402 in 0.4 M NH$_4$OAc (pH=7)

Solution B: 5.3 mM DOTA-azide (Macrocyclics, Dallas, Tex., B-288) in 0.4 M NH$_4$OAc Solution C: 56 mM gentisic acid in 0.4 M NH$_4$OAc (pH=7)

Preparation of $^{177}$Lu-DOTA-Azide

Mix solution B (10 μL, 53 nmol DOTA-azide), solution C (10 μL, 0.56 μmol gentisic acid) and $^{177}$LuCl$_3$ (10 μL, 14.6 mCi) in 0.5 M NH$_4$OAc buffer (150 μL, pH=4.85). The resulting mixture was heated at 95° C. for 1 h.

For quality control, a small aliquot (1 μL) of the mixture was diluted with 0.5 M NH$_4$OAc buffer (20 μL, pH=4.85) before injection for HPLC analysis. High radiolabeling yield (>95%), high radiolabeling purity (>95%) and specific activity (10.2 Gbq/μmol) were observed.

HPLC Conditions are Listed Below:

| Time  | Flow | % A  | % B  |
|-------|------|------|------|
| 0.01  | 1.00 | 99.0 | 1.0  |
| 5.00  | 1.00 | 99.0 | 1.0  |
| 10.00 | 1.00 | 90.0 | 10.0 |
| 14.00 | 1.00 | 90.0 | 10.0 |
| 15.00 | 1.00 | 99.0 | 1.0  |
| 15.10 | 0.00 | 99.0 | 1.0  |

Preparation of $^{177}$Lu-CTT1403 for Therapy Study.

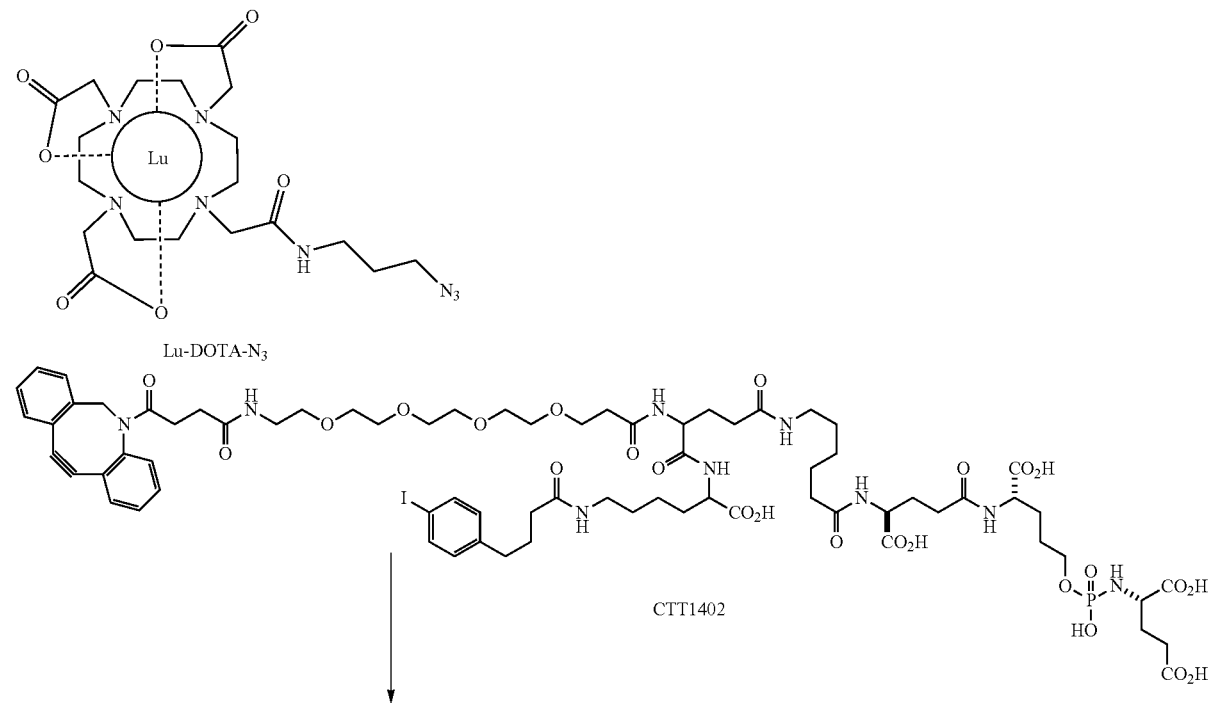

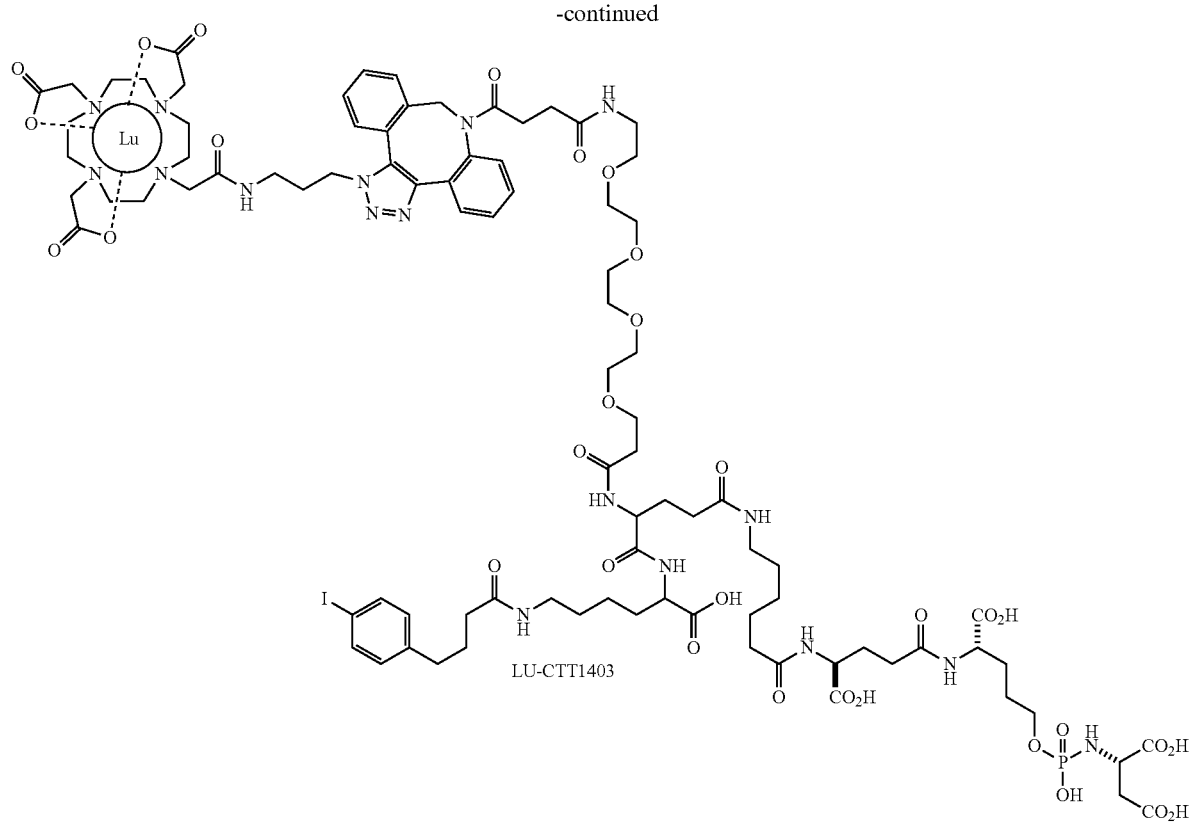

LU-CTT1403

Solution A (17 μL, 0.34 μmol CTT1402) was added to the $^{177}$Lu-DOTA-Azide mixture. The resulting mixture was heated at 37° C. for 1 h before HPLC separation. Fractions containing the highest radio activities were combined and evaporated using nitrogen flow at 42° C. to around 0.41 mL (9.07 mCi). The salt concentration of the remaining solution was adjusted using saline (720 μL).

For quality control, a small aliquot (10 μL) of the mixture was used for HPLC analysis. According to the HPLC results, high conversion rate of 177Lu-DOTA-Azide (>95%), high radiolabeling yield (>95%), and high radiolabeling purity (>95%) were observed.

| Time | Flow | % A | % B |
|---|---|---|---|
| 0.01 | 1.00 | 95.0 | 5.0 |
| 3.00 | 1.00 | 95.0 | 5.0 |
| 28.00 | 1.00 | 5.0 | 95.0 |
| 32.00 | 1.00 | 5.0 | 95.0 |
| 33.00 | 1.00 | 95.0 | 5.0 |
| 38.00 | 1.00 | 95.0 | 5.0 |
| 38.01 | 0.00 | 95.0 | 5.0 |

Preparation of Cold Lu-CTT1403 Standard

Solution A: 20 mM CTT1402 in 0.4 M NH$_4$OAc (pH=7)

Solution B: 5.3 mM DOTA-azide (Macrocyclics, Dallas, Tex., B-288) in 0.4 M NH$_4$OAc Solution C: 20 mM LuCl$_3$ in 0.4 M NH$_4$OAc (pH=7)

Preparation of Cold Lu-DOTA-Azide

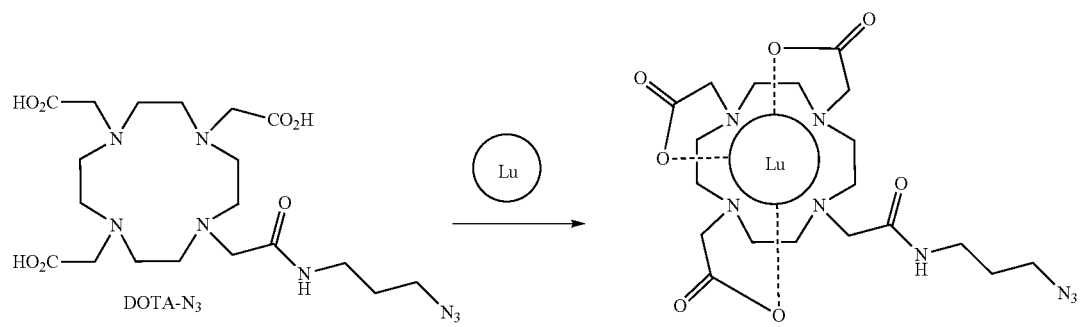

Mix solution B (10 µL, 53 nmol DOTA-azide) and solution C (10 µL, 0.2 µmol LuCl$_3$) in 0.5 M NH$_4$OAc buffer (150 µL, pH=4.85). The resulting mixture was heated at 95° C. for 1 h.
Preparation of Cold Lu-CTT1403 Standard
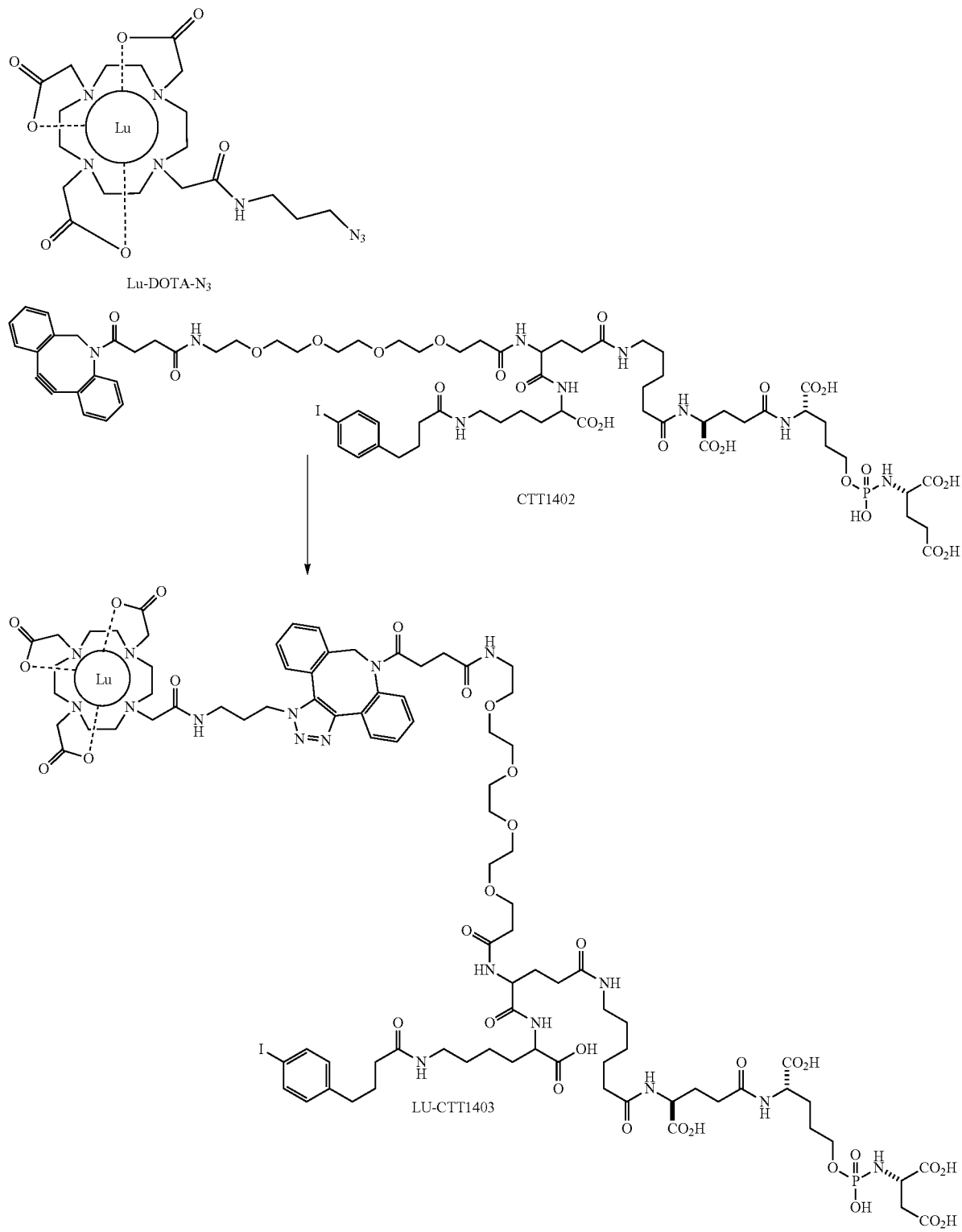

Solution A (17 µL, 0.34 µmol CTT1402) was added to the Lu-DOTA-Azide mixture. The resulting mixture was heated at 37° C. for 1 h before HPLC separation. A small sample was diluted with water for ESI-MS. Found m/z=1165.35408, calcd. for C91H131ILuN17NaO32P2+m/z (M+H+Na)2+= 1165.36282.

CTT1403 without Lu was prepared similarly using DOTA-Azide only.

Analytical of CTT1403 (Purity and Identity)

HPLC Analytical Conditions:

|   | Time | Flow | % A | % B |
|---|------|------|-----|-----|
| 1 | 0.01 | 1.00 | 95.0 | 5.0 |
| 2 | 3.00 | 1.00 | 95.0 | 5.0 |
| 3 | 28.00 | 1.00 | 5.0 | 95.0 |
| 4 | 32.00 | 1.00 | 5.0 | 95.0 |
| 5 | 33.00 | 1.00 | 95.0 | 5.0 |
| 6 | 38.00 | 1.00 | 95.0 | 5.0 |
| 7 | 38.01 | 4.00 | 95.0 | 5.0 |

Final Structure and Composition of CTT1403

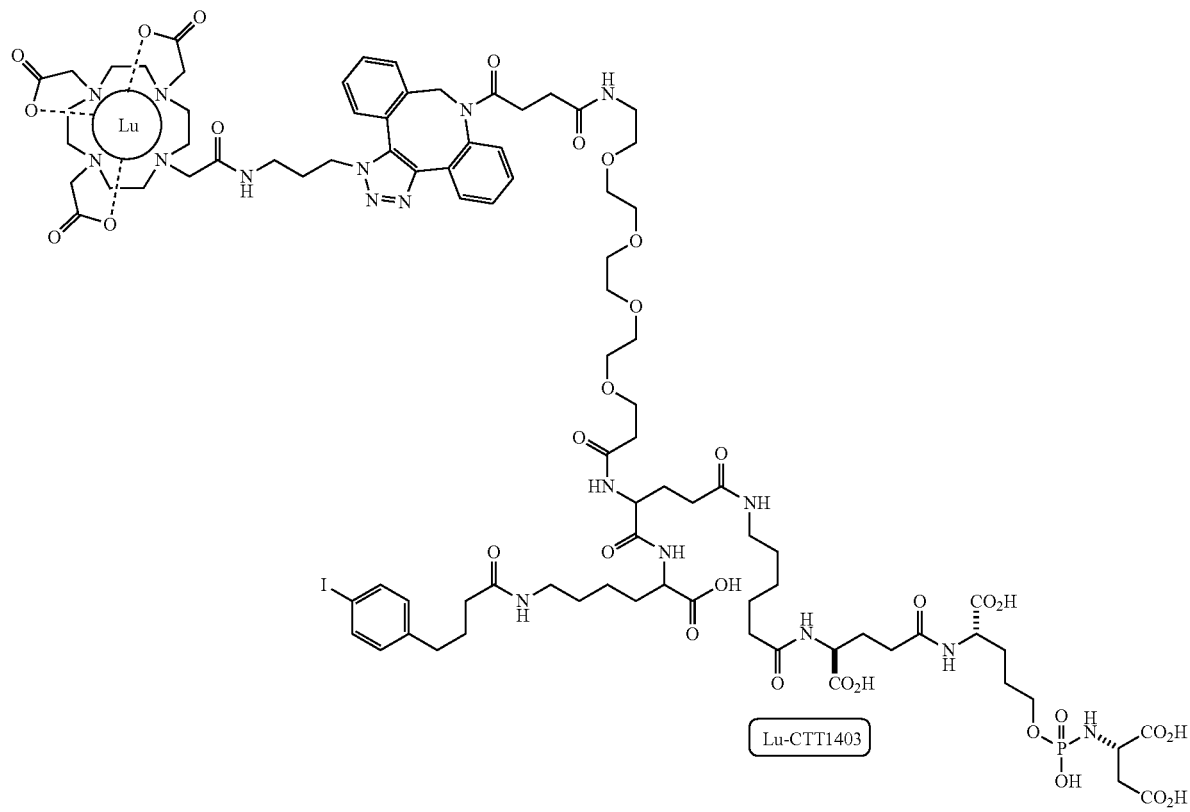

Chemical Formula: $C_{91}H_{130}ILuN_{17}O_{32}P$
Exact Mass: 2305.7258
Molecular Weight: 2306.9730
Elemental Analysis: C, 47.38; H, 5.68; I, 5.50; Lu, 7.58; N, 10.32; O, 22.19; P, 1.34

CTT1400 was synthesized from CTT1298 with an overall yield of 42.65%

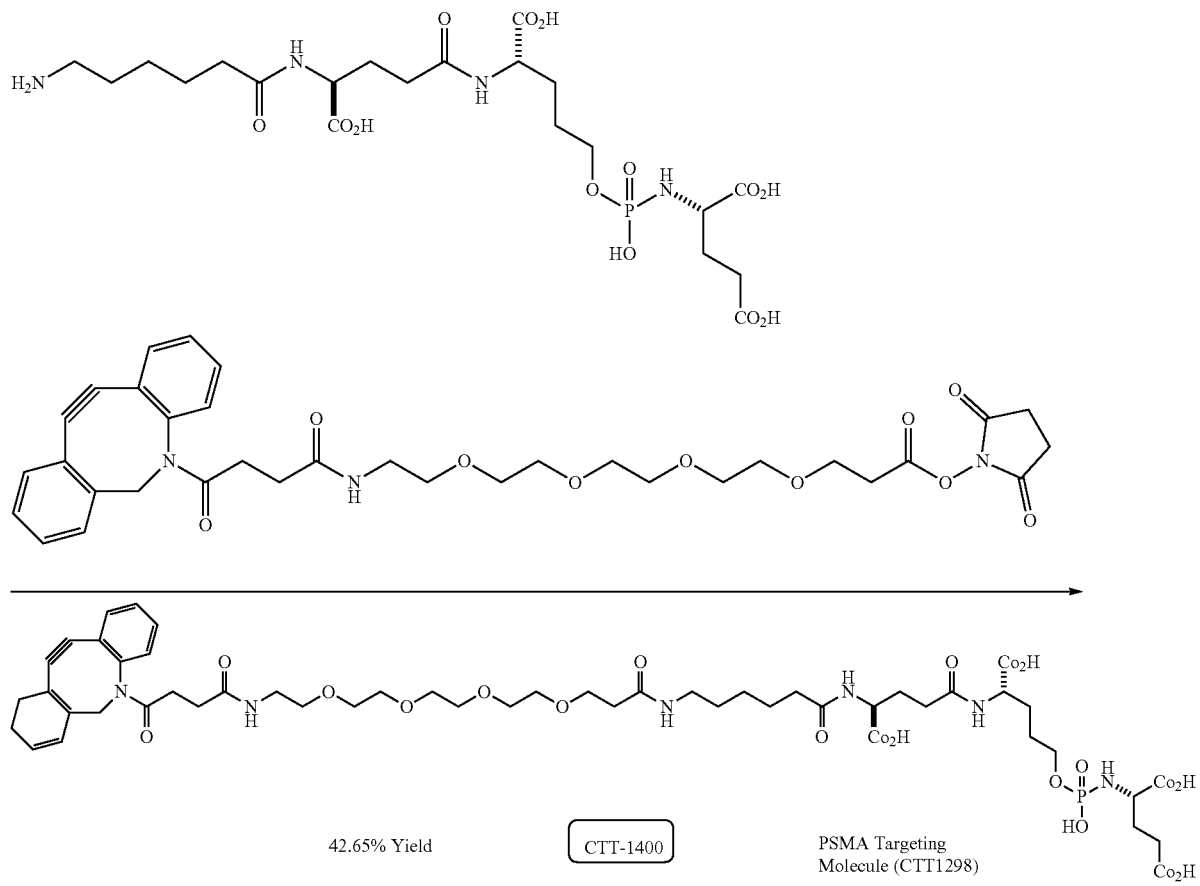

| Compound | Quantity |
|---|---|
| 0.43M CTT1298 | 125 μL (25 mg) |
| 1M TEA Bicarb buffer | 200 μL |
| 0.26M DBCO-PEG4-NHS | 300 μL (50 mg) |

CTT1298 was dissolved in ddH$_2$O to make a 0.43M solution. 125 μL of this solution was added to a 1 mL conical vial. 1M TEA-Bicarb buffer was added to the 1 mL conical vial containing the CTT1298 solution. 1.8 equivalents of DBCO-PEG4-NHS was dissolved in DMSO (to make a 0.26M solution) and added to the vial dropwise. This reaction stirred vigorously overnight at 4° C. The reaction was then purified via prep HPLC and dried down through lyophilization. Before lyophilization, 1.2 equivalents of NaHCO$_3$ were added to neutralize the pH. The product was quantified by UV absorbance. Confirmation of the desired product was achieved through MS and analytical HPLC methods. Weight: 20.43 mg, yield: 42.65%.

Analytical Analysis of CTT1400 (Purity and Identity)

Analytical HPLC, $^1$H & $^{31}$P NMR, and MS methods were developed to characterize the CTT1400 compound and confirmed the CTT1400 structure and purity was confirmed at >99% for each of the batches produced.

$^1$H NMR (400 MHz, D$_2$O) δ 7.45 (d, J=7.4, 1H), 7.36-7.20 (m, 6H), 7.16 (dd, J=7.3, 1.6 Hz, 1H), 4.91 (d, J=14.3 Hz, 1H), 3.95 (ddd, J=13.9, 8.5, 4.9 Hz, 2H), 3.58 (ddd, J=9.6, 5.6, 3.3 Hz, 5H), 3.51-3.38 (m, 12H), 3.33 (dt, J=9.1, 6.2 Hz, 1H), 3.07 ? 2.88 (m, 4H), 2.32 (t, J=6.1 Hz, 2H), 2.26-2.01 (m, 10H), 1.91 (d, J=0.7 Hz, 2H), 1.74-1.60 (m, 4H), 1.62-1.27 (m, 8H), 1.15 (p, J=7.6, 7.1 Hz, 2H). $^{31}$P NMR (162 MHz, D$_2$O) δ 7.39. HRMS (MALDI): m/z calculated for C$_{51}$H$_{72}$N$_6$O$_{20}$P$^-$ [M+H] 1119.4539; found 11.19.4542. FIRMS (MALDI) spectrum of CTT1400 Calculated for C$_{51}$H$_{70}$N$_6$O$_{20}$P$^-$ m/z [M−H]=1117.4388; Found m/z=1117.1624

Final Structure and Composition of Precursor CTT1400

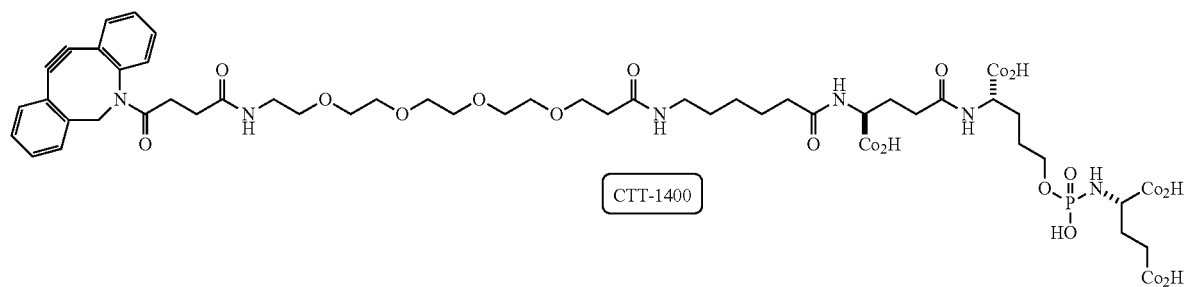

(2S)-2-(((((29S,34S)-29,34-dicarboxy-1-(11,12-didehydrodibenzo[b,f]azocin-5(6H)-yl)-1,4,20,27,32-pentaoxo-8,11,14,17-tetraoxa-5,21,28,33-tetraazaheptatriacontan-37-yl)oxy)(hydroxy)phosphoryl)amino)pentanedioic acid Chemical Formula: $C_{51}H_{71}N_6O_{20}P$
Exact Mass: 1118.45
Molecular Weight: 1119.11
Elemental Analysis: C, 54.74; H, 6.39; N, 7.51; O, 28.59; P, 2.77

Preparation of Radiolabeled CTT1401 $^{177}$Lu-labeled DOTA Azide was prepared and combined with CTT1400 to create CTT1401.

Solution A: 20 mM CTT1400 in 0.4 M $NH_4OAc$ (pH=7)
Solution B: 5.3 mM DOTA-azide (Macrocyclics, Dallas, Tex., B-288) in 0.4 M $NH_4OAC$
Solution C: 56 mM gentisic acid in 0.4 M $NH_4OAc$ (pH=7)

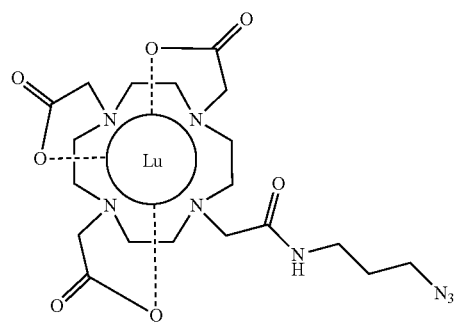

Lu-DOTA-$N_3$

-continued

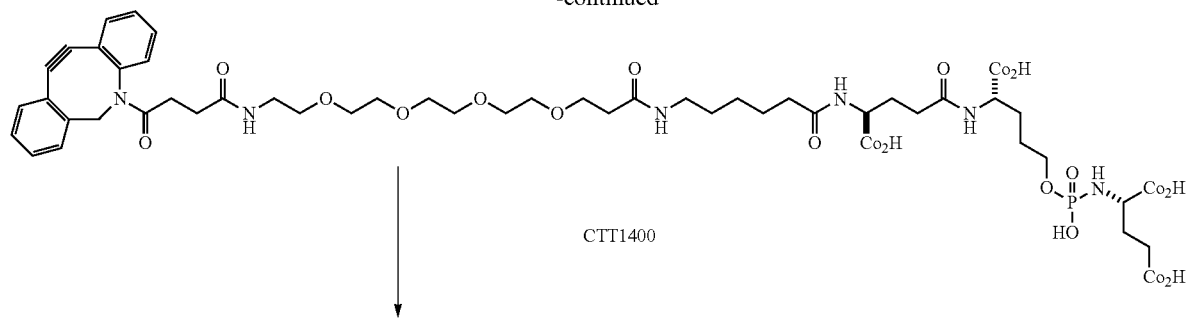

CTT1400

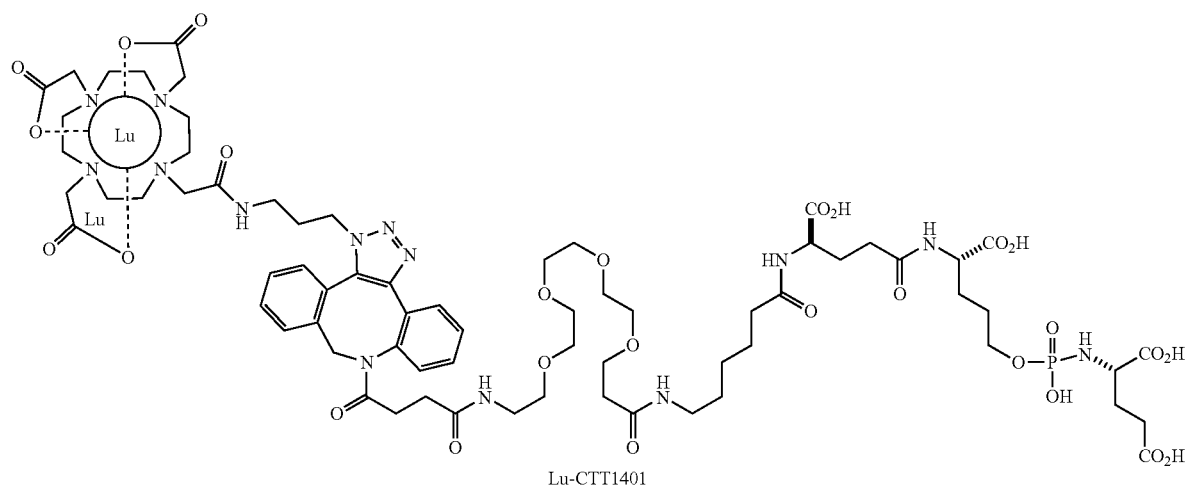

Lu-CTT1401

Solution A (17 µL, 0.34 µmol CTT1400) was added to the $^{177}$Lu-DOTA-Azide mixture. The resulting mixture was heated at 37° C. for 1 h before HPLC separation. $^{177}$Lu-CTT1401 fractions were collected in 200 µL portions. Fractions with the highest radio activities were consolidated into three samples. The first sample (2.24 mCi) was concentrated using nitrogen flow at 41° C. to approximately 130 µL remaining. The mixture was then separated into four tubes (30 µL, 500 µCi). Each tube was diluted with saline to 1.0 mL for injection (50 µCi/100 µL). The second sample (2.22 mCi) was processed similarly to generate another two tubes for injection and quality control HPLC. The last sample (2.49 mCi) was minimized and separated into five tubes. Each tube was adjusted to 250 µL and added sodium ascorbate (3.5 mM), gentisic acid (3.5 mM) and ethanol (10%) to minimize radiolysis. According to the HPLC results, high conversion rate of $^{177}$Lu-DOTA-Azide (>95%), high radiolabeling yield (>95%), and high radiolabeling purity (>95%) were observed.

CTT1401 Cold Standard (Purity and Identity)

HPLC Analytical Conditions

| Time | Flow | % A | % B |
|---|---|---|---|
| 0.01 | 1.00 | 99.0 | 1.0 |
| 5.00 | 1.00 | 99.0 | 1.0 |
| 10.00 | 1.00 | 90.0 | 10.0 |
| 15.00 | 1.00 | 90.0 | 10.0 |
| 25.00 | 1.00 | 80.0 | 20.0 |
| 35.00 | 1.00 | 80.0 | 20.0 |
| 50.00 | 1.00 | 70.0 | 30.0 |
| 55.00 | 1.00 | 70.0 | 30.0 |
| 60.00 | 1.00 | 1.0 | 99.0 |
| 65.00 | 1.00 | 99.0 | 1.0 |
| 70.00 | 1.00 | 99.0 | 1.0 |
| 70.01 | 0.00 | 99.0 | 1.0 |

MS (ESI) of cold CTT1.401: Found tri/z 1777.4727, calcd. for $C_{70}H_{104}LuN_{14}O_{27}P^+$ m/z $(M+H)^+=1777.6257$. Found m/z=889.2218, calcd. for $C_{70}H_{104}LuN_{14}O_{27}P^{2+}$ m/z $(M+2H)^{2+}=889.3165$.

Final Structure and Composition of CTT1401

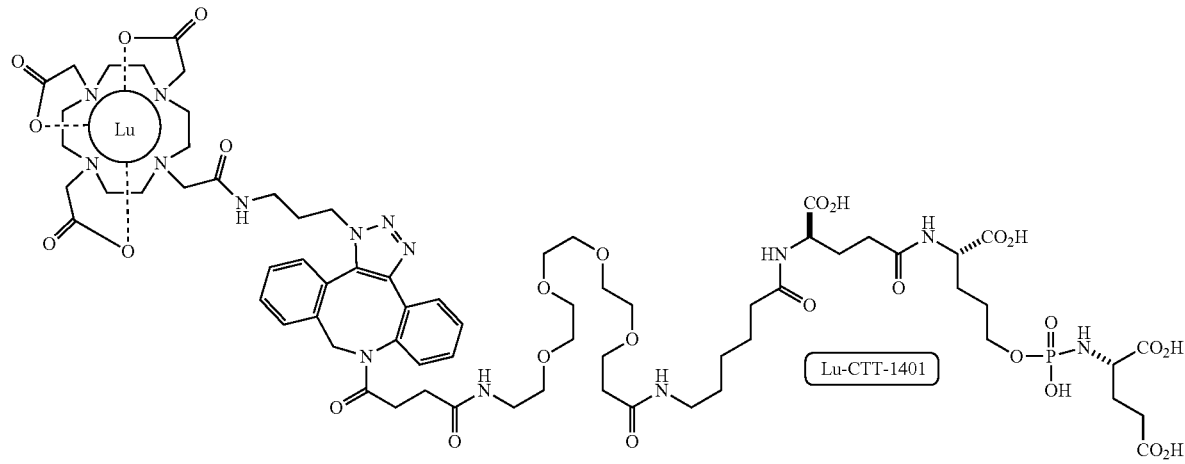

Chemical Formula: $C_{70}H_{102}LuN_{14}O_{27}P$
Exact Mass: 1776.6184
Molecular Weight: 1777.5976
Elemental Analysis: C, 47.30; H, 5.78; Lu, 9.84; N, 11.03; O, 24.30; P, 1.74

Purification of Radiotherapeutic Agents with Azide Resin

In order to remove any unlabeled PSMA targeting platforms, the reaction mixtures were applied to a SepPak cartridge packed with an azide-bearing resin. It is expected that all "un-clicked" PSMA targeting platforms will be scavenged by the azide resin. This clean-up step was optimized for efficient removal of the un-clicked PSMA targeting platform without loss of the desired assembled PSMA-targeted radiotherapeutic agents.

Azide-Agarose Resin Study Protocol:

Product Information:

Company: Click Chemistry Tools

Product Name: Azide-Agarose Product No.: 1038

Activation Level: 22.0 μmol alkyne groups per mL resin, supplied in a 50% slurry Support: 6% Cross-linked agarose Bead Size: Spherical, 50-150 μm Appearance: Off-white slurry Preservative: 20% Ethanol in water Procedure: Dissolve 5 mg DBCO-PEG$_4$-NHS ester in 800 μL DDH$_2$O and 200 μL DMSO (to improve solubility). Divide solution into 5 vials, each with 200 μL of solution. Added different amounts of resin to each vial:

Standard=0 μL resin 5 equivalents=350 μL resin 10 equivalents=700 μL resin 15 equivalents=1045 μL resin 20 equivalents=1400 μL resin Rock vials on a orbital rocker (no stir bars). Remove 15 μL aliquots from each vial after 15, 30, and 60 minutes. Push 15 μL aliquot through a 0.2 μm filter that had been activated with methanol. Run all purified samples on the analytical HPLC, with 5 μL injections

| % area decrease relative to standard | | |
|---|---|---|
| equivalents | % decrease at 15 min | % decrease at 30 min |
| 5 | 99.70909513 | 99.99502675 |
| 10 | 99.99759165 | 99.99991571 |
| 15 | 99.99954241 | 99.99997592 |
| 20 | 99.99913299 | 99.99931362 |
| equivalents | % left at 15 min | % left at 30 min |
| 5 | 0.29090487 | 0.004973247 |
| 10 | 0.002408352 | 8.42923E−05 |
| 15 | 0.000457587 | 2.40835E−05 |
| 20 | 0.000867007 | 0.00068638 |

This procedure can remove up to 99% of up to 20 equivalents of unreacted NHS ester PSMA scaffold at 30 min and can be used to remove unclicked CTT1402 from radiolabeled final product.

Internalization Studies and Cell Specificity

Uptake and Internalization of CTT1403

The positive control PC3-PIP (PIP) cells, which stably express human PSMA, were compared against a negative control PC3 (PSMA−) cell line. PIP and PC3 cells were seeded separately in 12 well plates (4.0×10$^5$ cells/well) and incubated overnight. Cells were washed with internalization buffer (50 mM HEPES, 100 mM NaCl, 1% FBS)×1 and incubated for 30 min in internalization buffer or internalization buffer with 2 μg 2-PMPA as a blocking agent. Wells were washed ×1 followed by the addition of $^{177}$Lu-CTT1403 (8 ng) and incubated for 15, 30, 60, 120, and 240 min at 37° C. To collect surface bound fractions at each time point, samples were washed ×2 with internalization buffer followed by 10 min incubation with 20 mM sodium acetate in HBSS (pH 4.0). The solution was removed and saved, followed by a wash of 20 mM sodium acetate in HBSS without incubation, and the pooling of the two solutions. The cells were then lysed by rinsing each well with 0.5% SDS in ddH$_2$O×2. All samples were counted using a Cobra II automated gamma-counter.

Uptake and internalization of CTT1403 increased over time, with very low nonspecific uptake (see below). Nearly 100% of CTT1403 that bound to target cells were internalized (see table, below). These results indicate that CTT1403 successfully binds to its target on PSMA-expressing cells, is rapidly internalized, and continues to increase beyond 4 hours (FIG. 1).

| | | CTT-1403 | | |
|---|---|---|---|---|
| Time (min) | Surface | Internalized | Total | Ratio Internalized |
| 15 | 5.29 ± 0.96% | 18.67 ± 0.52% | 25.13 ± 1.23% | 77.03 ± 3.11% |
| 30 | 8.72 ± 0.52% | 31.13 ± 0.63% | 41.65 ± 0.92% | 77.09 ± 1.13% |
| 120 | 4.73 ± 0.92% | 43.55 ± 4.55% | 50.05 ± 3.66% | 88.98 ± 2.68% |
| 240 | 0.39 ± 0.03% | 83.43 ± 3.53% | 84.65 ± 3.55% | 99.17 ± 0.07% |

In Vivo Performance of a PSMA-Targeted Radiotherapeutic Platform Containing an Albumin-Binding Motif.

Biodistribution of PSMA-Targeted Radiotherapeutic Agent CTT1403

30 NCr nude mice were injected with $1\times10^6$ PC3 (PSMA+) cells subcutaneously in the right shoulder. Tumors were allowed to grow until approximately 0.8 cm across longest axis of measurement (21 days post injection). Mice were injected with 50 µCi (±2 µCi) of $^{177}$Lu-CTT1403 via tail vein. Blocking was performed by pre-treating mice with 2-(phosphonomethyl) pentane-1,5-dioic acid (PMPA) 30 min prior to injection of $^{177}$Lu-CTT1403. Animals were euthanized and tissues harvested at 1 h, 4 h, 4 h (blocked), 24 h, 48 h and 72 h post-injection. In addition, the biodistribution of CTT1403 was also determined at 120 h and 168 h. Blood, kidney, liver, lung, spleen, muscle, heart, bone, tumor, prostate, small intestine, large intestine, stomach and lacrimal glands were harvested. Tissue samples were counted in a gamma counter for 3 min each. Post-weights were taken to determine mass of tissue. Tissue weights and CPM $^{177}$Lu were used to calculate biodistribution.

Figure 2:
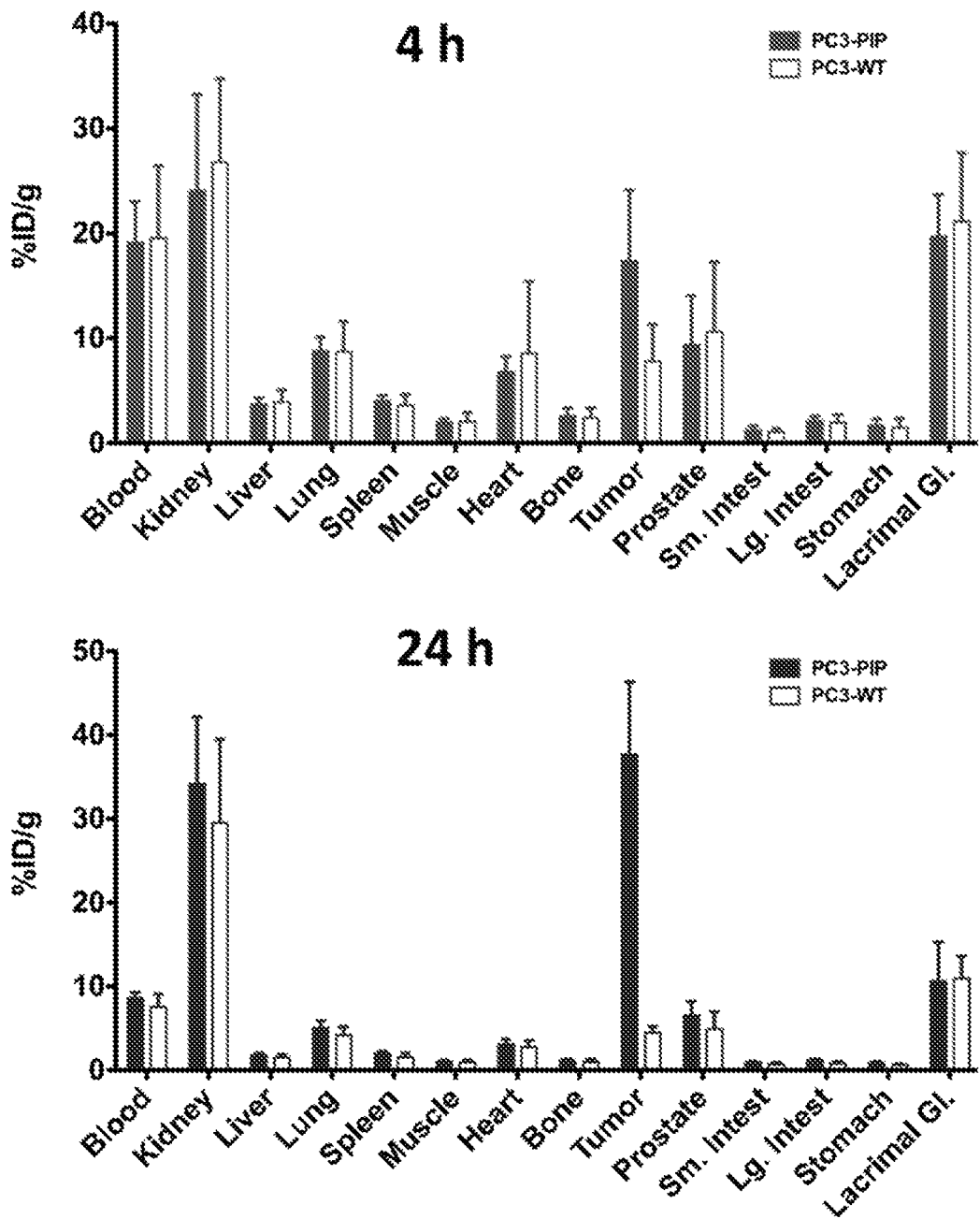
FIG. 2 shows biodistribution of CTT1403 in PC3-PIP and PC3-WT tumor-bearing mice at 4 and 24 hours as determined by radioactivity per gram of tissue.

As a control experiment, 10 NCr nude mice were injected with $1\times10^6$ PC3 (PSMA−) cells subcutaneously in the right shoulder. Tumors were allowed to grow until approximately 0.8 cm across longest axis of measurement (34 days post injection). Mice were injected with 50 µCi (±2 µCi) of $^{177}$Lu-CTT1403 tracer via tail vein. Animals were euthanized and tissues harvested at 4 and 24 h post-injection. Blood, kidney, liver, lung, spleen, muscle, heart, bone, tumor, prostate, small intestine, large intestine, stomach and lacrimal glands were harvested. Tissue samples were counted in a gamma counter for 3 min each. Post-weights were taken to determine mass of tissue. Tissue weights and cpm were used to calculate biodistribution (FIG. 2).

$^{177}$Lu-CTT1403 showed notable uptake in kidney, lung, prostate, GI tract, lacrimal glands and PC3 (+) tumor. The PC3(−) tumors, which do not express prostate-specific membrane antigen (PSMA), had low to negligible uptake. Normal mouse prostate did show some uptake of the tracer. The tumor and kidney uptake of $^{177}$Lu-CTT1403 are maximum around 48-72 h post-injection, with tumor:background ratios continuing to rise at 72 h. The tumor:kidney ratios for $^{177}$Lu-CTT1403 are 2-4 fold higher than other known tracers. The slower clearance of $^{177}$Lu-CTT1403 is much better aligned to the longer half-life of Lu-177.

Biodistribution Data for $^{177}$Lu-CTT1403 in PC3-PIP Cells:

| | PC3-PIP (PSMA+) | | | | | | | |
|---|---|---|---|---|---|---|---|---|
| | 1 h p.i. | 4 h p.i. | 24 h p.i. | 48 h p.i. | 72 h p.i. | 4120 h p.i. | 168 h p.i. | 4 h blocked |
| Blood | 25.81 ± 4.22 | 19.11 ± 3.94 | 8.63 ± 0.63 | 5.82 ± 1.57 | 2.88 ± 0.93 | 1.25 ± 0.25 | 0.54 ± 0.14 | 21.02 ± 2.58 |
| Kidney | 12.35 ± 3.24 | 24.07 ± 9.17 | 34.13 ± 8.0 | 52.76 ± 11.54 | 47.86 ± 12.72 | 49.13 ± 16.91 | 34.59 ± 8.60 | 12.49 ± 3.82 |
| Liver | 5.27 ± 1.04 | 3.74 ± 0.59 | 1.77 ± 0.24 | 1.25 ± 0.46 | 0.61 ± 0.20 | 0.29 ± 0.09 | 0.16 ± 0.04 | 4.09 ± 0.44 |
| Lung | 11.13 ± 2.38 | 8.79 ± 1.33 | 5.05 ± 0.86 | 3.56 ± 1.05 | 1.63 ± 0.62 | 0.69 ± 0.16 | 0.35 ± 0.08 | 10.84 ± 2.34 |
| Spleen | 4.69 ± 0.55 | 4.04 ± 0.51 | 2.02 ± 0.23 | 1.49 ± 0.52 | 0.86 ± 0.31 | 0.44 ± 0.10 | 0.29 ± 0.07 | 4.38 ± 0.43 |
| Muscle | 1.86 ± 0.34 | 1.97 ± 0.36 | 1.05 ± 0.11 | 0.69 ± 0.15 | 0.32 ± 0.09 | 0.15 ± 0.04 | 0.06 ± 0.01 | 2.05 ± 0.28 |
| Heart | 7.84 ± 1.31 | 6.80 ± 1.46 | 3.11 ± 0.58 | 2.13 ± 0.59 | 1.10 ± 0.52 | 0.49 ± 0.13 | 0.20 ± 0.09 | 8.09 ± 1.67 |
| Bone | 2.65 ± 0.47 | 2.60 ± 0.76 | 1.20 ± 0.11 | 0.86 ± 0.35 | 0.43 ± 0.11 | 0.22 ± 0.04 | 0.12 ± 0.02 | 2.35 ± 0.16 |
| Tumor | 5.02 ± 0.67 | 17.38 ± 6.75 | 37.67 ± 8.66 | 45.36 ± 6.24 | 46.48 ± 14.48 | 35.04 ± 13.23 | 24.23 ± 4.20 | 9.28 ± 3.11 |
| Prostate | 16.77 ± 5.20 | 9.35 ± 4.69 | 6.54 ± 1.69 | 6.36 ± 3.85 | 1.88 ± 1.90 | 0.22 ± 0.05 | 0.12 ± 0.06 | 18.61 ± 7.74 |
| Small Intestine | 1.05 ± 0.13 | 1.24 ± 0.43 | 0.93 ± 0.14 | 0.69 ± 0.17 | 0.50 ± 0.15 | 0.26 ± 0.10 | 0.33 ± 0.10 | 1.35 ± 0.39 |
| Large Intestine | 2.20 ± 0.31 | 2.14 ± 0.42 | 1.20 ± 0.14 | 0.75 ± 0.21 | 0.43 ± 0.13 | 0.33 ± 0.11 | 0.89 ± 0.22 | 2.58 ± 0.63 |
| Stomach | 0.89 ± 0.11 | 1.69 ± 0.62 | 0.90 ± 0.13 | 0.58 ± 0.20 | 0.34 ± 0.11 | 0.24 ± 0.09 | 0.46 ± 0.17 | 1.85 ± 0.43 |
| Lacrimal Gland | 18.95 ± 5.40 | 19.69 ± 3.99 | 10.65 ± 4.63 | 6.70 ± 2.41 | 2.98 ± 2.30 | 0.75 ± 0.12 | 1.17 ± 0.48 | 22.36 ± 5.76 |

The biodistribution data above indicates that specific tumor uptake of CTT1403 is observed by 4 and 24 hours and that the PSMA negative tumors have minimum uptake. Tumor uptake and kidney uptake is blocked up to 50% using the natural substrate PMPA. PMPA is a reversible inhibitor of PSMA and is not expected to completely block all specific PSMA dependent uptake. It should be noted that unlike human kidney, rodent kidney demonstrates substantial levels of PSMA expression and kidney clearance kinetics is somewhat obscured by this specific PSMA uptake.

| Biodistribution to normal tissues and PSMA + Tumors | | |
| --- | --- | --- |
| Tumor % ID/g at 4 hrs | 3.00 +/− 0.84 | 17.38 +/− 6.75 |
| Tumor % ID/g at 4 hrs blocked with PMPA | 1.12 +/− 0.17 | 9.28 +/− 3.11 |
| Tumor % ID/g at 72 hrs | 0.98 +/− 0.08 | 35.47 +/− 7.92 |
| Tumor/Blood (4 hrs) | 300.2 +/− 84.39 | 0.98 +/− 0.58 |
| Tumor/Blood (24 hrs) | 211 +/− 51.93 | 4.35 +/− 0.82 |
| Tumor/Blood (72 hrs) | 97.6 +/− 8.47 | 14.97 +/− 5.39 |
| Tumor/Kidney (4 hrs) | 0.46 +/− 0.44 | 0.83 +/− 0.57 |
| Tumor/Kidney (24 hrs) | 0.15 +/− 0.04 | 1.17 +/− 0.39 |
| Tumor/Kidney (72 hrs) | 0.18 +/− 0.11 | 0.80 +/− 0.33 |
| Tumor/Muscle (4 hrs) | 90.72 +/− 59.87 | 9.25 +/− 5.01 |
| Tumor/Muscle (24 hrs) | 211 +/− 51.93 | 35.94 +/− 7.44 |
| Tumor/Muscle (72 hrs) | 97.6 +/− 847 | 133.45 +/− 27.96 |

CTT1403 tumor uptake continues to increase over time (17% at 4 hrs) reaching a maximum at 48-72 hours post injection (35% at 72 hrs). Over this same time period kidney binding shows the expected clearance. Tumor to blood and tumor to muscle ratios continue to increase over the first 72 hours post injection of CTT1403.

Therapeutic Efficacy of CTT1403 (Single Dose)

Figure 3:
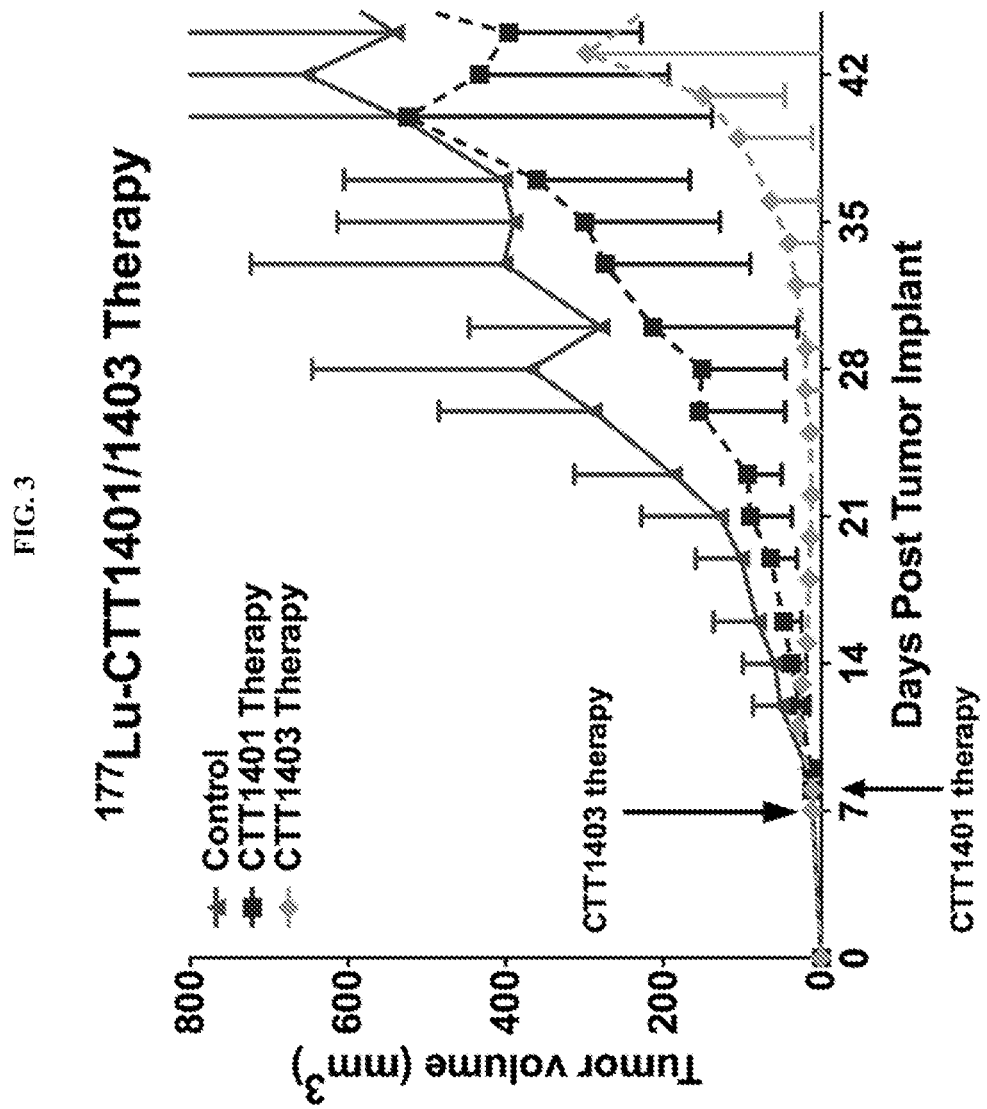
FIG. 3 shows therapeutic efficacy of CTT1403 (9 animals) vs control (7 animals) in mice bearing PSMA-positive (PSMA+) human tumor xenografts. Mice were injected when starting tumor volumes reached 10-20 mm³.
Figure 4:
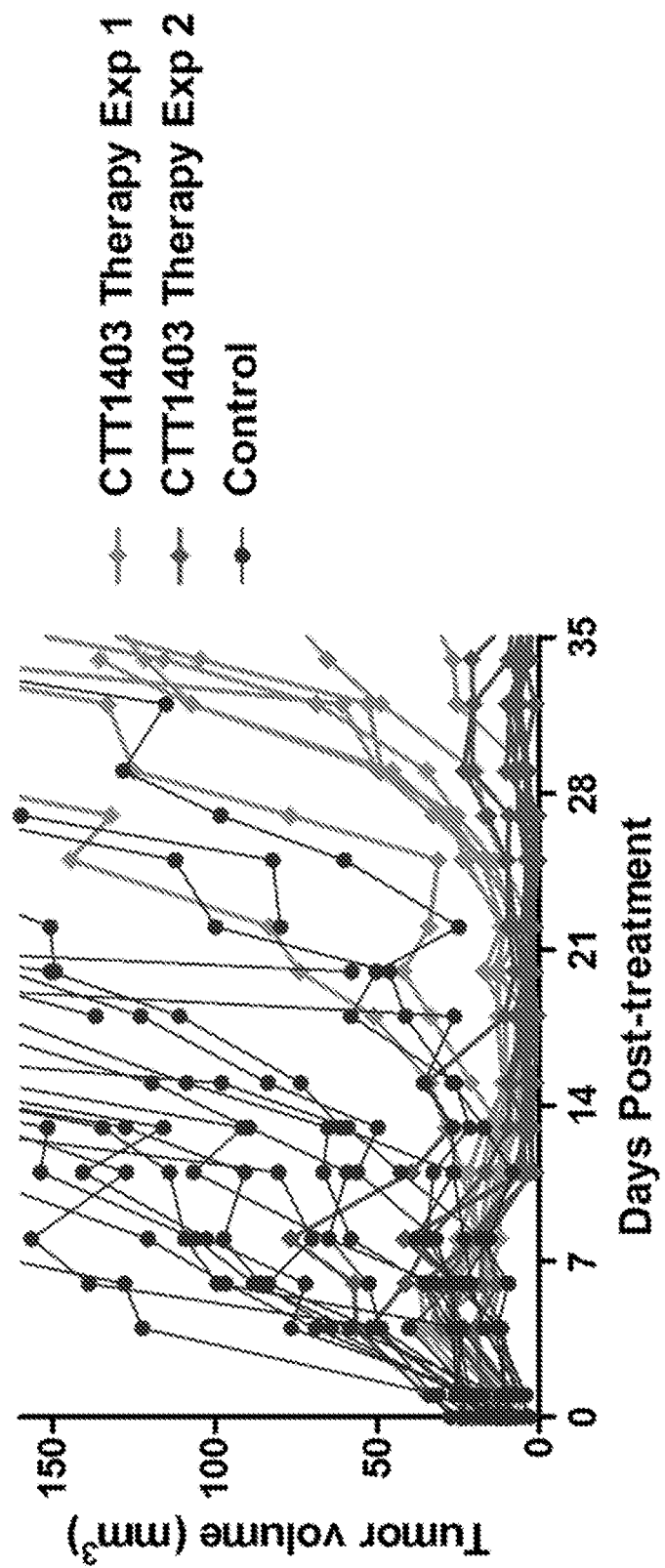
FIG. 4 shows therapeutic efficacy of CTT1403 (Comparison of experiment 1 and 2) vs control in mice bearing PSMA+ human tumor xenografts. Mice were injected when starting tumor volumes reached 10-20 mm³.

Fifteen NCr nude mice were injected with $3 \times 10^5$ PC3 (PSMA+) cells subcutaneously in the right shoulder 7 days before start of the therapy using $^{177}$Lu-CTT1403 (10 mice). Average starting tumor volume at start of treatment was 10-20 mm$^3$. Each mouse was injected with 790 µCi (±10 µCi) of CTT1403 tracer via tail vein. Control mice (2) were injected with saline via tail vein. Body weights and tumor volumes were measured before the injection as day 7 followed by measurements three times per week. The tumor volume (V) was determined according to the equation [$V=(\pi \div 6) \times L \times W \times H$], where L is the longest axis and W is the perpendicular axis to L, and H is the perpendicular axis to L and W plane. Endpoint criteria were defined as longest axis of measurement of tumor exceeds 1.5 cm or active ulceration of the tumor (FIG. 3). Mouse weights were also recorded but no abnormal changes were observed in any of the weights (no reduction in normal growth).

Figure 5:
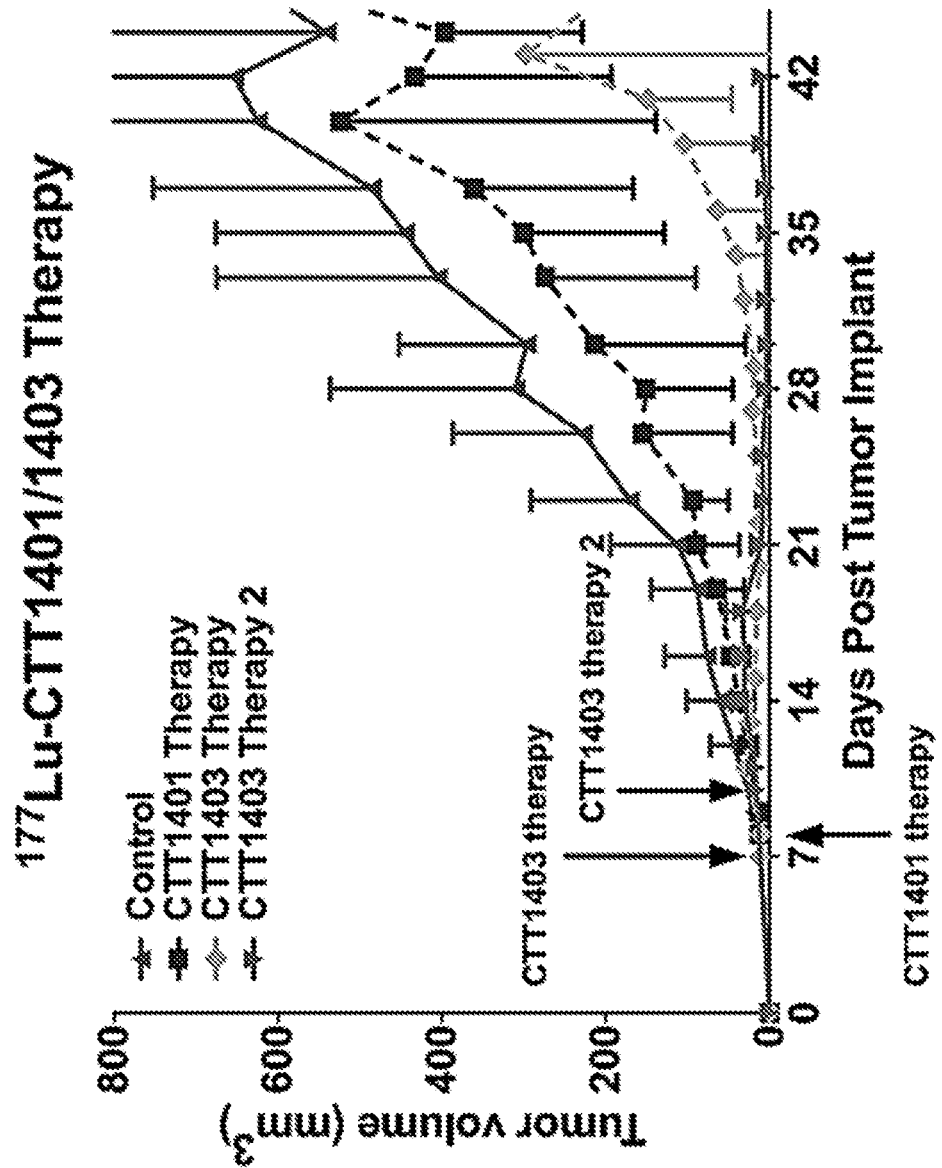
FIG. 5 shows expanded scale of FIG. 4. Therapeutic Efficacy of CTT1403 (2 experiments) vs control in mice bearing PSMA+ human tumor xenografts.
Figure 6:
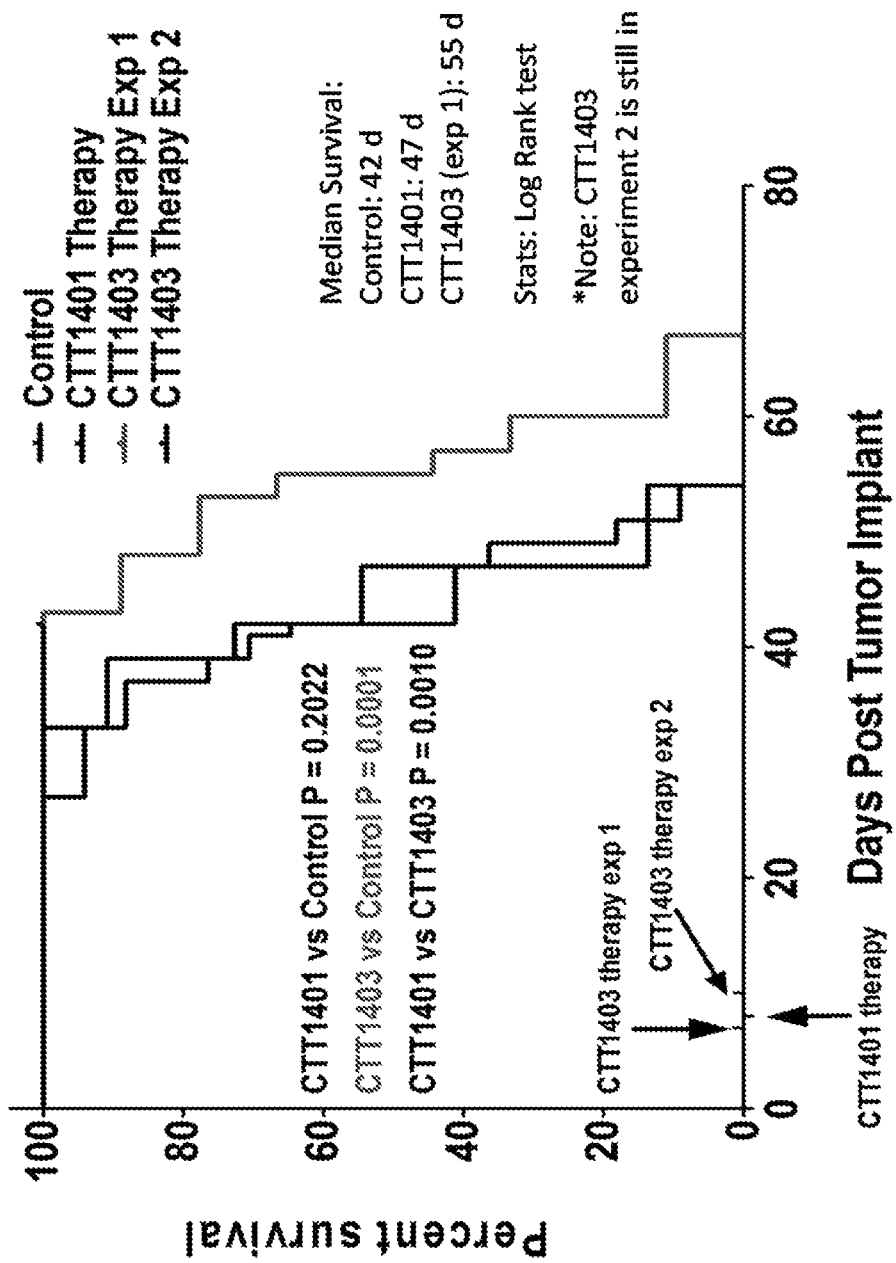
FIG. 6 shows Kaplan Meier Survival Plots of CTT1403 Treated Mice. Comparison of repeat therapy (8 animals) experiments (as of day 42 of experiment) as compared to untreated control mice (17 animals). Median survival times are 42 days for control group and 55 days for expt 1 CTT1403 group, post tumor implant. This represents a 14% and 31% increase in survival, respectively. No animal has been sacrificed for the expt 2 CTT1403 treatment group as of day 42 of the experiment.

The therapy experiment was repeated with CTT1403 (purity was increased for this second experiment to 95% [CTT1403 Therapy 2] as compared to 85-90% purity for the first experiment [CTT1403 Therapy]) to confirm results. Fifteen NCr nude mice were injected with $3 \times 10^5$ PC3 (PSMA+) cells subcutaneously in the right shoulder 10 days before start of the therapy using $^{177}$Lu-CTT1403. 8 control animals were injected with only saline via tail vein. 8 mice were injected with 790 µCi (±10 µCi) of $^{177}$Lu-CTT1403 tracer via tail vein. Body weights and tumor volumes were measured before the injection as day 0 followed by measurements three times per week. The tumor volume (V) was determined according to the equation [$V=\pi \div 6 \times L \times W \times H$], where L is the longest axis and W is the perpendicular axis to L, and H is the perpendicular axis to L and W plane. Endpoint criteria were defined as longest axis of measurement of tumor exceeds 1.5 cm or active ulceration of the tumor The increased tumor uptake observed in the biodistribution experiments for CTT1403 (with the albumin binding motif) translates to superior therapeutic efficacy of CTT1403 in PSMA+ human xenograft tumor models as demonstrated by significantly increased tumor doubling times, 90-95% reduction in tumor volume within the first 3 weeks of tumor growth and 31% increase in median survival time based on the first 1403 treatment experiment (median survival time for the second 1403 treatment experiment is still 100% as of day 42 of the experiment) based on the Kaplan Meier survival plots as demonstrated in FIGS. 5 and 6.

Definitions

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" PSMA with a compound includes the administration of a compound described herein to an individual or patient, such as a human, as well as, for example, introducing a compound into a sample containing a cellular or purified preparation containing PSMA.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—(CH$_2$)n-COOH where n is 0-4, and the like. Non-toxic pharmaceutical base addition salts include salts of bases such as sodium, potassium, calcium, ammonium, and the like. In certain embodiments, the pharmaceutically acceptable salt is a sodium salt. Those skilled in the art will recognize a wide variety of non-toxic pharmaceutically acceptable addition salts.

Pharmaceutical compositions suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Compositions can be administered, for example, by intravenous infusion, orally, topically, intraperitoneally, intravesically or intrathecally.

The term "alkyl" as used herein, means a straight or branched chain hydrocarbon containing from 1 to 10 carbon atoms, unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2- dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —CH$_2$—, —CH$_2$CH$_2$—, —CH$_2$CH$_2$CHC(CH$_3$)—, —CH$_2$CH(CH$_2$CH$_3$)CH$_2$—.

The term "heterocyclyl" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-di hydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "thia" as used herein means a =S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

We claim:

1. A compound of the formula (Ib):

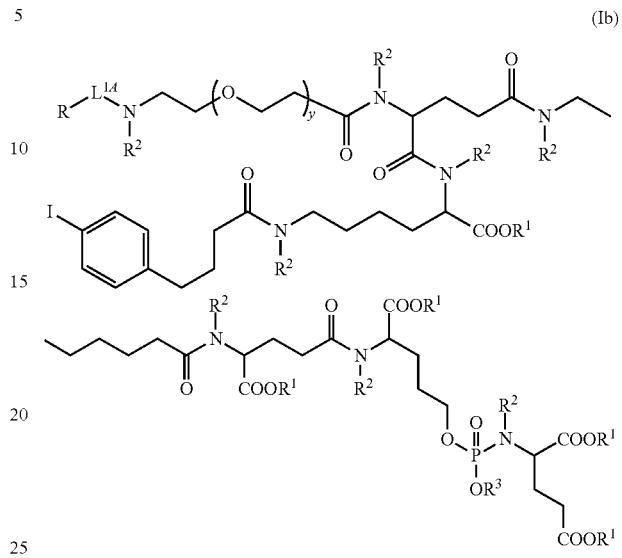

(Ib)

or a pharmaceutically acceptable salt thereof,
wherein
L$^{1A}$ is a divalent linking group;
R is a chelating agent optionally chelating a therapeutic radioisotope or a PET-active, SPECT-active, or MRI-active radioisotope; and
each R$^1$ and R$^2$ are independently hydrogen, C$_1$-C$_6$ alkyl or a protecting group;
R$^3$ is hydrogen; and
y is 2, 3, 4, 5 or 6.

2. The compound of claim 1, wherein y is 4.

3. The compound of claim 1, wherein R comprises DOTA, NOTA, PCTA, DO3A, HBED, NODAG, CB-TE2A, CB-TE1K1P or desferrioxamine.

4. The compound of claim 1, wherein R comprises DOTA.

5. The compound of claim 1, wherein the chelating agent is chelating a therapeutic radioisotope or a PET-active, SPECT-active, or MRI-active radioisotope that is $^{89}$Zr, $^{64}$Cu, $^{68}$Ga, $^{186/188}$Re, $^{90}$Y, $^{177}$Lu, $^{153}$Sm, $^{213}$Bi, $^{225}$AC, or $^{223}$Ra.

6. A pharmaceutical composition comprising a compound of claim 1 and a pharmaceutically acceptable carrier.

7. A method for imaging one or more prostate cancer cells in a patient comprising administering to the patient a compound of claim 1, and imaging the patient.

8. A compound according to claim 1, wherein the divalent linking group L$^{1A}$ is a group of the formula:

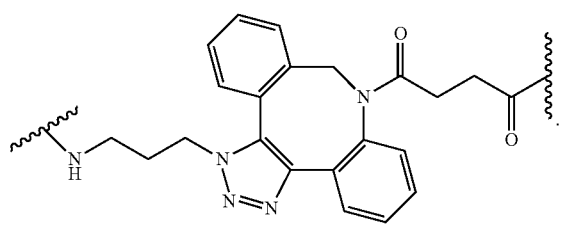 [SMILES: *NCCCn1nnc2c1-c1ccccc1CN(C(=O)CCC(*)=O)c1ccccc1-2]

9. A compound according to claim 1, wherein chelating agent R is a group of the formula:

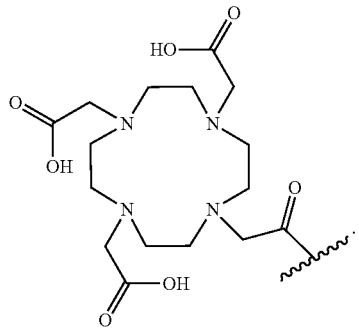 [SMILES: *C(=O)CN1CCN(CC(=O)O)CCN(CC(=O)O)CCN(CC(=O)O)CC1]

10. A compound according to claim 8, wherein chelating agent R is a group of the formula:

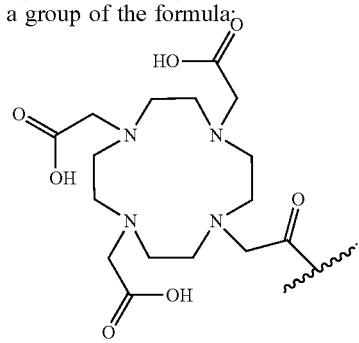

11. A compound according to claim 10, wherein y is 4.

12. A compound according to claim 11, wherein $R^1$ and $R^2$ are hydrogen.

13. A compound according to claim 12, wherein the chelating agent is chelating a therapeutic radioisotope or a PET-active, SPECT-active, or MRI-active radioisotope that is $^{177}$Lu.

14. The compound of claim 12 that is:

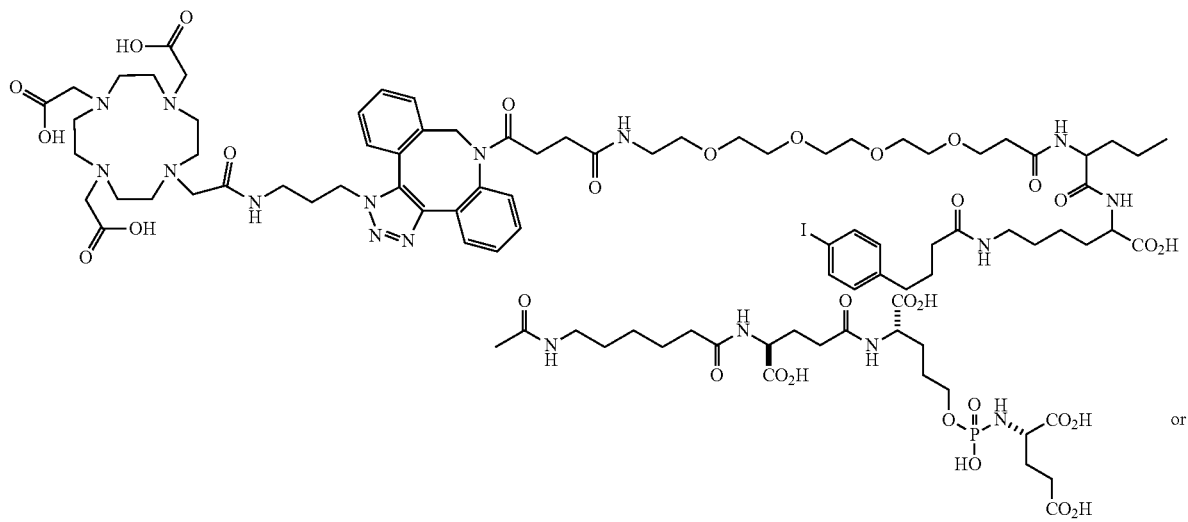

or

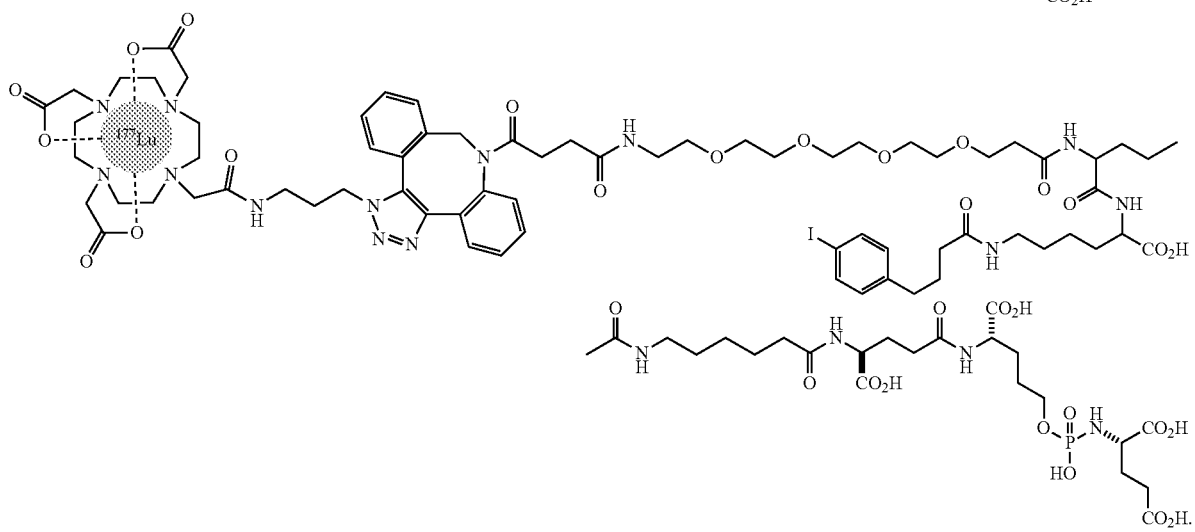

* * * * *